US012696884B2

(12) United States Patent     (10) Patent No.:   US 12,696,884 B2

Murphy et al.     (45) Date of Patent:   *Aug. 4, 2026

(54) GENETICALLY MODIFIED NON-HUMAN ANIMALS EXPRESSING HUMAN EPO

(71) Applicants: Regeneron Pharmaceuticals, Inc., Tarrytown, NY (US); Yale University, New Haven, CT (US); Institute for Research in Biomedicine (IRB), Bellinzona (CH)

(72) Inventors: Andrew J. Murphy, Croton-on-Hudson, NY (US); Sean Stevens, San Francisco, CA (US); Richard Flavell, Guilford, CT (US); Markus Gabriel Manz, Zürich (CH); Liang Shan, New Haven, CT (US)

(73) Assignees: Regeneron Pharmaceuticals, Inc., Tarrytown, NY (US); Yale University, New Haven, CT (US); Institute for Research in Biomedicine (IRB), Bellinzona (CH)

( * ) Notice: Subject to any disclaimer, the term of this patent is extended or adjusted under 35 U.S.C. 154(b) by 405 days.

This patent is subject to a terminal disclaimer.

(21) Appl. No.: 18/448,062

(22) Filed: Aug. 10, 2023

(65) Prior Publication Data

US 2024/0074414 A1    Mar. 7, 2024

Related U.S. Application Data

(60) Continuation of application No. 16/672,042, filed on Nov. 1, 2019, now Pat. No. 11,766,032, which is a (Continued)

(51) Int. Cl.

| | |
|---|---|
| *A01K 67/00* | (2006.01) |
| *A01K 67/0271* | (2024.01) |
| *A01K 67/0276* | (2024.01) |
| *A01K 67/0278* | (2024.01) |
| *A61K 49/00* | (2006.01) |
| *C07K 14/47* | (2006.01) |
| *C07K 14/475* | (2006.01) |
| *C07K 14/505* | (2006.01) |
| *C07K 14/52* | (2006.01) |
| *C07K 14/535* | (2006.01) |
| *C07K 14/54* | (2006.01) |
| *C07K 14/715* | (2006.01) |

(Continued)

(52) U.S. Cl.

CPC ...... *A01K 67/0271* (2013.01); *A01K 67/0276* (2013.01); *A01K 67/0278* (2013.01); *A61K 49/0008* (2013.01); *C07K 14/4703* (2013.01); *C07K 14/475* (2013.01); *C07K 14/505* (2013.01); *C07K 14/524* (2013.01); *C07K 14/535* (2013.01); *C07K 14/5403* (2013.01); *C07K 14/5437* (2013.01); *C07K 14/7155*

(2013.01); *C12N 9/00* (2013.01); *C12N 9/14* (2013.01); *C12Q 1/18* (2013.01); *G01N 33/5088* (2013.01); *A01K 2207/12* (2013.01); *A01K 2207/15* (2013.01); *A01K 2217/05* (2013.01); *A01K 2217/072* (2013.01); *A01K 2217/075* (2013.01); *A01K 2217/15* (2013.01); *A01K 2227/105* (2013.01); *A01K 2267/01* (2013.01); *A01K 2267/0337* (2013.01); *A01K 2267/0381* (2013.01); *C12Y 301/03048* (2013.01)

(58) Field of Classification Search

None

See application file for complete search history.

(56) References Cited

U.S. PATENT DOCUMENTS

| | | | |
|---|---|---|---|
| 4,736,866 | A | 4/1988 | Leder et al. |
| 4,870,009 | A | 9/1989 | Evans et al. |

(Continued)

FOREIGN PATENT DOCUMENTS

| | | |
|---|---|---|
| AU | 2013204613 A1 | 5/2013 |
| CN | 1748143 | 3/2006 |

(Continued)

OTHER PUBLICATIONS

Zhu et al. (2019) "Humanising the mouse genome piece by piece", Nature Communications, 10:1845, 1-13.

(Continued)

*Primary Examiner* — Michael D Burkhart

(74) *Attorney, Agent, or Firm* — Brian E. Davy; Bozicevic, Field & Francis LLP

(57) ABSTRACT

Genetically modified non-human animals expressing human EPO from the animal genome are provided. Also provided are methods for making non-human animals expressing human EPO from the non-human animal genome, and methods for using non-human animals expressing human EPO from the non-human animal genome. These animals and methods find many uses in the art, including, for example, in modeling human erythropoiesis and erythrocyte function; in modeling human pathogen infection of erythrocytes; in in vivo screens for agents that modulate erythropoiesis and/or erythrocyte function, e.g. in a healthy or a diseased state; in in vivo screens for agents that are toxic to erythrocytes or erythrocyte progenitors; in in vivo screens for agents that prevent against, mitigate, or reverse the toxic effects of toxic agents on erythrocytes or erythrocyte progenitors; in in vivo screens of erythrocytes or erythrocyte progenitors from an individual to predict the responsiveness of an individual to a disease therapy.

20 Claims, 8 Drawing Sheets

Specification includes a Sequence Listing.

Related U.S. Application Data division of application No. 14/715,446, filed on May 18, 2015, now Pat. No. 10,463,028.

(60) Provisional application No. 62/000,460, filed on May 19, 2014.

(51) Int. Cl.

| | | |
|---|---|---|
| *C12N 9/00* | (2006.01) |
| *C12N 9/14* | (2006.01) |
| *C12Q 1/18* | (2006.01) |
| *G01N 33/50* | (2006.01) |

(56) References Cited

U.S. PATENT DOCUMENTS

| | | | |
|---|---|---|---|
| 5,222,982 | A | 6/1993 | Ommaya |
| 5,385,582 | A | 1/1995 | Ommaya |
| 5,573,930 | A | 11/1996 | Ladner et al. |
| 5,583,278 | A | 12/1996 | Alt et al. |
| 5,633,426 | A | 5/1997 | Namikawa et al. |
| 5,652,373 | A | 7/1997 | Reisner et al. |
| 5,663,481 | A | 9/1997 | Gallinger et al. |
| 5,681,729 | A | 10/1997 | Kudo et al. |
| 5,709,843 | A | 1/1998 | Reisner et al. |
| 5,750,826 | A | 5/1998 | Borkowski et al. |
| 5,849,288 | A | 12/1998 | Reisner et al. |
| 5,866,757 | A | 2/1999 | Reisner et al. |
| 6,018,096 | A | 1/2000 | Keating et al. |
| 6,248,721 | B1 | 6/2001 | Chang |
| 6,353,150 | B1 | 3/2002 | Dick et al. |
| 6,455,756 | B1 | 9/2002 | Chen et al. |
| 6,586,251 | B2 | 7/2003 | Economides et al. |
| 7,273,753 | B2 | 9/2007 | Crawford et al. |
| 7,294,754 | B2 | 11/2007 | Poueymirou et al. |
| 7,576,259 | B2 | 8/2009 | Poueymirou et al. |
| 7,659,442 | B2 | 2/2010 | Poueymirou et al. |
| 7,759,541 | B2 | 7/2010 | Wolf et al. |
| 8,541,646 | B2 | 9/2013 | Stevens et al. |
| 8,692,052 | B2 | 4/2014 | Stevens et al. |
| 8,847,004 | B2 | 9/2014 | Murphy et al. |
| 8,878,001 | B2 | 11/2014 | Wang et al. |
| 9,127,292 | B2 | 9/2015 | Murphy et al. |
| 9,155,290 | B2 | 10/2015 | Rojas |
| 9,193,977 | B2 | 11/2015 | Murphy et al. |
| 9,301,509 | B2 | 4/2016 | Stevens et al. |
| 9,402,377 | B2 | 8/2016 | Flavell |
| 9,462,794 | B2 | 10/2016 | Murphy et al. |
| 9,554,563 | B2 | 1/2017 | Stevens et al. |
| 9,655,352 | B2 | 5/2017 | Murphy et al. |
| 9,820,476 | B2 | 11/2017 | Flavell et al. |
| 9,901,082 | B2 | 2/2018 | Flavell et al. |
| 9,986,724 | B2 | 6/2018 | Flavell et al. |
| 10,123,518 | B2 | 11/2018 | Herndler-Brandstetter et al. |
| 10,278,374 | B2 | 5/2019 | Stevens |
| 10,433,527 | B2 | 10/2019 | Flavell et al. |
| 10,561,126 | B2 | 2/2020 | Herndler-Brandstetter et al. |
| 11,026,408 | B2 | 6/2021 | Flavell et al. |
| 11,051,499 | B2 | 7/2021 | Stevens |
| 2002/0037523 | A1 | 3/2002 | Ruben et al. |
| 2003/0028911 | A1 | 2/2003 | Huang et al. |
| 2005/0208474 | A1 | 9/2005 | Lau et al. |
| 2007/0254842 | A1 | 11/2007 | Bankiewicz |
| 2008/0081064 | A1 | 4/2008 | Jelle et al. |
| 2008/0311095 | A1 | 12/2008 | Holmes et al. |
| 2009/0196903 | A1 | 8/2009 | Kliman |
| 2011/0200982 | A1 | 8/2011 | Stevens et al. |
| 2012/0157667 | A1 | 6/2012 | Chen |
| 2013/0022996 | A1 | 1/2013 | Stevens et al. |
| 2013/0024957 | A1 | 1/2013 | Stevens et al. |
| 2013/0042330 | A1 | 2/2013 | Murphy et al. |
| 2013/0117873 | A1 | 5/2013 | Wang et al. |
| 2014/0090095 | A1 | 3/2014 | Stevens et al. |
| 2014/0134662 | A1 | 5/2014 | Flavell et al. |
| 2015/0047061 | A1 | 2/2015 | Murphy et al. |
| 2015/0089678 | A1 | 3/2015 | Murphy et al. |
| 2015/0089679 | A1 | 3/2015 | Murphy et al. |
| 2015/0208622 | A1 | 7/2015 | Flavell et al. |
| 2015/0327524 | A1 | 11/2015 | Murphy et al. |
| 2016/0050896 | A1 | 2/2016 | Murphy et al. |
| 2016/0295844 | A1 | 10/2016 | Herndler-Brandstetter et al. |
| 2016/0366862 | A1 | 12/2016 | Flavell et al. |
| 2016/0374321 | A1 | 12/2016 | Murphy et al. |
| 2017/0172121 | A1 | 6/2017 | Murphy et al. |
| 2018/0020647 | A1 | 1/2018 | Flavell et al. |
| 2018/0295820 | A1 | 10/2018 | Herndler-Brandstetter et al. |
| 2019/0082663 | A1 | 3/2019 | Flavell et al. |
| 2019/0216779 | A1 | 7/2019 | Basta et al. |
| 2019/0297862 | A1 | 10/2019 | Stevens et al. |
| 2020/0229410 | A1 | 7/2020 | Herndler-Brandstetter et al. |
| 2021/0100228 | A1 | 4/2021 | Flavell et al. |
| 2021/0112791 | A1 | 4/2021 | Murphy et al. |
| 2021/0368752 | A1 | 12/2021 | Flavell et al. |
| 2022/0000084 | A1 | 1/2022 | Murphy et al. |

FOREIGN PATENT DOCUMENTS

| | | |
|---|---|---|
| CN | 101250553 | 8/2008 |
| EP | 0322240 | 6/1989 |
| EP | 0438053 | 7/1991 |
| EP | 0517199 | 12/1992 |
| EP | 1452093 | 9/2004 |
| GB | 2434578 A | 8/2007 |
| JP | 2002501375 | 1/2002 |
| JP | 2003-508038 A | 3/2003 |
| JP | 2007312772 A | 12/2007 |
| JP | 2009542253 | 12/2009 |
| RU | 2425880 | 2/2011 |
| WO | WO 1988003173 | 5/1988 |
| WO | WO 1989012823 | 12/1989 |
| WO | WO 1991016910 | 11/1991 |
| WO | WO 1991018615 | 12/1991 |
| WO | WO 1993005796 | 4/1993 |
| WO | WO9950657 A1 | 10/1999 |
| WO | WO 200115521 | 3/2001 |
| WO | WO 2002066630 | 8/2002 |
| WO | WO 2003018744 | 3/2003 |
| WO | WO 2003039232 | 5/2003 |
| WO | WO 2004005496 | 1/2004 |
| WO | WO 2004022738 | 3/2004 |
| WO | WO 2004044003 | 5/2004 |
| WO | WO 2004060052 | 7/2004 |
| WO | WO 2008069659 | 6/2008 |
| WO | WO 2009034328 | 3/2009 |
| WO | WO 2009042917 | 4/2009 |
| WO | WO 2008010100 | 12/2009 |
| WO | WO 2011002721 | 1/2011 |
| WO | WO 2011002727 | 1/2011 |
| WO | WO 2011044050 | 4/2011 |
| WO | WO 2012040207 | 3/2012 |
| WO | WO 2012051572 | 4/2012 |
| WO | WO 2012112544 | 8/2012 |
| WO | WO 2013063556 | 5/2013 |
| WO | WO 2014039782 | 3/2014 |
| WO | WO 2014071397 | 5/2014 |
| WO | WO 2015042557 | 3/2015 |
| WO | WO 2016168212 | 10/2016 |

OTHER PUBLICATIONS

Horowitz et al., Humanized Mouse Models for the Advancement of Innate Lymphoid Cell-Based Cancer Immunotherapies, Frontiers in Immunology, vol. 12, Apr. 22, 2021.

Xia, Research on Functions of Immunologic Factors on Type I Diabetes Mellitus and Neoplasms, University of Science and Technology of China, Abstract, III-IV, 2009.

Hope et al.,"Differences in the induction of CD8+ T cell responses by subpopulations of dendritic cells from afferent lymph are related to IL-1α secretion" Journal of Leukocyte Biology, vol. 69, Issue 2, Feb. 2001, pp. 271-279.

Hawley et al., Hematopoletic stem cells, Methods Enzymol, 4 9:149-79 (2006).

(56)　　　　　References Cited

OTHER PUBLICATIONS

Hansen et al., Spontaneous and genetically engineered animal models: use in preclinical cancer drug development, European Journal of Cancer, 40(6):858-880, 2004.
King et al., A new Hu-PBL model for the study of human islet alloreactivity based on NOD-scid mice bearing a targeted mutation in the IL-2 receptor gamma chain gene, Clinical Immunology, 126(3):303-314, 2008.
NCBI 1 page printout for nucleotide sequence for human M-CSF, 2005.
Abadie V., et al; (2014) "IL-15: a central regulator of celiac disease immunopathology"; Immunol Rev. 260(1):221-34.
Abboud et al., (2003). "Analysis of the Mouse CSF-1 Gene Promoter in a Transgenic Mouse Model" The Journal of Histochemistry & Cytochemistry, 51(7):941-949.
Alves et al.; "Characterization of the thymic IL-7 niche in vivo"; Proceedings of the National Academy of Sciences, 106(5); pp. 1512-1517, (2009).
Angulo-Barturen Inigo, et al; "A Murine Model of falciparum-Malaria by In Vivo Selection of Competent Strains in Non-Myelodepleted Mice Engrafted with Human Erythrocytes"; PLoS ONE, vol. 3. No. 5; May 2008, pp. 1-14; XP055166984.
Appenheimer et al (2007) "Conservation of IL-6 trans-signaling mechanisms controlling L-selectin adhesion by fever-range thermal stress"; Eur J Immunol. 37(10):2856-2867.
Arranz Eduardo and Garrote Jose A; (2011) "IL-15 modulates the effect of retinoic acid, promoting inflammation rather than oral tolerance to dietary antigen"; Expert Rev. Gastroenterol. Hepatol. 5(3), pp. 315-317.
Ashizawa, et al.(2017) "Antitumor Effect of Programmed Death-1 (PD-1) Blockade in Humanized the NOG-MHC Double Knockout Mouse"; Clin Cancer Res; 23(1); pp. 149-158.
Auffray et al., (2009), "Blood monocytes: development, heterogeneity, and relationship with dendritic cells"; Annual review of immunology 27, 669-692.
Badell et al. (2000) Human malaria in immunocompromised mice: an in vivo model to study defense mechanisms against Plasmodium falciparum. JEM 192(11):1653-1660.
Baenziger et al., (2006), "Disseminated and Sustained HIV Infection in CD34+ Cord Blood Cell-Transplanted Rag2−/−γc−/− Mice"; Proc Natl Acad Sci USA 103: pp. 15951-15956.
Bartley, T.D. et al. (1994) Identification and cloning of a megakaryocyte growth and development factor that is a ligand for the cytokine receptor Mpl; Cell 77(7); pp. 1117-1124. (Abstract).
Becker et al., (2010), "Generation of Human Antigen-Specific Monoclonal IgM Antibodies Using Vaccinated "Human Immune System" Mice"; PLoS ONE 5(10); pp. 1-10.
Bergsagel et al., (2005), "Cyclin D dysregulation: an early and unifying pathogenic event in multiple myeloma"; Blood 106: pp. 296-303.
Bernard, et al; "Establishing humanized mice using stem cells: maximizing the potential"; Clinical & Experimental Immunology vol. 152, Issue 3, pp. 406-414, (Jun. 2008).
Bernier et al. (2001) "M-CSF Transgenic Mice: Role of M-CSF in Infection and Autoimmunity"; Exp. Toxic Pathology. 53: pp. 165-173.
Biedzka-Sarek; et al. "How to outwit the enemy: dendritic cells face Salmonella", APMIS (Sep. 2006), 114 (9):589-600.
Billerbeck, et al (2011) "Development of human CD4+FoxP3+ regulatory T cells in human stem cell factor-, granulocyte-macrophage colony-stimulating factor-, and interleukin-3-expressing NOD-SCID IL2Rγ(null) humanized mice"; Blood 117(11); pp. 3076-3086.
Bingle et al., (2002), "The role of tumour-associated macrophages in tumour progression: implications for new anticancer therapies"; T Journal of pathology 196: pp. 254-265.
Bird et al., (1988), "Single-Chain Antigen-Binding Proteins"; Science 242: pp. 423-426.

Bock; et al. "Improved Engraftment of Humanized Hematopoeitic Cells in Severe Combined Immunodeficient (SCID) Mice Carrying Human Cytokine Transgenes", Journal of Exp. Med. (Dec. 1995), 182:2037-2043.
Bosma et al. (1989), "The mouse mutation severe combined immune deficiency (scid) is on chromosome 16"; Immunogenetics 29: pp. 54-56.
Brehm et al., (2012), "Engraftment of human HSCs in nonirradiated newborn NOD-scid IL2rynull mice is enhanced by transgenic expression of membrane-bound human SCF"; Blood 119: pp. 2778-2788.
Brehm; et al. (2010) "Parameters for establishing humanized mouse models to study human immunity: Analysis of human hematopoeitic stem cell engraftment in three immunodeficient strains of mice bearing the IL2ry null mutation", Clinical Immunology 135:84-98.
Brevini TA, et al (2010) "No shortcuts to pig embryonic stem cells"; Theriogenology. 74(4); pp. 544-550.
Budzynski, et al (1994) "Cytotoxic cells in immunodeficient athymic mice"; Immunopharmacol Immunotoxicol 16(3); pp. 319-346.
Burger et al., (2001) "Gp130 and ras mediated signaling in human plasma cell line INA-6: a cytokine-regulated tumor model for plasmacytoma"; Hematol J, 2(1): pp. 42-53.
Calvi; et al. "Osteoblastic cells regulate the haematopoietic stem cell niche", Nature (Oct. 2003), 425:841-846.
Campbell et al., "Neurologic disease induced in transgenic mice by cerebral overexpression of interleukin 6," Proc. Natl. Acad. Sci. USA, 90:10061-10065, 1993.
Cao Shanbo et al., (2009) "Isolation and culture of primary bovine embryonic stem cell colonies by a novel method"; Journal of Experimental Zoology, 311(5); pp. 368-376.
Carstea et al (2009) "Germline competence of mouse ES and iPS cell lines: Chimera technologies and genetic background"; World Journals of Stem Cells, vol. 1, No. 1, pp. 22-29.
Chang, et al (2015) "Anti-CCR4 monoclonal antibody enhances antitumor immunity by modulating tumor-infiltrating Tregs in an ovarian cancer xenograft humanized mouse model"; Oncoimmunology 5(3):e1090075. 14 pages.
Chen et al., "Expression of human cytokines dramatically improves reconstitution of specific human-blood lineage cells in humanized mice" PNAS (Dec. 22, 2009) 106(51):21783-21788.
Chen et al., (2012) "Human extramedullary bone marrow in mice: a novel in vivo model of genetically controlled hematopoietic microenvironment"; Blood 119(21); pp. 4971-4980.
Cheng et al., "Therapeutic Antibodies Targeting CSF1 Impede Macrophage Recruitment in a Xenograft Model of Tenosynovial Giant Cell Tumor" Sarcoma, Article ID 174528, pp. 1-7 (2010).
Chicha et al. "Human Adaptive Immune System Rag2−/− γ c −/− Mice"; Annals of NY Academy of Science 104; (2005); pp. 236-243.
Chng et al. (2005) "A validated FISH trisomy index demonstrates the hyperdiploid and nonhyperdiploid dichotomy in MGUS"; Blood 106(6): pp. 2156-2161.
Chow et al., (2011) "Studying the mononuclear phagocyte system in the molecular age" Nature reviews Immunology 11: pp. 788-798.
Clark, et al.; "A future for transgenic livestock,", Natures Reviews, vol. 4; (Oct. 2003); pp. 825-833.
Cocco; et al. "CD34+ Cord Blood Cell-Transplanted Rag2−/−yc−/−Mice as a Model for Epstein-Barr Virus Infection", The American Journal of Pathology (Nov. 2008), 173(5):1369-1378.
Coussens et al. (2013) "Neutralizing tumor-promoting chronic inflammation: a magic bullet?"; Science 339: pp. 286-291.
Cros et al., (2010), "Human CD14dim Monocytes Patrol and Sense Nucleic Acids and Viruses via TLR7 and TLRS Receptors"; Immunity 33: pp. 375-386.
Cuende, et al (2015) "Monoclonal antibodies against GARP/TGF-β1 complexes inhibit the immunosuppressive activity of human regulatory T cells in vivo"; Sci Transl Med. 7(284):284ra56; pp. 1-13.
Dai et al., "Incomplete restoration of colony-stimulating factor 1 (CSF-1) function in CSF-1-deficient Csflop/Csflop mice by transgenic expression of cell surface CSF-1" Blood 103(3):1114-1123 (Feb. 1, 2004).

(56)             References Cited

OTHER PUBLICATIONS

Danos et al. (1988) "Safe and efficient generation of recombinant retroviruses with amphotropic and ecotropic host ranges"; PNAS 85: pp. 6460-6464.

Dao; et al. "Immunodeficient mice as models of human hematopoietic stem cell engraftment", Current Opinion in Immunol (1999), 11:532-537.

Das, et al (2016) "Microenvironment-dependent growth of preneoplastic and malignant plasma cells in humanized mice"; Nat Med. 22(11); pp. 1351-1357.

De Raeve and Vanderkerken, (2005), "The role of the bone marrow microenvironment in multiple myeloma"; Histol Histopathol. 20: pp. 1227-1250.

De Sauvage, F.J. et al. (1994) Stimulation of megakaryocytopoiesis and thrombopoiesis by the c-Mpl ligand, Nature 369:533-538.

Denning, et al (2001) "Deletion of the alpha(1,3)galactosyl transferase (GGTA1) gene and the prion protein (PrP) gene in sheep"; Nat Biotech;19; pp. 559-562.

Dennis Melvin B. (2002) "Welfare issues of genetically modified animals"; ILAR Journal, vol. 43, No. 2, pp. 100-109.

Denton PW, et al. (2012) "IL-2 receptor γ-chain molecule is critical for intestinal T-cell reconstitution in humanized mice"; Mucosal Immunol; 5(5); pp. 555-566.

Depaolo, et al: (2011) "Co-adjuvant effects of retinoic acid and IL-15 induce inflammatory immunity to dietary antigens"; *Nature. 471*; pp. 220-224.

Dewan et al., (2004), "Prompt tumor formation and maintenance of constitutive NF-κB activity of multiple myeloma cells in NOD/SCID/γcnull mice"; Cancer Sci. 95:564-568.

Dhodapkar, (2009), "Myeloid neighborhood in myeloma: Cancer's underbelly" Am J Hematol. 84: pp. 395-396.

Diminici et al. (2006) Minimal criteria for defining multipotent mesenchymal stromal cells, The International Society for Cellular Therapy position statement, Cytotherapy 8:315-317.

Doherty et al. (1999) "Infection of HIV-1 Transgenic Mice with Mycobacterium avium Induces the Expression of Infectious Virus Selectively from a Mac-1-Positive Host Cell Population"; The Journal of Immunology 163(3); pp. 1506-1515.

Drake, et al; (2012) "Engineering humanized mice for improved hematopoietic reconstitution"; *Cell Mol Immunol. 9(3)*; pp. 215-224.

Egeblad et al., (2010), "Tumors as organs: complex tissues that interface with the entire Organism"; Developmental cell 18: pp. 884-901.

Eisenbarth et al.; "Development and Characterization of a Human IL-7 Transgenic Humanized Mouse Model,"; iwhm2, 2nd International Workshop on Humanized Mice, Program & Abstract Book; Sint Olofskapel, Amsterdam, The Netherlands, Apr. 3-6, 2009, Abstract #19.

El-Ad et al. (2013) "viSNE enables visualization of high dimensional single-cell data and reveals phenotypic heterogeneity of leukemia"; Nat. Biotechnol. 31(6); pp. 545-552.

Epstein et al., (2005), "The SCID-hu myeloma model"; Methods Mol Med, 113: pp. 183-190.

Erta M. et al., "Interleukin-6, a major cytokine in the central nervous system"; Int J Biol Sci. 2012;8(9):1254-66. doi: 10.7150/ijbs.4679. Epub Oct. 25, 2012.

Extended European Search Report for EP Application No. 16157878.6 dated May 23, 2016.

Fattori et al., "IL-6 Expression in Neurons of Transgenic Mice Causes Reactive Astrocytosis and Increase in Ramified Microglial Cells but no Neuronal Damage," European Journal of D Neuroscience, 7: 2441-2449, 1995.

Fattori, et al., "Development of Progressive Kidney Damage and Myeloma Kidney in Interleukin-6 Transgenic Mice," Blood, 83(9): 2570-2579, 1994.

Felix, R. et al. (1990) Macrophage colony stimulating factor restores in vivo bone resorption in the op/op osteopetrotic mouse, Endocrinology 127:2592-2594.

Figueiredo-Pontes, et al (2021) "Improved hematopoietic stem cell transplantation upon inhibition of natural killer cell-derived interferon-gamma"; Stem Cell Reports, 16(8); pp. 1-5.

Fisher et al.; "Lymphoproliferative Disorders in an IL-7 Transgenic Mouse Line,"; Leukemia, 7(02): pp. 566-568; (1993).

Flavell, Richard A. "Tissue-resident T cells in a novel humanized mouse model" Presentation: CSH Meeting, Apr. 16, 2015; 23 pages.

Fonseca et al., (2002), "Genomic abnormalities in monoclonal gammopathy of undetermined significance" Blood 100: pp. 1417-1424.

Foss et al; (1995) "Frequent Expression of IL-7 Gene Transcripts in Tumor Cells of Classical Hodgkin's Disease"; *American Journal of Pathology, 146(1)*: pp. 33-39.

Fox, N., et al. (2002) Thrombopoietin expands hematopoietic stem cells after transplantation, J Clin Invest 110, 389-3894.

Freeden Jeffry et al.; (1995) "Lymphopenia in Interleukin (IL)-7 Gene-deleted Mice Identifies IL-7 as a Nonredundant Cytokine"; J. Exp. Med. 181; pp. 1519-1526.

Fry et al. (2006) "IL-7 comes of age"; Blood, 107(1); pp. 2587-2588.

Fry et al., (2001) "A potential role for interleukin-7 in T-cell homeostasis"; Blood, 97: 2983-2990.

Fry et al., (2005) "The Many Faces of IL-7: From Lymphopoiesis to Peripheral T Cell Maintenance"; Journal of Immunology, 174: pp. 6571-6576.

Fry, et al., (2002) "Interleukin-7: from bench to clinic"; Blood, 99(11); pp. 3892-3904.

Fukuchi, Y., et al., (1998) "Cytokine dependent growth of human TF-1 leukemic cell line in human GMCSF and IL-3 producing transgenic SCID mice"; *Leukemia Research, vol. 22*; pp. 837-843.

Galán J.E. & Curtiss, R. (1991) "Distribution of the invA, -B, -C, and -D genes of S. thyphimurium among other *Salmonella*. Serovars: invA mutants of *Salmonella* typhi are deficient for entry into mammalian cells"; Infect. Immun. 59(9): pp. 2901-2908.

Garcia, Sylvie, et al; "Humanized mice: Current states an perspectives"; Immunology Letters, Elsevier BV, NL, vol. 146, No. 1-2; Aug. 30, 2012; pp. 1-7; XP002681730.

Geiselhart et al., (2001) "IL-7 Administration Alters the CD4: CDS Ratio, Increases T Cell Numbers, and Increases T Cell Function in the Absence of Activation"; *The Journal of Immunology, 166*: 3019-3027.

Goldman et al. (2004) "Transgenic animals in medicine: integration and expression of foreign genes, theoretical and applied aspects"; *Med Sci Monit, vol. 10, No. 11*; pp. RA274-285.

Goldman; et al. "BMP4 regulates the hematopoietic stem cell niche", Blood (Nov. 2009), 114(20):4393-4401.

Goodwin et al.; (1989) "Human interleukin 7: Molecular cloning and growth factor activity on human and murine B-lineage cells"; *Proc. Natl. Acad. Sci. USA, 86*; pp. 302-306.

Gorantla; et al. "Human Immunodeficiency Virus Type 1 Pathobiology Studied in Humanized BALB/c-Rag2-/-Yc-/- Mice", Journal of Virology (Mar. 2007), 81(6):2700-2712.

Goya et al., (2003) "Sustained interleukin-6 signalling leads to the development of lymphoid organ-like structures in the lung"; *Journal of Pathology, 200*: pp. 82-87.

Greenblatt, et al. (2012) "Graft versus host disease in the bone marrow, liver and thymus humanized mouse model"; PLoS One 7(9); e44664.

Greiner; et al. "Improved Engraflment of Human Spleen Cells in NOD/LtSz-scid/scid Mice as Compared with C. B-17-scid/scid Mice", American Journal of Pathology (Apr. 1995), 146(4):888-902.

Groen, R. W. J., et al; "Reconstructing the human hematopoietic niche in immunodeficient mice: opportunities for studying primary multiple myeloma"; *BLOOD, vol. 120, No. 3*, May 31, 2012; pp. e9-e16, XP055113167.

Guimond et al.; "Cytokine Signals in T-Cell Homeostasis"; *J. Immunother, 28*; (2005); pp. 289-294.

Haley, (2003), "Species differences in the structure and function of the immune System"; Toxicology 188: pp. 49-71.

Hao et al., (2012), "Macrophages in tumor microenvironments and the progression of tumors"; *Clinical & developmental immunology 2012*; 948098; 11 pages.

(56)                    References Cited

OTHER PUBLICATIONS

Hayakawa J., et al., (2009), "Busulfan produces efficient human cell engraftment in NOD/LtSz-Scid IL2Rgamma(null) mice"; Stem Cells, 27(1): pp. 175-182.

Hayday Adrian and Viney Joanne L.; (2000) "The ins and outs of body surface immunology"; Science 290(5489):97-100.

Heinrich et al., (19900 "Interleukin-6 and the acute phase response"; *Biochem. J. 265*: 621-636.

Herndler-Brandstetter D. et al: (2017) "Humanized mouse model supports development, function, and tissue residency of human natural killer cells"; Proc Natl Acad Sci U S A. 114(45); pp. E9626-E9634.

Hideshima et al., (2007), "Understanding multiple myeloma pathogenesis in the bone marrow to identify new therapeutic targets"; Nat Rev Cancer. 7: pp. 585-598.

Hiramatsu, Hidefumi, et al; (2003) "Complete reconstitution of human lymphocytes from cord blood CD34+ cells using the NOD/SCID/γc$^{null}$ mice model"; *Blood, vol. 102, No. 3*; Aug. 1, 2003: pp. 873-880.

Hirano et al., (1985) "Purification to homogeneity and characterization of human B-cell differentiation factor (BCDF or BSFp-2)"; *Proc. Natl. Acad. Sci. USA, 82*: pp. 5490-5494.

Hirano et al., (1986) "Complementary DNA for a novel human interleukin (BSF-2) that induces B lymphocytes to produce immunoglobulin"; *Nature, 324*: pp. 73-76.

Hirano et al., (1990) "Biological and clinical aspects of interleukin 6"; *Immunology, 11*: pp. 443-449.

Hirota et al., (1995) "Continuous activation of gp130, a signal-transducing receptor component for interleukin 6-related cytokines, causes myocardial hypertrophy in mice" *Proc. Natl. Acad. Sci. D USA, 92*: pp. 4862-4866.

Hofer; et al. "RAG2-/-γc-/-Mice Transplanted with CD34+ Cells from Human Cord Blood Show Low Levels of Intestinal Engraftment and Are Resistant to Rectal Transmission of Human Immunodeficiency Virus", Journal of Virology (Dec. 2008), 82(24):12145-12153.

Hofker Marten H., et al., *Transgenic mouse methods and protocols, Methods in molecular biology, vol. 209* (2002-2003), p. 51-58.

Holyoake et al. (1999) "Functional differences between transplantable human hematopoietic stem cells from fetal liver, cord blood, and adult marrow"; Exp Hematol. 27(9): pp. 1418-1427.

Houdebine Louis-Marie (2009) "Methods to Generate Transgenic Animals"; *Genetic Engineering in Livestock: New Applications and Interdisciplinary Perspectives*; pp. 31-48.

Houdebine, Louis-Marie (2007) "Transgenic animal models in biomedical research"; *Methods in Molecular Biology, vol. 360*; pp. 163-202.

Hu, Z. et al; "Macrophages prevent human red blood cell reconstitution in immunodeficient mice"; BLOOD, vol. 118, No. 22; Nov. 24, 2011; pp. 5938-5946.

Huntington et al., (2009), "IL-15 trans-presentation promotes human NK cell development and differentiation in vivo"; Journal of experimental medicine 206(1), pp. 25.

Huo; et al. "Humanized Mouse Model of Cooley's Anemia", J. Biol. Chem (Feb. 2009), 284(8):4889-4896.

Huston et al., (1988), "Protein engineering of antibody binding sites: recovery of specific activity in an anti-digoxin single-chain Fv analogue produced in *Escherichia coli*"; Proc. Natl. Acad. Sci. USA 85(16): pp. 5879-5883.

Inagaki, et al (2000) "SHPS-1 regulates integrin-mediated cytoskeletal reorganization and cell motility"; EMBO J. 19(24) pp. 6721-6731.

Irvine et al., "Colony-stimulating factor-1 (CSF-1) delivers a proatherogenic signal to human macrophages" Journal of Leukocyte Biology, 85:278-288 (Feb. 2009).

Ishikawa et al. (2005), "Development of functional human blood and immune systems in NOD/SCID/IL2 receptor {gamma} chain-(null) mice"; Blood 106(5):1565-73. Epub May 26, 2005.

Ito et al., "NOD/SCID/gamma(c)(null) mouse: an excellent recipient mouse model for engraftment of human cells" *Blood 100(9)*; Nov. 1, 2002; pp. 3175-3182.

Ito, et al (2013) "Establishment of a human allergy model using human IL-3/GM-CSF-transgenic NOG mice"; The Journal of Immunology 191(6); pp. 2890-2899.

IWHM2 2nd International Workshop on Humanized Mice, Colorado State University, Program & Abstract Book. (Apr. 3-6, 2009), Sint Olofskapei/Amsterdam, NL.

Jacob et al: (2010) "Gene targeting in the rat: advances and opportunities"; *Trends Genet. 26(12)*:510-518. doi: 10.1016/j.tig. 2010.08.006. Epub Oct. 1, 2010.

Jacobs et al., "IL-7 is Essential for Homeostatic Control ofT Cell Metabolism In Vivo," The Journal of Immunology, 184: 3461-3469, 2010.

Jimenez-Diaz et al. (2009) "Improved murine model of malaria using Plasmodium falciparum competent strains and non-myelodepleted NOD-scid IL2Rgnull mice engrafted with human erythrocytes"; Antimicrob Agents Chemother 53: pp. 4533-4536.

Jones et al (1995) "Antimicrobial Chemotherapy of Human Infection due to Listeria Monocytogenes"; Eur. J. Clin. Microbial. Infect. Dis., 14(3); pp. 165-175.

Kalberer, et al (2003) "Human NK cell development in NOD/SCID mice receiving grafts of cord blood CD34+ cells"; Blood 102(1); pp. 127-135.

Kalueff A.V. et al., (2004) "Intranasal administration of human IL-6 increases the severity of chemically induced seizures in rats"; *Neurosci Lett. 365(2)*:106-110.

Kamel-Reid and Dick, (1988) "Engraftment of immune-deficient mice with human hematopoietic stem cells"; Science 242 (4886):1706-1709.

Kandalaft et al., (2011) "Angiogenesis and the tumor vasculature as antitumor immune modulators: the role of vascular endothelial growth factor and endothelin"; Curr Top Microbiol Immunol.; 344: 129-48.

Kang et al., (1999) "Defective Development of y/o T Cells in Interleukin 7 Receptor-deficient Mice is Due to Impaired Expression of T Cell Receptor y Genes" *J. Exp. Med., 190(7)*: 973-982.

Katano, I. et al; (2015) "Predominant development of mature and functional human NK cells in a novel human IL-2-producing transgenic NOG mouse"; *Journal of Immunology, 194(7)*: pp. 3513-3525.

Kaufmann et al., (2004), "Both IGH translocations and chromosome 13q deletions are early events in monoclonalgammopathy of undetermined significance and do not evolve during transition to multiple myeloma" Leukemia. 18: pp. 1879-1882.

Kaushansky, et al (2014) "Of men in mice: the success and promise of humanized mouse models for human malaria parasite infections"; Cellular Microbiology, vol. 16, No. 5; pp. 602-611.

Kaushansky, K. (1998) "Thrombopoietin", N Engl J Med 339: pp. 746-754.

Kaushansky, K. (2005) "The molecular mechanisms that control thrombopoiesis", J Clin Invest 115: pp. 3339-3347.

Kaushansky, K. (2008) "Historical review: megakaryopoiesis and thrombopoiesis", Blood 111: pp. 981-986.

Kaushansky, K. et al. (1994) "Promotion of megakaryocyte progenitor expansion and differentiation by the c-Mpl ligand thrombopoietin", Nature 369: pp. 568-571.

Keefer (2015) "Artificial cloning of domestic animals"; PNAS 112; pp. 8874-8878.

Keller et al., (1996) "Molecular and Cellular Biology of Interleukin-6 and its Receptor"; *Frontiers in Bioscience, 1*: 340-357.

Kieper et al., (2002) "Overexpression of Interleukin (IL)-7 Leads to IL-15-independent Generation of Memory Phenotype CD+T Cells"; *J. Exp. Med., 195(12)*: 1533-1539.

Kieran Seay et al; (2015) In Vivo Activation of Human NK Cells by Treatment with an Interleukin-15 Superagonist Potently Inhibits Acute InVivo HIV-1 Infection in Humanized Mice; Journal of Virology, vol. 89. No. 12; pp. 6264-6274.

Kim et al., (2011) "Seeing is Believing: Illuminating the Source of In Vivo Interleukin-7"; *Immune Network, 11(1)*: pp. 1-7.

Kim, D. K., et al., (1998) "Engraftment of human myelodysplastic syndrome derived cell line in transgenic severe combined immunodeficient (TG-SCID) mice expressing human GM-CSF and IL-3"; *European Journal of Haematology, vol. 61*; pp. 93-99.

(56)                    References Cited

OTHER PUBLICATIONS

Kinoshita Ichiro, et al (2008) "Molecular pathophysiology of lung cancer-identification of lung cancer stem cells"; Nippon Rinsho, vol. 66, Suppl 6; pp. 95-99 (w/partial English translation).

Kirito, K. et al. (2003) "Thrombopoietin stimulates Hoxb4 expression: an explanation for the favorable effects of TPO on hematopoietic stem cells"; *Blood 102*:3172-3178.

Kirma et al., "Overexpression of the Colony-Stimulating Factor (CSF-1) and/or Its Receptor c-fms in Mammary Glands of Transgenic Mice Results in Hyperplasia and Tumor Formulation" Cancer Research, 64:4162-4170 (Jun. 15, 2004).

Kishimoto, Tadamitsu, (1989) "The Biology of Interleukin-6"; *Blood, 74(1)*: pp. 1-10.

Kishimoto, Tadamitsu, (2010). "IL-6: from its discovery to clinical applications"; *International Immunology, 22(5)*: pp. 347-352.

Kondo; et al. "Lymphocyte development from hematopoietic stem cells", Current Opn Gen & Dev (2001), 11:520-526.

Kosco-Vilbois; et al. "A mightier mouse with human adaptive immunity", Nature Biotechnology (Jun. 2004), 22 (6):684-685.

Kovalchuk et al., (2002) "IL-6 transgenic mouse model for extraosseous plasmacytoma" *PNAS, 99(3)*: pp. 1509-1514.

Kraus et al. (2010), "A more cost effective and rapid high percentage germ-line transmitting chimeric mouse generation procedure via microinjection of 2-cell, 4-cell, and 8-cell embryos with ES and iPS cells" Genesis 48(6): pp. 394-399.

Kuehl and Bergsagel, (2002), "Multiple myeloma: evolving genetic events and host interactions"; Nat Rev Cancer. 2(3): pp. 175-187.

Kukreja et al., (2006) "Enhancement of clonogenicity of human multiple myeloma by dendritic cells", J Exp Med. 203(8): pp. 1859-1865.

Kuruvilla; et al, "Dengue virus infection and immune response in humanized RAG2-1-yc-1-(RAG-hu) mice", Virology (2007), 369:143-152.

Kuter, D.J. & Rosenberg, R.D. (1995) "The reciprocal relationship of thrombopoietin (c-Mpl ligand) to changes in the platelet mass during busulfan-induced thrombocytopenia in the rabbit", *Blood 85*: pp. 2720-2730.

Landgren et al., (2009), "Monoclonal gammopathy of undetermined significance (MGUS) consistently precedes multiple myeloma: a prospective study"; Blood 113(22): pp. 5412-5417.

Lapidot et al., (1992) "Cytokine stimulation of multilineage hematopoiesis from immature human cells engrafted in SCID mice", Science 255(5048):1137-41.

Lebrec Herve, et al: "Homeostasis of human NK cells is not IL-15 dependent"; J Immunol. 191(11): Dec. 1, 2013; pp. 5551-5558. doi: 10.4049/jimmunol.1301000. Epub Nov. 1, 2013.

Lee, et al (2018) "Differences between immunodeficient mice generated by classical gene targeting and CRISPR/Cas9-mediated gene knockout"; Transgenic Research, vol. 27, No. 3; pp. 241-251.

Legrand et al., (2011) "Functional CD47/signal regulatory protein alpha (SIRP(alpha)) interaction is required for optimal human T- and natural killer-(NK) cell homeostasis in vivo", Proc Natl Acad Sci USA 108(32): pp. 13224-13229.

Legrand; et al. "Experimental Models to Study Development and Function of the Human Immune System in Vivo", The Journal of Immunology (2006), 176: 2053-2058.

Legrand; et al. "Humanized Mice for Modeling Human Infectious Disease: Challenges, Progress, and Outlook", *Cell Host & Microbe, vol. 6*, No. 1; (Jul. 2009); pp. 5-9. XP00258476.

Lemay L.G. et al: (1990) "Role of interleukin 6 in fever in rats"; *Am J Physiol. 258(3 Pt 2)*: R798-803.

Lepus, et al (2009) "Comparison of Human Fetal Liver, Umbilical Cord Blood, and Adult Blood Hematopoietic Stem Cell Engraftment in NOD-scid/γc–/–, Balb/c-Rag1–/–γc–/–, and C.B-17-scid/bg Immunodeficient Mice"; Hum Immunol. 70(10): pp. 790-802.

Libby; et al. "Humanized nonobese diabelic-scid IL2ry null mice are susceptible to lethal *Salmonella typhi* infection", PNAS (Aug. 2010), 107(35):15589-15594.

Lie and Petropoulos (1998) "Advances in quantitative PCR technology: 5' nuclease assays"; Curr. Opin. Biotechnology 9(1); pp. 43-48.

Liton et al., (2005), "Specific Targeting of Gene Expression to a Subset of Human Trabecular Meshwork Cells Using the Chitinase 3-Like 1 Promoter"; Invest Ophthalmol Vis Sci.46(1):183-90.

Lok, S. et al. (1994) Cloning and expression of murine thrombopoietin cDNA and stimulation of platelet production in vivo, Nature 369:565-568.

Lombard-Platet et al., (1995) "Expression of Functional MHC Class II Molecules by a Mouse Pro-B Cell Clone"; *Developmental Immunology*, 4: 85-92.

Lu et al. (2009) "Epitope-tagged receptor knock-in mice reveal that differential desensitization of alpha2-adrenergic responses is because of ligand-selective internalization."; J. Bioi. Chem., vol. 284(19), 13233-13243.

Luo; et al., "Knock-in mice with chimeric human/murine p53 gene develop normally and show wild-type p53 responses to DNA damaging agents: a new biomedical research tool", Oncogene (2001), 20:320-328.

Lupton et al., (1990) "Characterization of the Human and Murine IL-7 Genes" *The Journal of Immunology, 144(9)*: 3592-3601.

Ma et al., (2006), "Diverse functions of IL-2, IL-15, and IL-7 in lymphoid homeostasis"; Annu Rev Immunol. 24: 657-79.

Macbride Megan M.; "Meeting report: International Workshop on Humanized Mice 5"; Mar. 8, 2016; XP002758867.

Macchiarini, et al. "Humanized mice: are we there yet?"; Journal of Experimental Medicine, vol. 202, No. 10; (Nov. 2005); pp. 1307-1311; XP002559426.

Madan A., et al (1995) "Regulated basal, inducible, and tissue-specific human erythropoietin gene expression in transgenic mice requires multiple cis DNA sequences"; Blood, vol. 85, No. 10; pp. 2735-2741.

Mahajan et al., "Homeostasis of T Cell Diversity," Cellular & Molecular Immunology, 2(1): 1-10, 2005.

Maione et al., (1998) "Coexpression of IL-6 and soluble IL-6R causes nodular regenerative hyperplasia and adenomas of the liver"; *The EMBO Journal, 17(19)*: 5588-5597.

Majumder et al. (1996) "Xenogeneic expression of human stem cell factor in transgenic mice mimics codominant c-kit mutations", Blood 87(8):3203-3211.

Maksimenko et al (2013) "Use of transgenic animals in biotechnology: prospects and problems"; *Acta Naturae, vol. 5, No. 1*; pp. 33-46.

Manz Markus M., et al.; "Human-Hemato-Lymphoid-System Mice: Opportunities and Challenges", Immunity, vol. 26, No. 5; (May 2007); pp. 537-541.

Manz; et al. "Renaissance for mouse models of human hematopoiesis and immunobiology", Nature Immun. (Oct. 2009), 10(10):1039-1042.

Mason; et al. "Alcohol Exacerbates Murine Pulmonary Tuberculosis", Infection and Immunity (May 2004), 72 (5):2556-2563.

Mazurier; et al. "A Novel Immunodeficient Mouse Model-RAG2 X Common Cytokine Receptor y Chain Double Mutants-Requiring Exogenous Cytokine Administration for Human Hematopoietic Stem Cell Engraftment", Journal of Interferon and Cytokine Research (1999), 19:533-541.

Mazzucchelli et al., (2007) "Interleukin-7 receptor expression: intelligent design"; *Nature, 7*: 144-154.

Mazzucchelli et al., (2009) "Visualization and Identification of IL-7 Producing Cells in Reporter Mice," *PLOS ONE, 4(11)*: p. e7637.

Mcburney et al. (1994) "Murine PGK-1 promoter drives widespread but not uniform expression in transgenic mice"; Dev Dyn. 200(4):278-93.

Mccune et al., (1988) "The SCID-hu mouse: murine model for the analysis of human hematolymphoid differentiation and function"; Science 241(4873):1632-1639.

Mcdermott et al. (2010) "Comparison of human cord blood engraftment between immunocompromised mouse strains"; Blood 116(2); pp. 193-200.

Mertsching et al., (1995) "IL-7 transgenic mice: analysis of the role of IL-7 in the differentiation of thymocytes in vivo and in vitro"; *International Immunology, 7(3)*: 401-414.

(56)　　　　　　References Cited

OTHER PUBLICATIONS

Mestas & Hughes, (2004) "Of mice and not men: differences between mouse and human immunology"; J Immunol. 172(5):2731-2738.
Meyer et al. (2010) "Gene targeting by homologous recombination in mouse zygotes mediated by zinc-finger nucleases"; Proc Natl Acad Sci U S A. 107(34):15022-15026. doi: 10.1073/pnas. 1009424107. Epub Aug. 4, 2010.
Miller et al. (1985) "Generation of helper-free amphotropic retroviruses that transduce a dominant-acting, methotrexate-resistant dihydrofolate reductase gene"; Mol Cell Biol. 5(3):431-437.
Miller et al. (1986) "Redesign of retrovirus packaging cell lines to avoid recombination leading to helper virus production"; Mol Cell Biol. 6(8):2895-2902.
Mittrucker; et al. "Cutting Edge: Role of B Lymphocytes in Protective Immunity Against Salmonella typhimurium Infection", J. Immunol. (2000), 164:1648-1652.
Miyakawa et al.; (2004) "Establishment of a new model of human multiple myeloma using NOD/SCID/y$_c^{null}$ (NOG) mice"; Biochem. Biophys. Res. Comm., vol. 313; pp. 258-262.
Mlecnik Bernhard, et al; (2014) "Functional network pipeline reveals genetic determinants associated with in situ lymphocyte proliferation and survival of cancer patients"; Sci Transl Med. 6:228ra37.
Moreadith et al. (1997) "Gene targeting in embryonic stem cells: the new physiology and metabolism"; J. Mol. Med. 75(3); pp. 208-216.
Moreno et al. (2006) "The course of infections and pathology in immunomodulated NOD/LtSz-SCID mice inoculated with Plasmodium falciparum laboratory lines and clinical isolates"; Int. J. Parasitol. 36:361-369.
Mosier et al., (1988) "Transfer of a functional human immune system to mice with severe combined immunodeficiency"; Nature 335(6187):256-259.
Motz and Coukos, (2013) "Deciphering and reversing tumor immune suppression"; Immunity 39(1):61-73.
Mullins (1996) "Transgenesis in the rat and larger mammals"; J Clin Invest,97; pp. 1557 15-60.
Munitic et al. (2004) "Dynamic regulation of IL-7 receptor expression is required for normal thymopoiesis"; Blood, 104: 4165-4172.
Munoz et al., "Constraints to Progress in Embryonic Stem Cells from Domestic Species," Stem Cell Rev. and Rep., 5:6-9, 2009.
Murphy et al. (1993) "Antitumor Effects of Interleukin-7 and Adoptive Immunotherapy on Human Colon Carcinoma Xenografts"; J. Clin. Invest., 92: 1918-1924.
Murphy, D. MFA: the turducken of alleles*, Wellcome Trust Advanced Course: Genetic Manipulation of ES Cells, 76 pages (2010).
Murphy, D., BAC-based Modifications of the Mouse Genome: The Big and the Backward, Wellcome Trust Advanced Course: Genetic Manipulation of ES Cells, 58 pages (2009).
Murray; et al. "Thrombopoietin mobilizes CD34+ cell subsets into peripheral blood and expands multilineage progenitors in bone marrow of cancer patients with normal hematopoiesis", Exp Hematol (Mar. 1998), 26(3):207-216.
Nagy et al. (1990) "Embryonic stem cells alone are able to support fetal development in the mouse"; Development. 110(3):815-21.
Naka et al., (2002) "The paradigm of IL-6: from basic science to medicine"; Arthritis Research, 4(3): S233-S242.
Nelson and Bissell, (2006) "Of extracellular matrix, scaffolds, and signaling: tissue architecture regulates development, homeostasis, and cancer"; Annu Rev Cell Dev Biol. 22:287-309.
NEVUS (2016) Biologicals—a Bio-Techne Brand, "Human IL-6 Protein 5 μg", NBP2-34901 (4 pages).
Nichterlein et al. (1991) "Effect of Various Antibiotics on Listeria monocytogenes Multiplying in L 929 Cells"; Infection 19: Supplement 4; pp. S234-S238.
Nicolini; et al. "NOD/SCID mice engineered to express human IL-3, GM-CSF and Steel factor constitutively mobilize engrafted human progenitors and compromise human stem cell regeneration", Leukemia (2004), 18:341-347.

Niemann et al., "Transgenic farm animals: present and future," Rev. Sci. Tech. Off. Int. Epiz., 24(1):285-298, 2005.
Nishimura, et al; (2000) "Differential Roles of Interleukin 15 mRNA Isoforms Generated by Alternative Splicing in Immune Responses In Vivo"; J Exp Med. 191(1); pp. 157-170.
Nochi T, et al. (2013) "Cryptopatches are essential for the development of human GALT"; Cell Rep; 3(6); pp. 1874-1884.
Northemann, et al (1989) "Structure of the Rat Interleukin 6 Gene and Its Expression in Macrophage-derived Cell" J Biol Chem. 264(27):16072-16082.
O'Connell et al., (2010) "Lentiviral Vector Delivery of Human Interleukin-7 (hIL-7) to Human Immune System (HIS) Mice Expands T Lymphocyte Populations"; PLOS ONE, 5(8): 1-10.
Palm NW, et al. (2014) "Immunoglobulin A coating identifies colitogenic bacteria in inflammatory bowel disease"; Cell; 158(10); pp. 1000-1010.
Papanicolaou Dimitris et al., (1998) "The Pathophysiologic Roles of Interleukin-6 in Human Disease" Ann Intern Med. 128: 127-137.
Paris DB and Stout TA (2010) "Equine embryos and embryonic stem cells: defining reliable markers of pluripotency"; Theriogenology 74(4); pp. 516-524. (from 013RU OA rec'd Nov. 30, 2018).
Patil et al. (2011) "Transgenic animals and drug development: A review"; Indian Journal of Public Health research & Development, vol. 2, No. 1; pp. 106-109.
Pear et al. (1993) "Production of high-titer helper-free retroviruses by transient transfection"; Proc Natl Acad Sci U S A. 90(18):8392-8396.
Pearson et al. (2008), "Creation of "Humanized" Mice to Study Human Immunity"; Curr. Protoc. Immunol. 81: pp. 1-15.
Pek et al., (2011) "Characterization and IL-15 dependence of NK cells in humanized mice"; Immunobiology 216(1-2):218-24.
Peters et al., (1996) "The Function of the Soluble Interleukin 6 (IL-6) Receptor In Vivo: Sensitization of Human Soluble IL-6 Receptor Transgenic Mice Towards IL-6 and Prolongation of the Plasma D Half-life of iL-6"; J. Exp. Med. 183:1399-1406.
Pierfrancesco Tassone, et al: "A clinically relevant SCID-hu in vivo model of human multiple myeloma"; Blood. American Society Of Hematology. US. vol. 106. no. 2; Jul. 15, 2005; pp. 713-716; XP002633148.
Pixley et al., "CSF-1 regulation of the wandering macrophage: complexity in action" Trends in Cell Biology, 14(11):628-638 (Nov. 2004).
Pleiman et al., (1991) "Organization of the Murine and Human Interleukin-7 Receptor Genes: Two mRNAs Generated by Differential Splicing and Presence of a Type 1-Interferon-Inducible Promoter"; Molecular and Cellular Biology 11(6): 3052-3059.
Polejaeva et al (2000) "Cloned pigs produced by nuclear transfer from adult somatic cells"; Nature 407; pp. 86-90.
Pollard, Jeffrey W.; "Tumour-educated macrophages promote tumour progression and metastasis"; Nature Reviews, 4; (Jan. 2004); pp. 71-78.
Poueymirou et al. (2007) "F0 generation mice that are essentially fully derived from the donor gene-targeted ES cells allowing immediate phenotypic analyses"; Nat Biot 25(1):91-99.
Prelle et al., "Pluripotent Stem Cells—Model of Embryonic Development, Tool for Gene Targeting, and Basis of Cell Therapy," Anal. Histol. Embryol. 31; (2002); pp. 169-186.
Qian and Pollard, (2010) "Macrophage diversity enhances tumor progression and metastasis": Cell 141(1):39-51.
Qian, H. et al. (2007) Critical role of thrombopoietin in maintaining adult quiescent hematopoietic stem cells, Cell Stem Cell1 :671-684.
Rämer Patrick C. et al; (2011) "Mice with human immune system components as in vivo models for infections with human pathogens"; Immunol Cell Biol. 89(3):408-16. doi: 10.1038/icb.2010. 151. Epub Feb. 8, 2011.
Rathinam et al., "Efficient differentiation and function of human macrophages in humaized CSF-1 mice" Blood, 118(11):3119-3132 (Sep. 15, 2011).
Rathinam et al., "Efficient differentiation and function of human macrophages in humaized CSF-1 mice" Blood, 118(11):3119-3128 (Sep. 15, 2011)—Supplemental Figures.
Raulet, (2006) "Missing self recognition and self tolerance of natural killer (NK) cells"; Seminars in immunology 18(3):145-50.

(56)         References Cited

OTHER PUBLICATIONS

Repass et al., (2009) "IL7-hCD25 and IL7-Cre BAC transgenic mouse lines: New tools for analysis of IL-7 expressing cells"; *Genesis, 47(4)*: 281-287.

Rich et al., (1993) "Cutaneous Lymphoproliferation and Lymphomas in Interleukin 7 Transgenic Mice"; *J. Exp. Med. 177*: 305-316.

Rieger et al.; "Hematopoietic Cytokines Can Instruct Lineage Choice"; *Science, 325*; (Jul. 10, 2009); pp. 217-218.

Ring, Aaron M. et al; (2012) "Mechanistic and structural insight into the functional dichotomy between IL-2 and IL-15"; *Nat Immunol. 13(12)*: pp. 1187-1195.

Rohrschneider, L.R. et al. (1997) "Growth and differentiation signals regulated by the MCSF receptor", Mol. Reprod. Dev. 46:96-103.

Rongvaux A. et al: (2012) "MISTRG: a novel humanised mouse model to study human hematopoiesis and myeloid development and function in vivo"; Immunology, vol. 137, No. 1, Suppl. 1; pp. 184.

Rongvaux Anthony et al: "Development and function of human innate immune cells in a humanized mouse model"; Nature Biotechnology. vol. 32. No. 4; (Apr. 2014) pp. 364-372.

Rongvaux et al., (2013), "Human hemato-lymphoid system mice: current use and future potential for medicine"; Annu Rev Immunol. 31: 635-674. doi: 10.1146/annurev-immunol-032712-095921. Epub Jan. 16, 2013.

Rongvaux, A., et al.; "Human thrombopoietin knockin mice efficiently support human hematopoiesis in vivo", PNAS, vol. 108, No. 6; (Feb. 2011); pp. 2378-2383.

Rongvaux, Anthony; "Improvement of human-hemato-lymphoid-system mice: the human Thrombopoietin knock-in mouse"; IWHM2 2nd International Workshop on Humanized Mice, PowerPoint Presentation; Apr. 3-6, 2009; Sint Olofskapei/Amsterdam, NL; pp. 1-20.

Rongvaux; "Human Thrombopoietin knockin mice efficiently support human hematopoiesis", Flavell Lab, Yale University (ASH—Dec. 6, 2010).

Roychowdhury Sameek, et al; (2005) "IL-15 but not IL-2 rapidly induces lethal xenogeneic graft-versus-host disease"; Blood 106(7):2433-5. Epub Jun. 23, 2005.

Ryan et al., "Rescue of the colony-stimulating factor 1 (CSF-1)-nullizygous mouse (Csflop/Csflop) phenotype with CSF-1 transgene and identification of sites of local CSF-1 synthesis" Blood, 98(1):74-84 (Jul. 2001).

Rybchin C. N., "Principles of Genetic Engineering"; Saint-Petersburg, Publisher SPbGTU, 2002; p. 411-413.

Saha et al; (2009); "Technical challenges in using human induced pluripotent stem cells to model disease"; Cell Stem Cell.5(6); pp. 584-595.

Samaridis et al., (1991) "Development of lymphocytes in intereleukin 7-transgenic mice"; *Eur. J. Immunol. 21*: 453-460.

Sanmamed, et al (2015) "Nivolumab and Urelumab Enhance Antitumor Activity of Human T Lymphocytes Engrafted in Rag2-/–IL2Rγnull Immunodeficient Mice"; Cancer Res. 75(17); pp. 3466-3478.

Sanmamed, et al (2016) "Defining the optimal murine models to investigate immune checkpoint blockers and their combination with other immunotherapies"; Ann Oncol. 27(7); pp. 1190-1198.

Sarrazin et al., "MafB Restricts M-CSF-Dependent Myeloid Commitment Divisions of Hematopoietic Stem Cells" Cell, 138:300-313 (Jul. 24, 2009).

Sawamura D. et al., (1998) "Induction of keratinocyte proliferation and lymphocytic infiltration by in vivo introduction of the IL-6 gene into keratinocytes and possibility of keratinocyte gene therapy for inflammatory skin diseases using IL-6 mutant genes"; *J Immunol. 161(10)*:5633-5639.

Schluns et al.; "Interleukin-7 mediates the homeostasis of naive and memory COST cells in vivo"; Nature Immunology, 1(5); (2000); pp. 426-432.

Schorpp et al. (1996) "The human ubiquitin C promoter directs high ubiquitous expression of transgenes in mice"; Nucleic Acids Res. 24(9):1787-1788.

Scudellari, Megan; "The innate debate over HSCs"; *Nature Reports Stem Cells*; (published online Aug. 6, 2009 / doi: 10.1038/stemcells.2009.103). 1 page.

Selsby et al (2015) "Porcine Models of Muscular Dystrophy"; *ILAR Journal, vol. 56, No. 1* pp. 116-126.

Semenza Gregg L., et al; "Cell-type-specific and hypoxia-inducible expression of the human erythropoietin gene in transgenic mice"; GENETICS, vol. 88; (Oct. 1991); pp. 8725-8729.

Semenza, G. L. et al; "Polycythemia in transgenic mice expressing the human erythropoietin gene"; *Proceedings of The National Academy of Sciences, vol. 86, No. 7*; (Apr. 1989); pp. 2301-2305.

Setty Mala, et al: (2015) "Distinct and Synergistic Contributions of Epithelial Stress and Adaptive Immunity to Functions of Intraepithelial Killer Cells and Active Celiac Disease"; Gastroenterology 149(3):681-91.e10. doi: 10.1053/j.gastro.2015.05.013. Epub May 19, 2015.

Shalapour et al. (2010) "Commensal microflora and interferon-[gamma] promote steady-state interleukin-7 production in vivo"; *European Journal of Immunology, 40(9)*; pp. 2391-2399.

Sherr, C.J. et al. (1988) "Macrophage colony-stimulating factor, CSF-1, and its proto-oncogene-encoded receptor"; Cold Spring Harb. Symp. Quant. Biol. 53 Pt 1:521-530.

Shinobara et al. (2007) "Active integration: new strategies for transgenesis"; *Transgenic research, vol. 16*, pp. 333-339.

Shultz et al., (2000) "NOD/LtSz-Rag1null mice: an immunodeficient and radioresistant model for engraftment of human hematolymphoid cells, HIV infection, and adoptive transfer of NOD mouse diabetogenic T cells"; J Immunol. 164(5):2496-2507.

Shultz L D et al; "Humanized mice in translational biomedical research"; *The Journal of Immunology. Nature Pub. Group. GB, vol. 7. No. 2*; (Feb. 2007) pp. 118-130. XP002493022.

Shultz, Leonard D., et al; "Humanized mice for immune system investigation: progress, promise and challenges"; Nature Reviews Immunology, vol. 12, No. 11; (Nov. 1, 2012); pp. 786-798. XP055064740.

Shultz; et al."Human Lymphoid and Myeloid Cell Development in NOD/LtSz-scid IL2Ry null Mice Engrafted with Mobilized Human Hempoietic Stem Cells", J Immunol (2005), 174:6477-6489.

Silva et al. (2011) "IL-7 Contributes to the Progression of Human T-cell Acute Lymphoblastic Leukemias"; *Cancer Research, 71 (14)*; pp. 4780-4789.

Skjot et al. (2002) "Epitope mapping of the immunodominant antigen TB10.4 and the two homologous proteins TB10.3 and TB12.9, which constitute a subfamily of the esat-6 gene family"; Infect. Immun. 70:5446-5453.

Socolovsky, M. et al. (1998) "Cytokines in hematopoiesis: specificity and redundancy in receptor function"; Adv. Protein Chem. 52:141-198.

Soderquest et al. (2011) "Monocytes control natural killer cell differentiation to effector phenotypes," Blood 117(17):4511-4518. doi: 10.1182/blood-2010-10-312264. Epub Mar. 9, 2011.

Sohn B; et al. "Expression and characterization of bioactive human thrombopoietin in the milk of transgenic mice", DNA Cell Biol (Nov. 1999), 18(11):845-852.

Song; et al. "A Mouse Model for the Human Pathogen *Salmonella typhi*", Cell Host & Microbe (Oct. 2010), 17(8):369-376.

Spits, Hergen; "New models of human immunity"; *Nature Biotechnology vol. 32, No. 4*; (Apr. 2014), pp. 335-336.

Stanley, E. Richard, "Lineage Commitment: Cytokines Instruct, At Last!" *Cell Stem Cell, 5*; (Sep. 4, 2009); pp. 234-236.

Stanley, E.R. et al. (1997) "Biology and action of colony—stimulating factor-1"; Mol. Reprod. Dev. 46:4-10.

Strowig et al., "Transgenic expression of human signal regulatory protein alpha in Rag2-/-γc-/- mice improves engraftment of human hematopoietic cells in humanized mice", *PNAS 108(32)*; (2011); pp. 13218-13223.

Strowig et al., 2010, "Human NK cells of mice with reconstituted human immune system components require preactivation to acquire functional competence," Blood. Nov. 18, 2010;116(20):4158-67. doi: 10.1182/blood-2010-02-270678. Epub Jul. 29, 2010.

Strowig Till et al; "Humanized mouse models of infectious diseases"; *Drug Discovery Today: Disease Models.*; Jan. 2012; pp. e11-e16; XP055166844.

(56) References Cited

OTHER PUBLICATIONS

Suematsu et al. (1989) "IgG1 plasmacytosis in interleukin 6 transgenic mice"; *Proc. Natl. Acad. Sci. USA, 86*; pp. 7547-7551.

Suematsu et al. (1992) "Generation of plasmacytomas with the chromosomal translocation t(12;15) in interleukin 6 transgenic mice"; *Proc. Natl. Acad. Sci. USA, 89*; pp. 232-235.

Sugita et al.; (1990) "Functional Murine Interleukin 6 Receptor with the Intracisternal a Particle Gene Product at its Cytoplasmic Domain"; *J. Exp. Med., 171*;; pp. 2001-2009.

Takagi et al. (2012) "Membrane-bound human SCF/KL promotes in vivo human hematopoietic engraftment and myeloid differentiation"; Blood 119(12):2768-77. doi: 10.1182/blood-2011-05-353201. Epub Jan. 25, 2012.

Takenaka et al., (2007), Polymorphism in Sirpa modulates engraftment of human hematopoietic stem cells; Nature Immunology 8: 1313-1323.

Takizawa & Manz, (2007) "Macrophage tolerance: CD47-SIRP-alpha-mediated signals matter"; Nat Immunol. 8(12):1287-1289.

Tan et al. (2001) "IL-7 is critical for homeostatic proliferation and survival of naive T cells"; *PNAS, 98(15)*; pp. 8732-8737.

Tanabe et al. (1988) "Genomic Structure of the Murine IL-6 Gene-High Degree Conservation of Potential Regulatory Sequences between Mouse and Human"; *The Journal of Immunology, D 141*; pp. 3875-3881.

Tang (2013) "Tumor-associated macrophages as potential diagnostic and prognostic biomarkers in breast cancer"; Cancer Lett. May 10, 2013; 332(1):3-10. doi: 10.1016/j.canlet.2013.01.024. Epub Jan. 21, 2013.

Tassone et al. (2005) "A clinically relevant SCID-hu in vivo model of human multiple myeloma"; Blood 106(2):713-6. Epub Apr. 7, 2005.

The Jackson Laboratory, "Immunodeficient Mouse and Xenograft Host Comparisons", 5 page web printout (Oct. 7, 2022).

The Jackson Laboratory, "Strain Name: C; 129S4-Rag2tm1.1Flv; Csf1tm1.1(CSF1)Flv; Il2rgtm1.1Flv/J" JAX Mice Database, http://jaxmic.jax.org/strain/107708.html, 6 pages (Jan. 26, 2012).

Theocharides et al (2016) "Humanized hemato-lymphoid system mice"; Haematologica. (1); 5-19.

Theocharides, et al; (2012) "Disruption of SIRPα signaling in macrophages eliminates human acute myeloid leukemia stem cells in xenografts"; *J Exp Med. 209(10)*; pp. 1883-1899.

Tong et al. (2010) "Production of p53 gene knockout rats by homologous recombination in embryonic stem cells"; *Nature 467(7312)*; pp. 211-215.

Traggiai; et al. "Development of a Human Adaptive Immune System in Cord Blood Cell-Transplanted Mice", Science (Apr. 2004), 304:104-107.

Tsantikos et al.; "Autoimmune Disease in Lyn-Deficient Mice is Dependent on an Inflammatory Environment Established by IL-6"; *The Journal of Immunology, 184*; (2010); pp. 1348-1360.

Tsujinaka et al. (1995) "Muscle Undergoes Atrophy in Associate with Increase of Lysosomal Cathepsin Activity in Interleukin-6 Transgenic Mouse"; *Biochemical and Biophysical Research Communication, 207(1)*; pp. 168-174.

Tsujinaka et al.; "Interleukin 6 Receptor Antibody Inhibits Muscle Atrophy and Modulates Proteolytic Systems in Interleukin 6 Transgenic Mice"; *J. Clin. Invest., 97(1 )*; (1996); pp. 244-249.

Tsuruta, Lisako, et al, "Transcriptional Regulation of Cytokine Genes"; *Cytokines & Cytokine Receptors: Physiology and Pathological Disorders*, Chapter 23, (2003); pp. 383-403.

Ueda, Otoya et al; "Novel genetically-humanized mouse model established to evaluate efficacy of therapeutic agents to human interleukin-6 receptor"; *Scientific Reports. Nature Publishing Group, GB, vol. 3*; Jan. 1, 2013; p. 1196; XP002692003.

Uehira et al.; "Immunologic Abnormalities Exhibited in IL-7 Transgenic Mice with Dermatitis"; *J. Invest Dermatol, 110*; (1998); pp. 740-745.

Uehira et al.; "The development of dermatitis infiltrated by γδ T cells in IL-7 transgenic mice"; International Immunology, 5(12); (1993); pp. 1619-1627.

Valenzuela et al. (2003) "High-throughput engineering of the mouse genome coupled with high-resolution expression analysis," Nat Biot 21 (6):652-659.

Valmori et al., 1998, "Enhanced Generation of Specific Tumor-Reactive CTL In Vitro by Selected Melan-A/MART-1 Immunodominant Peptide Analogues," Journal of Immunology 160:1750-1758.

Van De Wiele et al.; "Impaired thymopoiesis in interleukin-7 receptor transgenic mice is not corrected by Bcl-2"; *Cellular Immunology, 250*; (2007); pp. 31-39.

Van Der Weyden et al., "Tools for Targeted Manipulation of the Mouse Genome" *Physiological Genomics 11*; (2002); pp. 133-164.

Van Lent et al.,2009, "IL-7 enhances thymic human T cell development in "human immune system" Rag2-/-IL-2Rgammac-/- mice without affecting peripheral T cell homeostasis," J Immunol. Dec. 15, 2009;183(12):7645-55. doi.

Vaughan, Ashley M. et al; "Development of humanized mouse models to study human malaria parasite infection"; Future Microbiology, vol. 7, No. 5; (May 2012); pp. 657-665.

Verstegen et al. "Thrombopoietin is a major limiting factor for selective outgrowth of human umbilical cord blood cells in non-obese diabetic/severe combined immunodeficient recipient mice" *British Journal of Hematology 122*; (2003) pp. 837-846.

Vivier et al., 2008, "Functions of natural killer cells," Nat Immunol. May 2008; 9(5):503-10. doi: 10.1038/ni1582.

Vudattu, et al (2014) "Humanized mice as a model for aberrant responses in human T cell immunotherapy"; J Immunol. 193(2): pp. 587-596.

Waldron-Lynch, et al. (2012) "Teplizumab induces human gut-tropic regulatory cells in humanized mice and patients"; Sci Transl Med. 4(118):118ra12; pp. 1-12.

Wall (1997) "Transgenic dairy cattle: genetic engineering on a large scale"; J Dairy Sci;80: pp. 2213-2224.).

Wallace, et al (2007) "Manipulating the Mouse Genome to Engineer Precise Functional Syntenic Replacements with Human Sequence"; Cell vol. 128, Issue 1; pp. 197-209.

Watanabe (1997), "GM-CSF-mobilized peripheral blood CD34+ cells differ from steady-state bone marrow CD34+ cells in adhesion molecule expression"; *Bone Marrow Transplant.* Jun. 1997; 19(12):1175-81.

Watanabe et al. (1998) "Interleukin 7 Transgenic Mice Develop Chronic Colitis with Decreased Interleukin 7 Protein Accumulation in the Colonic Mucosa"; *J. Exp. Med., 187(3)*; pp. 389-402.

Watanabe et al. (2009) "The analysis of the functions of human B and T cells in humanized NOD/shi-scid/gammac(null) (NOG) mice (hu-HSC NOG mice)," Int Immunol. Jul. 2009;21(7):843-58. doi: 10.1093/intimm/dxp050. Epub Jun. 10, 2009.

Watanabe Takeshi (2008) "Development of Humanized Mouse and Its Application"; Chemistry and Biology, vol. 46, No. 9, pp. 614-620. (w/partial English translation).

Wei et al., "Transgenic expression of CSF-1 in CSF-1 receptor-expressing cells lead to macrophage activation, osteoporosis, and early death" Journal of Leukocyte Biology, 80:1445-1453 (Dec. 2006).

Weissenbach et al. (1980); "Two interferon mRNAs in human fibroblasts: In vitro translation and D *Escherichia coli* cloning studies"; Proc. Natl. Acad. Sci. USA, 77(12); pp. 7152-7156.

Wendling, F. et al. (1994) "cMpl ligand is a humoral regulator of megakaryocytopoiesis," *Nature 369*:571-574.

Wheeler et al.; "Transgenic Technology and Applications in Swine"; *Theriogenology, 56*; (2001); pp. 1345-1369.

Wiktor-Jedrzejczak, W. et al. (1990) Total absence of colony-stimulating factor 1 in the macrophage-deficient osteopetrotic (op/op) mouse, Proc. Natl Acad. Sci. USA 87:4828-4832.

Williams, et al.; "IL-7 Overexpression in Transgenic Mouse Keratinocytes Causes a Lymphoproliferative Skin Disease Dominated by Intermediate TCR Cells"; *The Journal of Immunology*, 159; (1997); pp. 3044-3056.

Willinger et al.; "Improving human hemato-lymphoid-system mice by cytokine knock-in gene replacement"; *Trends in Immunology, 32(7)*; (2011); pp. 321-327.

Willinger Tim; "A new flavor of the humanized mouse: The human IL-3/GM-CSF knock-in mouse"; IWHM2 2nd International Work-

(56) References Cited

OTHER PUBLICATIONS shop on Humanized Mice, PowerPoint Presentation; Apr. 3-6, 2009; Sint Olofskapei/Amsterdam, NL; pp. 1-23.

Willinger, et al; "Human IL-3/GM-CSF knock-in mice support human alveolar macrophage development and human immune responses in the lung", PNAS 108(6); (Feb. 2011); pp. 2390-2395.

Wilmut (2003) "Dolly-her life and legacy"; Cloning Stem Cell 5; pp. 99-1 00.

Woodroofe et al.; "Long-Term Consequences of Interleukin-6 Overexpression in Transgenic Mice"; *DNA and Cell Biology, 11(8)*; (1992); pp. 587-592.

Yaccoby and Epstein, 1999, "The proliferative potential of myeloma plasma cells manifest in the SCID-hu host," Blood. Nov. 15, 1999;94(10):3576-82.

Yaccoby et al., (1998), "Primary myeloma cells growing in SCID-hu mice: a model for studying the biology and treatment of myeloma and its manifestations," Blood. Oct. 15, 1998;92(8):2908-13.

Yajima et al., (2008) "A new humanized mouse model of Epstein-Barr virus infection that reproduces persistent infection, lymphoproliferative disorder, and cell-mediated and humoral immune responses," J Infect Dis. Sep 1;198(5):673-82. doi: 10.1086/590502.

Yamasaki et al.; "Cloning and Expression of the Human Interleukin-6 (BSF-2/IFNβ 2) Receptor"; *Science, 241*; (1988); pp. 825-828.

Yanagimachi (2002) "Cloning: experience from the mouse and other animals"; Mol Cell Endocrinol. 187; pp. 241-248.

Yang et al. (2016) "Mutant PFN1 causes ALS phenotypes and progressive motor neuron degeneration in mice by a gain of toxicity"; PNAS, 113(41), E6209-E6218, p. 1-10.

Yao et al. (2014) "CyTOF supports efficient detection of immune cell subsets from small samples"; J. of Immunological Methods 415; pp. 1-5.

Yasukawa et al.; (1987); "Structure and expression of human B cell stimulatory factor-2 (BSF-2/IL-6) gene"; The EMBO *Journal, 6(10)*; pp. 2939-2945.

Yeung, Y.G. and Stanley, E.R. (2003) "Proteomic approaches to the analysis of early events in colony-stimulating factor-1 signal transduction," Mol. Cell. Proteomics 2:1143-1155.

Yoshida, H. et al. (1990) "The murine mutation osteopetrosis is in the coding region of the macrophage colony stimulating factor gene," *Nature 345*:442-444.

Yoshihara, H. et al. "Thrombopoietin/MPL signaling regulates hematopoietic stem cell quiescence and interaction with the osteoblastic niche," *Cell Stem Cell*. Dec. 13, 2007; 1(6):685-97. doi: 10.1016/j.stem.2007.10.020. Epub Nov. 20, 2007.

Young; et al. "Infectious disease: Tuberculosis", Eur. J. Immunol (2009), 39:1991-2058. U.S. Appl. No. 14/469,308.

Yu et al (2017) "A novel humanized mouse model with significant improvement of class-switched, antigen-specific antibody production"; Blood. 129(8); pp. 959-969.

Yu et al. (2008)., "CSF-1 receptor structure/function in MacCsf1r-/- macrophages: regulation of proliferation, differentiation, and morphology" *Journal of Leukocyte Biology, 84*: (September pp. 852-863.

Zang, W, et al. (2001), "Thrombopoietic effect of recombinant human thrombopoietin gene transferred to mice mediated by electric pulse on normal and experimental thrombocytopenia mice", [Article in Chinese] *Zhonghua Xue Ye Xue Za Zhi. 22(3)*: (Mar. English Abstract.

Zang, WP et al. (2001) "Transfer and Expression of Recombinant Human Thrombopoietin Gene in COS-7 Cells and Mice In Vivo", [Article in Chinese] *Zhongguo Shi Yan Xue Ye Xue Za Zhi 9(1)*: (Mar., English Abstract.

Zhan et al., (2006) "The molecular classification of multiple myeloma" Blood. Sep. 15, 2006;108(6):2020-8. Epub May 25.

Zhao; et al (1998). "Thrombopoietin: a potential T-helper lymphocyte stimulator. Change in T-lymphocyte composition and blood cytokine levels in thrombopoietin eDNA transferred mice", Haematolgica (Jun. 83(6):572-573.

Zhou et al., (1997) "Transgenic Mice Overexpressing Human c-mpl Ligand Exhibit Chronic Thrombocytosis and Display Enhanced Recovery From 5-Fluorouracil or Antiplatelet Serum Treatment" Blood 89:1551-1559.

Zhou Hongxia, et al. (2009) "Developing tTA transgenic rats for inducible and reversible gene expression"; International Journal of Biological Sciences, , 5, pp. 171-181.

Zilberstein et al. (1986); "Structure and expression of cDNA and genes for human interferon-beta-2; a distinct species inducible by growth-stimulatory cytokines"; *The EMBO Journal, 5(10)*; pp. 2529-2537.

Pearson et al., Humanized SCID Mouse Models for Biomedical Research, Current Topics in Microbiology and Immunology, 324;25-51, 2008.

```
mEpo    1 MGVPERPT-LLLLLSLLLIPLGLPVLCAPPRLICDSRVLERYILERYILEAKEAENVTMGCAEGPRLSENITTVPDTKVNFYAWKRMEVEEQAIEVWQGLSLLSEA  99
hEPO    1 MGVHECPAWLWLLLSLLSLPLGLPLGLPVLGAPPRLICDSRVLERYLLERYLLEAKEAENITTGCAEHCSLNENITVPDTKVNFYAWKRMEVGQQAVEVWQGLALLSEA 100 mEpo  100 ILQAQALLANSSQPPETLQLHIDKAISGLRSLTSLLRVLGAQKELMSPPDTTPPAPLRTLTVDTFCKLFRVYANFLRGKLKLYTGEVCRRGDR 192
hEPO  101 VLRGQALLVNSSQPWEPLQLHVDKAVSGLRSLTTLLRALGAQKEAISPPDAASAAPLRTITADTFRKLFRVYSNFLRGKLKLYTGEACRTGDR 193 mEpo (SEQ ID NO:2)
hEPO (SEQ ID NO:4)
```

FIG. 1

EPO humanization Schematic 1 kb

WT

KI

Ex1  2  3  4  5

SEQ ID NO:5

SEQ ID NO:6

SEQ ID NO:7 loxP neo

Ub loxP

SEQ ID NO:5

- - - - mouse sequence
——— human sequence
mouse untranslated region
human untranslated region
mouse coding region
human coding region
selection cassette WT = wild type Epo mouse locus KI = humanized Epo mouse locus Sirpa humanization Schematic

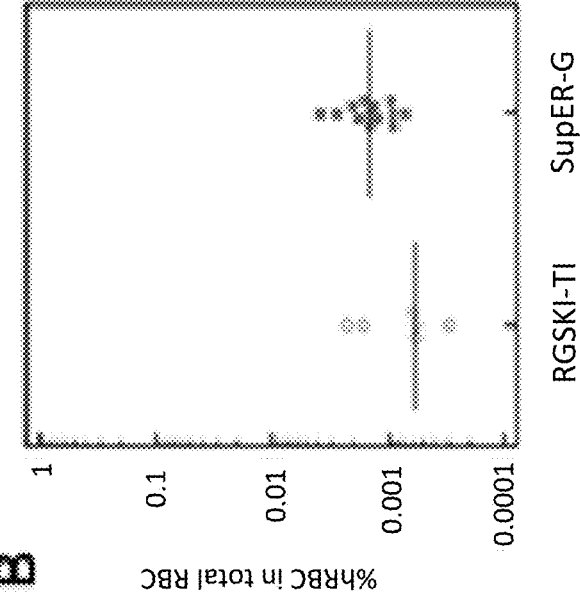
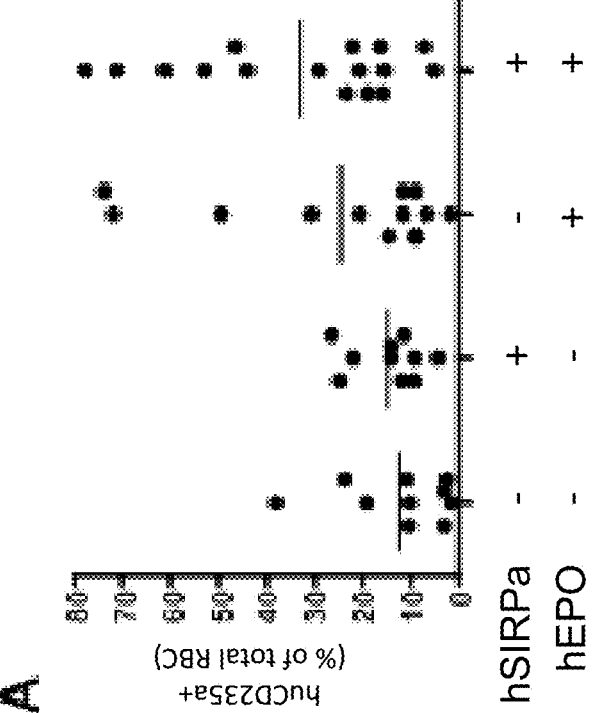
FIG. 5

GENETICALLY MODIFIED NON-HUMAN ANIMALS EXPRESSING HUMAN EPO

CROSS-REFERENCE

This application is a continuation of U.S. application Ser. No. 16/672,042, filed Nov. 1, 2019, now U.S. Pat. No. 11,766,032, which application is a division of U.S. application Ser. No. 14/715,446, filed May 18, 2015, now U.S. Pat. No. 10,463,028, which application claims the benefit of U.S. Provisional Application No. 62/000,460, filed May 19, 2014, the disclosure each of which is incorporated herein by reference in its entirety.

INCORPORATION BY REFERENCE OF SEQUENCE LISTING PROVIDED AS A SEQUENCE LISTING XML FILE

A Sequence Listing is provided herewith as a Sequence Listing XML, "REGN-013DIVCON_SEQ_LIST", created on Aug. 10, 2023, and having a size of 27,945 bytes. The contents of the Sequence Listing XML are incorporated herein by reference in their entirety.

FIELD OF THE INVENTION

This invention pertains to the field of genetically modified non-human animals.

INTRODUCTION

Genetically modified mice, modified and engrafted mice, and their use in modeling human diseases are known in the art. However, to date, there has been little success in generating genetically modified mice that model human infection by pathogens that target cells of the human erythroid lineage. Such pathogens, e.g., protozoans of the genera *Plasmodium, Babesia,* and *Theileria,* may cause life-threatening diseases in humans.

For example, protozoans of the genus *Plasmodium* cause malaria. During 2010, a total of 106 countries worldwide were considered as endemic of malaria with an estimated 3.3 billion people at risk for developing the disease. The disease burden in 2010 was estimated at 216 million cases with 655,000 estimated deaths worldwide, in which, 86% were in children under 5 years of age. Currently, drugs and vaccines for the prevention and treatment of malaria are still very limited. In addition, parasite resistance to commonly used malaria therapeutics has emerged and presents a constant challenge. The development of new drugs and vaccines for the control and treatment of pathogens that target human erythrocytes are therefore urgently needed.

Since many of these pathogens do not infect the red blood cells of laboratory rodents, in vivo studies have traditionally been limited to studies of malaria caused by the rodent parasite *Plasmodium berghei* ANKA, or to studies of NOD/SCID, NOD/SCID/IL2rg$^{null}$ (NSG), or BXN mice acutely engrafted by daily injection of large numbers of human erythrocytes and coincidentally or subsequently infected by injection of parasitized red blood cells (Angulo-Barturen et al. (2008) A murine model of falciparum-malaria by in vivo selection of competent strains in non-myelodepleted mice engrafted with human erythrocytes. PLoS One 3:e2252; Jimenez-Diaz et al. (2009) Improved murine model of malaria using *Plasmodium falciparum* competent strains and non-myelodepleted NOD-scid IL2Rgnull mice engrafted with human erythrocytes. Antimicrob Agents Chemother 53:4533-4536; Badell et al. (2000) Human malaria in immunocompromised mice: an in vivo model to study defense mechanisms against *Plasmodium falciparum*. JEM 192(11): 1653-1660; Moreno et al. (2006) The course of infections and pathology in immunomodulated NOD/LtSz-SCID mice inoculated with *Plasmodium falciparum* laboratory lines and clinical isolates. Int. J. Parasitol. 36:361-369). In order to study the effects of *Plasmodium* and other pathogens on humans, and to test vaccines and drugs for efficacy in preventing infection and treating humans infected with these and other pathogens, it would be useful to have a non-human animal such as a mouse that is genetically modified so that it is susceptible to infection with such a pathogen, or so that it will better support human erythrocytes that are acutely grafted into the animal prior to infection as done in traditional rodent models.

SUMMARY

Genetically modified non-human animals expressing human EPO from the animal genome are provided. Also provided are methods for making non-human animals expressing human EPO from the non-human animal genome, and methods for using non-human animals expressing human EPO from the non-human animal genome. These animals and methods find many uses in the art, including, for example, in modeling human erythropoiesis and erythrocyte function; in modeling human pathogen infection of erythrocytes; in in vivo screens for agents that modulate erythropoiesis and/or erythrocyte function, e.g. in a healthy or a diseased state; in in vivo screens for agents that are toxic to erythrocytes or erythrocyte progenitors; in in vivo screens for agents that prevent against, mitigate, or reverse the toxic effects of toxic agents on erythrocytes or erythrocyte progenitors; in in vivo screens of erythrocytes or erythrocyte progenitors from an individual to predict the responsiveness of an individual to a disease therapy.

In some aspects of the invention, genetically modified non-human animals are provided that express human EPO from the non-human animal's genome. In other words, the non-human animal comprises a nucleic acid sequence encoding a human EPO protein.

In some embodiments, the nucleic acid sequence encoding a human EPO protein is operably linked to an EPO gene promoter. In some embodiments, the EPO gene promoter is the human EPO promoter. In other embodiments, the EPO promoter is the endogenous, i.e. non-human, EPO promoter. In certain such embodiments, the endogenous EPO promoter is at the non-human animal EPO gene locus. In other words, in certain embodiments, the nucleic acid sequence that encodes the human EPO protein is operably linked to the non-human animal EPO promoter at the non-human animal EPO locus. In some such embodiments, the operable linkage results in a null mutation in the non-human EPO gene at the non-human EPO gene locus.

In some embodiments, the subject non-human animal is heterozygous for the allele comprising the nucleic acid sequence that encodes the human EPO protein. In other embodiments, the non-human animal is homozygous for the allele comprising the nucleic acid sequence that encodes the human EPO protein.

In some embodiments, the nucleic acid sequence that encodes the human EPO protein comprises human EPO genomic coding and non-coding sequence. In other embodiments, the nucleic acid sequence that encodes the human EPO protein comprises human EPO cDNA sequence.

In some embodiments, the subject non-human animal expresses one or more additional human proteins selected from the group consisting of: a M-CSF protein encoded by a nucleic acid under the control of an M-csf promoter, a IL-3 protein encoded by a nucleic acid under control of an Il-3 promoter, a GM-CSF protein encoded by a nucleic acid under the control of a Gm-csf promoter, a TPO protein encoded by a nucleic acid under the control of a TPO promoter, and a Sirpa protein encoded by a nucleic acid under the control of a Sirpa promoter. In some such embodiments, the promoter is an endogenous non-human animal promoter at the corresponding non-human animal gene locus, and the non-human animal is heterozygous null for the non-human gene. In other embodiments, the promoter is an endogenous non-human animal promoter at the corresponding non-human animal gene locus, and the non-human animal is homozygous null for the non-human gene. In certain embodiments, the non-human animal expresses human, e.g., humanized, proteins, selected from the group consisting of human, e.g., humanized, TPO; human, e.g., humanized, IL-3; human, e.g., humanized, GM-CSF; human, e.g., humanized, EPO; and human, e.g., humanized, Sirpa; and a combination thereof.

In some embodiments, the subject genetically modified non-human animal is a mouse having a genome that comprises a nucleic acid sequence encoding a human, e.g., humanized protein, e.g. a nucleic acid encoding a human, e.g., humanized, EPO; a human, e.g., humanized, Sirpa; a human, e.g., humanized, IL-3; a human, e.g., humanized, GM-CSF, a human, e.g., humanized, M-CSF, a human, e.g., humanized, TPO, a human, e.g., humanized, IL-6; etc. operably linked to its corresponding non-human animal promoter, e.g. a Sirpa, IL-3, GM-CSF, M-CSF, TPO, or IL-6 promoter, respectively, wherein the animal expresses the encoded human protein(s) and the native mouse protein(s). In other embodiments, the subject genetically modified non-human animal is a mouse having a genome that comprises a nucleic acid sequence encoding a human, e.g., humanized, protein, e.g. a nucleic acid encoding human, e.g., humanized, EPO; human, e.g., humanized, Sirpa; human, e.g., humanized, IL-3; human, e.g., humanized GM-CSF; human, e.g., humanized M-CSF; human, e.g., humanized, TPO, operably linked to its corresponding non-human animal promoter, e.g. a Sirpa, IL-3, GM-CSF, M-CSF, or TPO promoter, respectively, wherein the animal expresses the encoded human protein(s) and does not express the native mouse protein(s). Thus, in some embodiments, the genetically modified non-human animal is a mouse and the mouse is heterozygous for some or all the human, e.g., humanized, genes disclosed herein. In some embodiments, the genetically modified non-human animal is a mouse and the mouse is homozygous for some or all of the human, e.g., humanized genes disclosed herein.

In some embodiments, the subject non-human animal is immunodeficient for an endogenous immune system. In some such embodiments, the immunodeficiency is caused by a deficiency for one or both of Rag2 and IL2rg.

In some embodiments, the subject genetically modified immunodeficient non-human animal further comprises an engraftment of human hematopoietic cells. In some such embodiments, the human hematopoietic cells comprise one or more cells selected from the group consisting of a human CD34-positive cell, a human hematopoietic stem cell, a human myeloid precursor cell, a human erythroid precursor cell, a human myeloid cell, a human dendritic cell, a human monocyte, a human granulocyte, a human erythrocyte, a human neutrophil, a human mast cell, a human thymocyte, and a human B lymphocyte.

As demonstrated in the working examples herein, human hematopoietic cell-engrafted genetically modified immunodeficient non-human animals comprising a nucleic acid sequence encoding a human EPO protein operably linked to an EPO promoter at the endogenous locus demonstrate high levels of human erythropoiesis in the bone marrow and a 2 to 5-fold increase in human cells of the erythroid lineage in bone marrow as compared with control mice not expressing human EPO. In some embodiments, human hematopoietic cell-engrafted genetically modified immunodeficient non-human animals comprising a nucleic acid sequence encoding a human EPO protein operably linked to an EPO promoter at the endogenous locus demonstrate high levels of human erythropoiesis in the bone marrow and about a 2 to about a 10-fold increase in human cells of the erythroid lineage in bone marrow as compared with control mice not expressing human EPO, e.g., about a 2 fold, about a 3 fold, about a 4 fold, about a 5 fold, about a 6 fold, about a 7 fold, about an 8 fold, about a 9 fold, or about a 10 fold increase in human cells of the erythroid lineage in bone marrow as compared with control mice not expressing human EPO. As such, in some embodiments, the subject engrafted, genetically modified immunodeficient animal comprises bone marrow in which 20% or more of the erythroid cells (CD235+) are human erythroid cells. In some embodiments, the subject engrafted, genetically modified immunodeficient animal comprises bone marrow in which about 10% or more, e.g., about 20% or more, about 30% or more, about 40% or more, or about 50% or more of the erythroid cells (CD235+) are human erythroid cells.

In some such embodiments, the subject genetically modified animal is an immunodeficient mouse comprising a nucleic acid encoding a human EPO protein operably linked to the non-human animal EPO promoter at the non-human animal EPO locus, a nucleic acid encoding a human TPO protein operably linked to the non-human animal TPO promoter at the non-human animal TPO locus, a nucleic acid encoding a human Il-3 protein operably linked to the non-human animal Il-3 promoter at the non-human animal Il-3 locus, a nucleic acid encoding a human GM-CSF protein operably linked to a GM-CSF promoter at the non-human animal GM-CSF locus, and a nucleic acid encoding a human M-CSF protein operably linked to the non-human animal M-CSF promoter at the non-human animal M-CSF locus, for example, a $Rag2^{-/-}IL2rg^{y/-}Tpo^{h/h}Mcsf^{h/h}Il3^{h/h}Gmcsf^{h/h}Epo^{h/h}$ ("MITER-G") mouse.

In some such embodiments, the subject genetically modified animal is an immunodeficient mouse comprising a nucleic acid encoding a human EPO protein operably linked to the non-human animal EPO promoter at the non-human animal EPO locus, a nucleic acid encoding a human TPO protein operably linked to the non-human animal TPO promoter at the non-human animal TPO locus, a nucleic acid encoding a human Il-3 protein operably linked to the non-human animal Il-3 promoter at the non-human animal Il-3 locus, a nucleic acid encoding a human GM-CSF protein operably linked to a GM-CSF promoter at the non-human animal GM-CSF locus, and a nucleic acid encoding a human M-CSF protein operably linked to the non-human animal M-CSF promoter at the non-human animal M-CSF locus, and a nucleic acid encoding a human SIRPa protein operably linked to the non-human animal SIRPa promoter randomly integrated into the non-human animal genome, for example, a $Rag2^{-/-}IL2rg^{y/-}Tpo^{h/h}Mcsf^{h/h}Il3^{h/h}Gmcsf^{h/h}Epo^{h/}$

5

*h*hSIRPα⁺ ("MISTER-G") mouse. In other such embodiments, the nucleic acid encoding a human, e.g., humanized, SIRPa protein is operably linked to the non-human animal SIRPα promoter at the non-human animal locus, for example, a Rag2$^{-/-}$IL2rg$^{y/-}$Tpo$^{h/h}$Mcsf$^{h/h}$Il3$^{h/h}$Gmcsf$^{h/h}$Epo$^{h/h}$SIRPα$^{h/h}$ ("SupER-G") mouse.

In some such embodiments, the subject genetically modified animal is an immunodeficient mouse comprising one allele of a nucleic acid encoding a human EPO protein operably linked to the non-human animal EPO promoter at the non-human animal EPO locus (i.e., the mouse is heterozygous for human EPO), a nucleic acid encoding a human, e.g., humanized, SIRPa protein operably linked to the non-human animal SIRPα promoter at the non-human animal SIRPa locus, a nucleic acid encoding a human TPO protein operably linked to the non-human animal TPO promoter at the non-human animal TPO locus, a nucleic acid encoding a human Il-3 protein operably linked to the non-human animal Il-3 promoter at the non-human animal Il-3 locus, and a nucleic acid encoding a human GM-CSF protein operably linked to a GM-CSF promoter at the non-human animal GM-CSF locus, for example, a Rag2$^{-/-}$IL2rg$^{y/-}$Tpo$^{h/}$*h*Il3$^{h/h}$Gm-csf$^{h/h}$Epo$^{h/m}$SIRPα$^{h/h}$ ("TIES") mouse.

In some embodiments, human hematopoietic cell-engrafted genetically modified immunodeficient non-human animals comprising a nucleic acid sequence encoding a human EPO protein operably linked to an EPO promoter at the endogenous locus may demonstrate better survival and engraftment with human erythrocytes when they comprise only one copy of the nucleic acid sequence encoding the EPO protein, and when they comprise endogenous M-csf. This is because the high level of human myeloid cell engraftment supported by human M-CSF in the knock-in results in the destruction of mouse red blood cells, which in turn leads to anemia and death of engrafted mice. In addition, heterozygosity for the human EPO allele improves fertility, developmental competency, and viability over mice homozygous for human EPO and null for mouse EPO. As such, in some embodiments, the subject engrafted, genetically modified immunocompromised animal demonstrates improved viability over mice that constitutively express EPO, e.g. transgenic mice, or mice that comprise two copies of human EPO, e.g. EPO$^{h/h}$. In some such embodiments, the genetically modified immunodeficient non-human animal is the TIES mouse (Rag2$^{-/-}$IL2rg$^{y/-}$Tpo$^{h/h}$Il3$^{h/h}$Gm-csf$^{h/h}$Epo$^{h/m}$SIRPα$^{h/h}$)

In some embodiments, human hematopoietic cell-engrafted genetically modified immunodeficient non-human animals injected with clodronate liposomes show a 1000-fold increase in the number of human erythroid cells (CD235+) in the peripheral blood as compared to uninjected animals. In some embodiments, human hematopoietic cell-engrafted genetically modified immunodeficient non-human animals injected with clodronate liposomes show about a 10-fold or greater, about a 50 fold or greater, about a 100-fold or greater, about a 500 fold or greater, or about a 1000-fold or greater increase in the number of human erythroid cells (CD235+) in the peripheral blood as compared to uninjected animals. Of these human erythroid cells, 10% or more, 20% or more, 30% or more, 40% or more, or 50% or more may be reticulocytes (erythrocyte precursors, CD71+). As such, in some embodiments, subject engrafted, genetically modified immunodeficient animal comprises peripheral blood in which 1% or more, e.g., 5% or more or 10% or more, of the erythroid cells (CD235+) are human erythroid cells, and 10% or more, e.g., 20% or more, 30% or more, 40% or more, or 50% or more, of those human erythroid cells are human reticulocytes (CD71+). In some such embodiments, the subject engrafted genetically modified immunodeficient non-human animal is the MISTER-G mouse, SupER-G mouse, or TIES mouse.

In some embodiments, the non-human animal further comprises an infection with a pathogen that targets human cells of the erythroid lineage. In some such embodiments, the pathogen is selected from a *Plasmodium* sp., *Babesia* sp., and a *Theileri* sp. In some embodiments, the infection is produced by injecting parasite into the non-human animal. In some embodiments, the infection is produced by injecting parasitized human erythroid cells into the non-human animal. In some embodiments, the infection is produced by injecting parasitized human erythroid cells and healthy human erythroid cells into the non-human animal.

In some aspects of the invention, methods are provided for identifying an agent that inhibits an infection by a pathogen that targets human cells of the erythroid lineage.

In some embodiments, the method comprises administering a candidate agent to a genetically modified non-human animal, wherein the animal comprises a nucleic acid sequence that encodes a human EPO protein operably linked to an EPO gene promoter, one or more gene mutations that results in immunodeficiency in the non-human animal, an engraftment of human hematopoietic cells, and an infection by a pathogen that targets human cells of the erythroid lineage; and determining whether the agent reduces the amount of the pathogen in the pathogen-infected non-human animal.

In some embodiments, the method comprises contacting a human hematopoietic cell-engrafted, genetically modified immunodeficient non-human animal comprising a nucleic acid sequence that encodes a human EPO protein operably linked to an EPO gene promoter with clodronate; administering a candidate agent to the clodronate-contacted non-human animal; injecting the genetically modified non-human animal with parasitized reticulocytes or erythrocytes; and determining whether the agent prevents the infection of the human reticulocytes and/or erythrocytes of the non-human animal.

In some embodiments, the pathogen is selected from a *Plasmodium* sp., *Babesia* sp., and a *Theileri* sp. In some such embodiments, the pathogen is selected from *P. falciparum* and *P. vivax*. In some embodiments, the non-human animal is a mammal. In some such embodiments, the mammal is a rodent. In certain such embodiments, the rodent is a mouse.

In some aspects of the invention, methods are provided for making a mouse expressing human EPO. In some embodiments, the method comprises contacting a mouse pluripotent stem cell with a nucleic acid sequence comprising coding sequence for a human EPO protein or a fragment thereof operably linked to EPO promoter sequence, wherein the coding sequence and EPO promoter sequence form a cassette that is flanked by sequences that are homologous to the endogenous mouse EPO locus; culturing the pluripotent stem cell under conditions that promote the integration of the nucleic acid sequence into the mouse genome at the endogenous mouse EPO locus by homologous recombination; and making a mouse from the mouse pluripotent stem cell that comprises the nucleic acid sequence encoding a human EPO protein.

In some embodiments, the mouse pluripotent stem cell is an embryonic stem (ES) cell or an induced pluripotent stem (iPS) cell. In some embodiments, the mouse pluripotent stem cell is deficient for Rag2 and/or IL2rg. In some embodiments, the EPO promoter sequence is sequence for the human EPO promoter. In other embodiments, the EPO promoter sequence is sequence for the endogenous non-human EPO promoter. In some embodiments, the integration results in a replacement of the non-human EPO gene at the non-human EPO gene locus. In some embodiments, the nucleic acid sequence that encodes the human EPO protein comprises human EPO genomic coding and non-coding sequence. In some embodiments, the nucleic acid sequence that encodes the human EPO protein comprises human EPO cDNA sequence.

In some aspects of the invention, methods are provided for making a mouse expressing a human EPO protein and comprising a human hematopoietic system. In some embodiments, the methods comprise transplanting a population of cells comprising human hematopoietic progenitor cells into the genetically modified immunodeficient mouse made by methods of the present disclosure. In some embodiments, the transplanting comprises tail-vein injection, fetal liver injection, or retro-orbital injection. In some embodiments, the genetically modified immunodeficient mouse is sublethally irradiated prior to transplantation. In some embodiments, the human hematopoietic progenitor cells that are transplanted are CD34+ cells. In some embodiments, the human hematopoietic progenitor cells are from fetal liver, adult bone marrow, or umbilical cord blood.

In some aspects of the invention, methods are provided for making a mouse that is infected with a human pathogen that targets human cells of the erythroid lineage. In some embodiments, the methods comprise making a mouse expressing a human EPO protein and comprising a human hematopoietic system according to methods of the present disclosure, injecting the engrafted mouse with clodronate, and injecting the clodronate-injected mouse with parasitized human red blood cells (PRBCs). In some embodiments, the method further comprises injecting into the mouse healthy human red blood cells. In some embodiments, the parasite is selected from a *Plasmodium* sp., *Babesia* sp., and a *Theileri* sp. In certain embodiments, the *Plasmodium* sp. is selected from *P. falciparum* and *P. vivax*.

BRIEF DESCRIPTION OF THE DRAWINGS

FIG. 1 provides a protein alignment of the mouse Epo (SEQ ID NO:2) to human EPO (SEQ ID NO:4). Underlined residues are residues that are conserved between species.

FIG. 5, Panels A and B, show the frequency of human erythroid cells in HSC-engrafted mice. (Panel A) Human CD235a$^+$ erythrocyte engraftment in the bone marrow 6-8 weeks after HSC engraftment into Rag2$^{-/-}$Il2$^{-/-}$Tpo$^{h/h}$IL3$^{h/}$$_h$Gmcsf$^{h/h}$Mcsf$^{h/h}$ mice ("MITRG mouse") comprising the indicated combinations of human EPO expressed from the mouse EPO locus ("hEPO+") and/or human SIRPa expressed as a random integrant into the mouse genome ("hSIRPa+"). (Panel B) Frequency of human CD235a$^+$ erythrocytes in the peripheral blood in the presence versus absence of hEPO 6-8 weeks after HSC engraftment into Rag2$^{-/-}$Il2rg$^{null}$Tpo$^{h/h}$Mcsf$^{h/h}$Il3$^{h/h}$Gmscf$^{h/h}$Epo$^{h/}$$_h$SIRPα$^{h/h}$ ("SupER-G") mice versus Rag2$^{-/-}$Il2rg$^{null}$Tpo$^{h/}$$_h$IL3$^{h/h}$Gmcsf$^{h/h}$Sirpa$^{h/h}$ ("RGSKI-TI") control mice.

DETAILED DESCRIPTION

Figure 2:
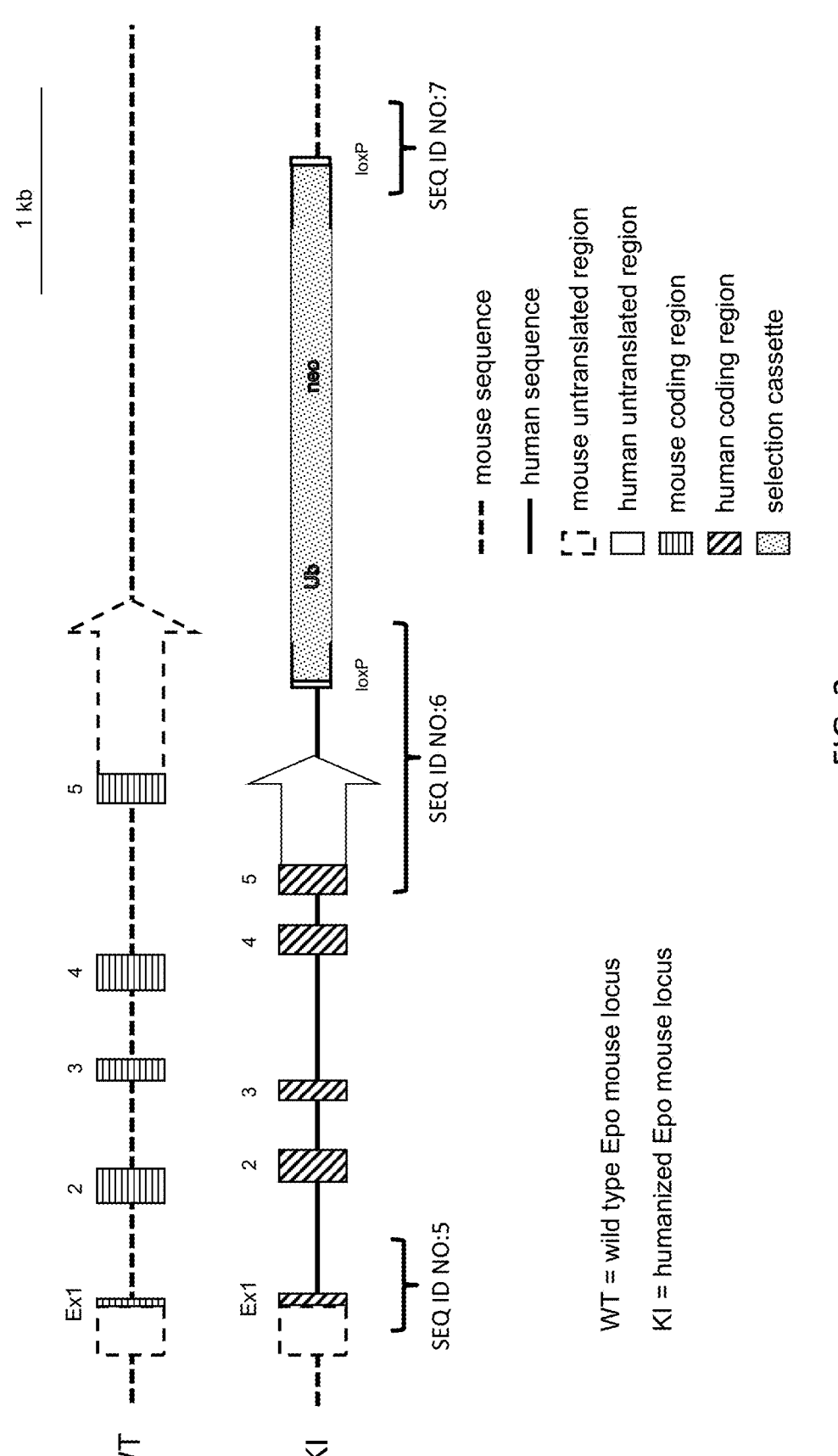
FIG. 2 provides schematics of the wild type mouse EPO locus before and after knock-in of a nucleic acid sequence encoding human EPO.

Genetically modified non-human animals expressing human EPO from the animal genome are provided. Also provided are methods for making non-human animals expressing human EPO from the animal genome, and methods for using non-human animals expressing human EPO from the animal genome. These animals and methods find many uses in the art, including, for example, in modeling human erythropoiesis and erythrocyte function; in modeling human pathogen infection of erythrocytes; in in vivo screens for agents that modulate erythropoiesis and/or erythrocyte function, e.g. in a healthy or a diseased state; in in vivo screens for agents that are toxic to erythrocytes or erythrocyte progenitors; in in vivo screens for agents that prevent against, mitigate, or reverse the toxic effects of toxic agents on erythrocytes or erythrocyte progenitors; in in vivo screens of erythrocytes or erythrocyte progenitors from an individual to predict the responsiveness of an individual to a disease therapy. These and other objects, advantages, and features of the invention will become apparent to those persons skilled in the art upon reading the details of the compositions and methods as more fully described below.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims. The invention is not limited to particular embodiments discussed, but is described by the granted claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Genetically Modified Non-Human Animals

In one aspect of the invention, non-human animals are provided that are genetically modified to express one or more human proteins from their genome. In some aspects of the invention, the human protein is a human erythropoietin (hEPO) protein (SEQ ID NO:4). In other words, the genetically modified non-human animal comprises in its genome a nucleic acid sequence encoding a human EPO (hEPO)

protein. For example, the non-human animal may comprise in its genome a nucleic acid sequence that comprises human EPO genomic coding and non-coding sequence, e.g. sequence at chromosome 7, nucleotides 100318423-100321323 or a fraction thereof. Alternatively, the non-human animal may comprise in its genome a nucleic acid sequence that comprises human EPO cDNA sequence (SEQ ID NO:3) or a fraction thereof. In some instances, the non-human animal is further genetically modified so as to express one or more additional human proteins from the non-human animal's genome. In some such embodiments, these one or more additional human proteins are human proteins that promote human hematopoietic cell development and/or function, for example, a human signal-regulatory protein alpha (hSIRPa) protein (NCBI Gene ID: 140885, GenBank Accession Nos. NM_080792.2, NM_001040022.1, NM_001040023.1), a human interleukin 3 (hIL-3) protein (NCBI Gene ID: 3562, GenBank Accession No. NM_000588.3), a human colony stimulating factor 2 (granulocyte-macrophage) (hGM-CSF) protein (NCBI Gene ID: 1437, GenBank Accession No. NM_000758.3), a human colony stimulating factor 1 (macrophage) (hM-CSF) protein (NCBI Gene ID: 1435, GenBank Accession No. NM_000757.5, NM_172210.2, NM_172211.3, and NM_172212.2), a human thrombopoietin (hTPO) protein (NCBI Gene ID: 7066, GenBank Accession Nos. NM_000460.3, NM_001177597.2, NM_001177598.2, NM_001289997.1, NM_001290003.1, NM_001290022.1, NM_001290026.1, NM_001290027.1, NM_001290027.1), a human interleukin 6 (hIL6) protein (NCBI Gene ID: 3569, GenBank Accession No. NM_000600.3), and the like.

The skilled artisan will appreciate that in addition to "wild type" or "native" human nucleic acids and proteins, the terms "a human nucleic acid" and "a human protein" encompass variants of wild type human nucleic acids and proteins as well. As used herein, the term "variant" defines either an isolated naturally occurring genetic mutant of a human polypeptide or nucleic acid sequence or a recombinantly prepared variation of a human polypeptide or nucleic acid sequence, each of which contain one or more mutations compared with the corresponding wild-type human nucleic acid or polypeptide sequence. For example, such mutations can be one or more amino acid substitutions, additions, and/or deletions. The term "variant" also includes human homologs and orthologues. In some embodiments, a variant polypeptide of the present invention has 70% or more identity, e.g. 75%, 80%, or 85% or more identity to a wild-type human polypeptide, e.g. 90%, 91%, 92%, 93%, 94%, 95%, 96%, 97%, 98% or 99% identity to a wild-type human polypeptide.

The percent identity between two sequences may be determined using any convenient technique in the art, for example, aligning the sequences using, e.g., publicly available software. Mutations can be introduced using standard molecular biology techniques, such as site-directed mutagenesis, PCR-mediated mutagenesis, directed evolution, and the like. One of skill in the art will recognize that one or more nucleic acid substitutions can be introduced without altering the amino acid sequence, and that one or more amino acid mutations can be introduced without altering the functional properties of the human protein.

Conservative amino acid substitutions can be made in human proteins to produce human protein variants. By conservative amino acid substitutions it is meant art-recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, glycine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, proline, threonine, serine, valine, all typically considered to be small.

Human variants can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, methylhistidine, and ornithine.

Human variants will typically be encoded by nucleic acids having a high degree of identity with a nucleic acid encoding the wild-type human protein. In some embodiments, the complement of a nucleic acid encoding a human variant specifically hybridizes with a nucleic acid encoding a wild-type human under high stringency conditions. Nucleic acids encoding a human variant can be isolated or generated recombinantly or synthetically using well-known methodology.

In addition to "wild type" or "native" human proteins, and "variants" thereof, the term "human protein", as used herein, e.g., in the context of a "human EPO protein (hEPO)", a "human SIRPa protein (hSIRPa)", a "human IL-3 protein (hIL-3)", a "human GM-CSF protein (hGM-CSF)", a "human M-CSF protein (hM-CSF)", a "human TPO protein (hTPO)", and a "human IL-6 protein (hIL-6)", encompasses fusion proteins, i.e., chimeric proteins, which include one or more fragments of a wild-type human protein (or a variant thereof) and which retain one or more functions, e.g., one or more signaling and/or receptor functions, of the wild-type human protein. A fusion protein which includes one or more fragments of a wild-type human protein (or a variant thereof), e.g., in combination with one or more non-human peptides or polypeptides, may also be referred to herein as a "humanized protein". Thus, for example, a protein which includes an amino acid sequence of an extracellular domain of a wild-type human SIRPα protein fused with a signaling domain of a wild-type mouse SIRPα protein is encompassed by the term "human SIRPα protein".

A nucleic acid sequence that encodes a human protein is, therefore, a polynucleotide that includes a coding sequence for a human protein, e.g., a wild-type human protein, a variant of a wild-type human protein, a fragment of a wild-type human protein (or a variant thereof) which retains one or more functions, e.g., one or more signaling and/or receptor functions, of the wild-type human protein, or a fusion protein, e.g., a chimeric protein, which includes one or more fragments of a wild-type human protein (or a variant thereof) and which retain one or more functions, e.g., one or more signaling and/or receptor functions of the wild-type human protein.

Typically, in the genetically modified animals of the present disclosure, the nucleic acid encoding the human protein, e.g., the hEPO protein, the hSIRPa protein, the hIL-3 protein, the hGM-CSF protein, the hM-CSF protein, the hTPO protein, the hIL-6 protein, etc. is operably linked to one or more DNA regulatory elements. DNA regulatory elements include transcriptional and translational control sequences, such as promoters, enhancers, polyadenylation signals, terminators, and the like, that provide for and/or regulate expression of a coding sequence in a host cell. For example, a "promoter" or "promoter sequence" refers to a DNA regulatory region capable of binding RNA polymerase in a cell and initiating transcription of a downstream (3' direction) coding sequence. The promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Of particular interest to the present disclosure are DNA regulatory elements, e.g. promoters, which promote the transcription of the human protein in the same spatial and temporal expression pattern, i.e. in the same cells and tissues and at the same times, as would be observed of the corresponding endogenous protein.

In some embodiments, the nucleic acid sequence encoding the human protein in the subject non-human animal is operably linked to the human promoter for the gene, for example, if the human promoter promotes the correct spatial and temporal expression of the human protein in the non-human animal. Alternatively, the nucleic acid sequence encoding the human protein in the subject non-human animal is operably linked to the non-human animal promoter for the corresponding non-human animal gene. Thus, for example, with regard to non-human animals expressing a hEPO protein, in some embodiments, the nucleic acid encoding the hEPO protein is operably linked to a human EPO promoter. In other instances, the nucleic acid encoding the human EPO protein is operably linked to a non-human EPO promoter. In yet other instances, the nucleic acid encoding the human EPO protein is operably linked to endogenous non-human EPO promoter.

In some instances, the human protein is expressed from the corresponding gene locus in the non-human animal. In certain instances, the nucleic acid sequence encoding the human protein replaces the nucleic acid sequence encoding the corresponding non-human animal protein. In other instances, the human protein is expressed from a genomic site in the non-human animal other than the locus for the corresponding non-human gene. Thus, for example, with regard to non-human animals expressing a hEPO protein, in some embodiments, the hEPO protein is expressed from the EPO locus of the non-human animal genome. In certain embodiments, the non-human animal comprises a replacement of nucleic acid sequence encoding endogenous EPO with nucleic acid sequence encoding the hEPO protein. In other embodiments, the hEPO is expressed from a genomic site in the non-human animal other than the non-human animal EPO locus.

In some instances, the genetically modified non-human animal comprises one copy of the nucleic acid sequence encoding the human protein. For example, the non-human animal may be heterozygous for the nucleic acid sequence encoding the human protein, i.e., one allele at a locus is genetically modified, while the other allele is the endogenous allele. In other instances, the genetically modified non-human animal comprises two copies of the nucleic acid sequence encoding the human protein. For example, the non-human animal may be homozygous for the nucleic acid sequence encoding the human protein, i.e., both alleles for a locus in the diploid genome are genetically modified to encode the human protein, e.g. both alleles comprise a replacement of nucleic acid sequence encoding the endogenous protein with nucleic acid sequence encoding the human protein. Thus, for example, with regard to non-human animals expressing a hEPO protein, as discussed above, the nucleic acid sequence encoding a hEPO may be integrated into the non-human animal EPO locus. In some such embodiments, the genetically modified non-human animal is heterozygous for the nucleic acid sequence encoding hEPO protein, i.e. the genetically modified non-human animal comprises one allele comprising the nucleic acid encoding hEPO and one allele encoding endogenous EPO. In other words, the animal is an EPO$^{h/m}$ animal, where "h" represents the allele comprising the human sequence and "m" represents the endogenous allele. In other such embodiments, the genetically modified non-human animal is homozygous for the nucleic acid sequence encoding the hEPO protein, i.e. both alleles for a locus in the diploid genome will comprise the nucleic acid sequence encoding the hEPO protein. In other words, the animal is an EPO$^{h/h}$ animal.

In some instances, the non-human animal also expresses the corresponding non-human animal protein. For example, the nucleic acid sequence encoding the human protein, e.g. hEPO, may be located at a site within the animal's genome other than the locus for the non-human animal gene, e.g., mEPO locus. As a second example, the nucleic acid sequence encoding the human protein, e.g. hEPO, may be located at the corresponding animal gene locus, e.g., mEPO locus, wherein it is integrated into the animal gene locus in a manner that allows for the continued expression of the animal coding sequence, e.g. the human coding sequence is inserted upstream or downstream of the animal coding sequence and a 2A peptide sequence or IRES sequence is included between the two coding sequences. As a third example, the nucleic acid sequence encoding the human protein, e.g. hEPO, may be located at the corresponding animal gene locus, e.g., mEPO locus, in a way that disrupts the expression of the animal coding sequence, e.g. as a replacement of some or all of the animal coding sequence, but the non-human animal is bred to be heterozygous for the insertion, i.e. "knock-in", allele, i.e. carrying one knock-in allele and one wild type allele. In other instances, the non-human animal does not express the corresponding non-human animal protein. For example, the nucleic acid sequence encoding the human protein, e.g. hEPO, may be located at the corresponding animal gene locus, e.g., mEPO locus, in a way that disrupts the expression of the animal coding sequence, e.g. as a replacement of some or all of the animal coding sequence, e.g. by replacing non-human animal coding sequence, and the animal is homozygous for the insertion, i.e. "knock-in", allele.

Any non-human mammal animal may be genetically modified according to the subject disclosure. Nonlimiting examples include laboratory animals, domestic animals, livestock, etc., e.g., species such as murine, rodent, canine, feline, porcine, equine, bovine, ovine, non-human primates, etc.; for example, mice, rats, rabbits, hamsters, guinea pigs, cattle, pigs, sheep, goats, and other transgenic animal species, particularly-mammalian species, as known in the art. In other embodiments, the non-human animal may be a bird, e.g., of Galliformes order, such as a chicken, a turkey, a quail, a pheasant, or a partridge; e.g., of Anseriformes order, such as a duck, a goose, or a swan, e.g., of Columbiformes order, such as a pigeon or a dove. In various embodiments, the subject genetically modified animal is a mouse, a rat or a rabbit.

In one embodiment, the non-human animal is a mammal. In some such embodiments, the non-human animal is a small mammal, e.g., of the superfamily Dipodoidea or Muroidea. In one embodiment, the genetically modified animal is a rodent. In one embodiment, the rodent is selected from a mouse, a rat, and a hamster. In one embodiment, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, white-tailed rats, Malagasy rats and mice), Platacanthomyidae (e.g., spiny dormice), and Spalacidae (e.g., mole rats, bamboo rats, and zokors). In a specific embodiment, the genetically modified rodent is selected from a true mouse or rat (family Muridae), a gerbil, a spiny mouse, and a crested rat.

In one embodiment, the subject genetically modified non-human animal is a rat. In one such embodiment, the rat is selected from a Wistar rat, an LEA strain, a Sprague Dawley strain, a Fischer strain, F344, F6, and Dark Agouti. In another embodiment, the rat strain is a mix of two or more strains selected from the group consisting of Wistar, LEA, Sprague Dawley, Fischer, F344, F6, and Dark Agouti.

In another embodiment, the subject genetically modified non-human animal is a mouse, e.g. a mouse of a C57BL strain (e.g. C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, C57BL/Ola, etc.); a mouse of the 129 strain (e.g. 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2); a mouse of the BALB strain; e.g., BALB/c; and the like. See, e.g., Festing et al. (1999) Mammalian Genome 10:836, see also, Auerbach et al (2000) Establishment and Chimera Analysis of 129/SvEv- and C57BL/6-Derived Mouse Embryonic Stem Cell Lines). In one embodiment, the genetically modified mouse is a mix of an aforementioned 129 strain and an aforementioned C57BL/6 strain. In another embodiment, the mouse is a mix of aforementioned 129 strains, or a mix of aforementioned BL/6 strains. In yet another embodiment, the mouse is a mix of a BALB strain and another aforementioned strain.

In some embodiments, the subject genetically modified non-human animal is also immunodeficient. "Immunodeficient," includes deficiencies in one or more aspects of an animal's native, or endogenous, immune system, e.g. the animal is deficient for one or more types of functioning host immune cells, e.g. deficient for non-human B cell number and/or function, non-human T cell number and/or function, non-human NK cell number and/or function, etc.

One method to achieve immunodeficiency in the subject animals is sublethal irradiation. Alternatively, immunodeficiency may be achieved by any one of a number of gene mutations known in the art, any of which may be bred either alone or in combination into the subject genetically modified non-human animals of the present disclosure or which may be used as the source of stem cells into which the genetic modifications of the subject disclosure may be introduced. Non-limiting examples include X-linked SCID, associated with IL2RG gene mutations and characterized by the lymphocyte phenotype T(−) B(+) NK(−); autosomal recessive SCID associated with Jak3 gene mutations and characterized by the lymphocyte phenotype T(−) B(+) NK(−); ADA gene mutations characterized by the lymphocyte phenotype T(−) B(−) NK(−); IL-7R alpha-chain mutations characterized by the lymphocyte phenotype T(−) B(+) NK(+); CD3 delta or epsilon mutations characterized by the lymphocyte phenotype T(−) B(+) NK(+); RAG1 and RAG2 mutations characterized by the lymphocyte phenotype T(−) B(−) NK(+); Artemis gene mutations characterized by the lymphocyte phenotype T(−) B(−) NK(+), CD45 gene mutations characterized by the lymphocyte phenotype T(−) B(+) NK(+); and Prkdc$^{scid}$ mutations characterized by the lymphocyte phenotype T(−), B(−). As such, in some embodiments, the genetically modified immunodeficient non-human animal has one or more deficiencies selected from an IL2 receptor gamma chain (Il2ry$^{y/−}$) deficiency, a Jak3 deficiency, an ADA deficiency, an IL7R deficiency, a CD3 deficiency, a RAG1 and/or RAG2 deficiency, an Artemis deficiency, a CD45 deficiency, and a Prkdc deficiency. These and other animal models of immunodeficiency will be known to the ordinarily skilled artisan, any of which may be used to generate immunodeficient animals of the present disclosure.

In some embodiments, genetically modified non-human animals in accordance with the invention find use as recipients of human hematopoietic cells that are capable of developing human immune cells from engrafted human hematopoietic cells. As such, in some aspects of the invention, the subject genetically modified animal is a genetically modified, immunodeficient, non-human animal that is engrafted with human hematopoietic cells.

Any source of human hematopoietic cells, human hematopoietic stem cells (HSCs) and/or hematopoietic stem progenitor cells (HSPC) as known in the art or described herein may be transplanted into the genetically modified immunodeficient non-human animals of the present disclosure. One suitable source of human hematopoietic cells known in the art is human umbilical cord blood cells, in particular CD34-positive (CD34$^+$) cells. Another source of human hematopoietic cells is human fetal liver. Another source is human bone marrow. Also encompassed are induced pluripotent stem cells (iPSC) and induced hematopoietic stem cells (iHSC) produced by the de-differentiation of somatic cells, e.g., by methods known in the art. Methods for the transplantation of human cells into non-human animals are well-described in the art and elsewhere herein, any of which may be employed by the ordinarily skilled artisan to arrive at the subject genetically modified engrafted non-human animals.

The transplanted human hematopoietic cells give rise in the genetically modified non-human animal to one or more engrafted human cells selected from a human CD34-positive cell, a human hematopoietic stem cell, a human hematopoietic cell, a myeloid progenitor cell, an erythroid progenitor cell, a myeloid cell, a dendritic cell, a monocyte, a neutrophil, a mast cell, an erythrocyte, and a combination thereof. In one embodiment, the human cell is present at 4 months, 5 months, 6 months, 7 months, 8 months, 9 months, 10 months, 11 months, or 12 months after engraftment. In a specific embodiment, the human cells comprise cells of the erythroid lineage.

In some embodiments, the transplanted human hematopoietic cells give rise in the genetically modified non-human animal to an engrafted human hemato-lymphoid system that comprises human hematopoietic stem and progenitor cells, human myeloid progenitor cells, human myeloid cells, human dendritic cells, human monocytes, human granulocytes, human neutrophils, human mast cells, human erythrocytes, human thymocytes, human T cells, human B cells, and human platelets. In one embodiment, the human hemato-lymphoid system is present at 4 months, 5 months, 6 months, 7 months, 8 months, 9 months, 10 months, 11 months, or 12 months after engraftment. In a specific embodiment, the human hemato-lymphoid system comprises cells of the erythroid lineage.

Cells of the erythroid lineage include erythrocytes and cells that give rise to erythrocytes. "Erythrocytes" include mature red blood cells, also referred to red cells or red corpuscles. Cells that give rise to erythrocytes include erythrocyte progenitor cells, i.e., proliferating multipotent cells, and erythrocyte precursors, i.e. proliferating or non-proliferating cells committed to becoming erythrocytes.

Erythrocytes are the major cellular element of the circulating blood and transport oxygen as their principal function. The number of erythrocytes per cubic millimeter of blood is usually maintained between 4.5 and 5.5 million in men and between 4.2 and 4.8 million in women. It varies with age, activity, and environmental conditions. For example, an increase to a level of 8 million/mm$^3$ can normally occur at over 10,000 feet above sea level. An erythrocyte normally lives for 110 to 120 days, when it is removed from the bloodstream and broken down by the reticuloendothelial system. New erythrocytes are produced at a rate of slightly more than 1% a day; thus a constant level is usually maintained. Acute blood loss, hemolytic anemia, or chronic oxygen deprivation may cause erythrocyte production to increase greatly.

Erythrocytes originate from hematopoietic stem cells in the marrow of the long bones, developing into erythrocytes through successive cell stages that include common myeloid progenitor cells (CD123+, CD34+, c-kit+, Flt3+); megakaryocyte-erythroid progenitor cells (CD34+, CD38+, CD45RA−); proerythroblasts (also called pronormoblasts if normal, or promegaloblasts if abnormal; large CD71+, EpoR+, c-kit+, Ter119+ progenitors); basophilic erythroblasts (cytoplasm is basophilic, the nucleus is large with clumped chromatin, and the nucleoli have disappeared); polychromatic erythroblasts (also called an intermediate normoblast, in which the nuclear chromatin shows increased clumping and the cytoplasm begins to acquire hemoglobin and takes on an acidophilic tint); orthochromatic normoblasts (the final stage before nuclear loss, in which the nucleus is small and ultimately becomes a blue-black, homogeneous, structureless mass); and reticulocytes (circulating CD235+, CD71+ cells; the cell is characterized by a meshlike pattern of threads and particles at the former site of the nucleus).

Mature erythrocytes appear on a peripheral smear as biconcave, round or ovoid discs about 6-8 μm in diameter. They contain hemoglobin and have a zone of central pallor due to the cell's biconcavity, and may be readily identified by flow cytometry or immunohistochemistry-based methods by the elevated expression of cell surface markers CD235 and CD59 relative to non-erythroid cells.

As demonstrated in, for example, FIG. 5, Panel A and FIG. 5, Panel B of the present disclosure, the expression of hEPO under the control of an EPO promoter from the genome of an engrafted non-human animal of the present disclosure increases the number of human cells of the erythroid lineage (CD235a+) in the bone marrow on average by about 2-fold (e.g., from about 11% to about 22%). The expression of human Sirpa enhances this effect, resulting in a 3-fold increase or more on average (i.e., from about 11% to about 33%) in the representation of human CD235a+ cells in the bone marrow as compared to animals that do not express either human EPO or human Sirpa (FIG. 5, Panel A). As such, engrafted, immunodeficient, genetically modified non-human animals expressing hEPO of the present disclosure find use in the study of human erythropoiesis and the development of drugs that modulate (e.g. promote or suppress) human erythropoiesis.

Figure 6:
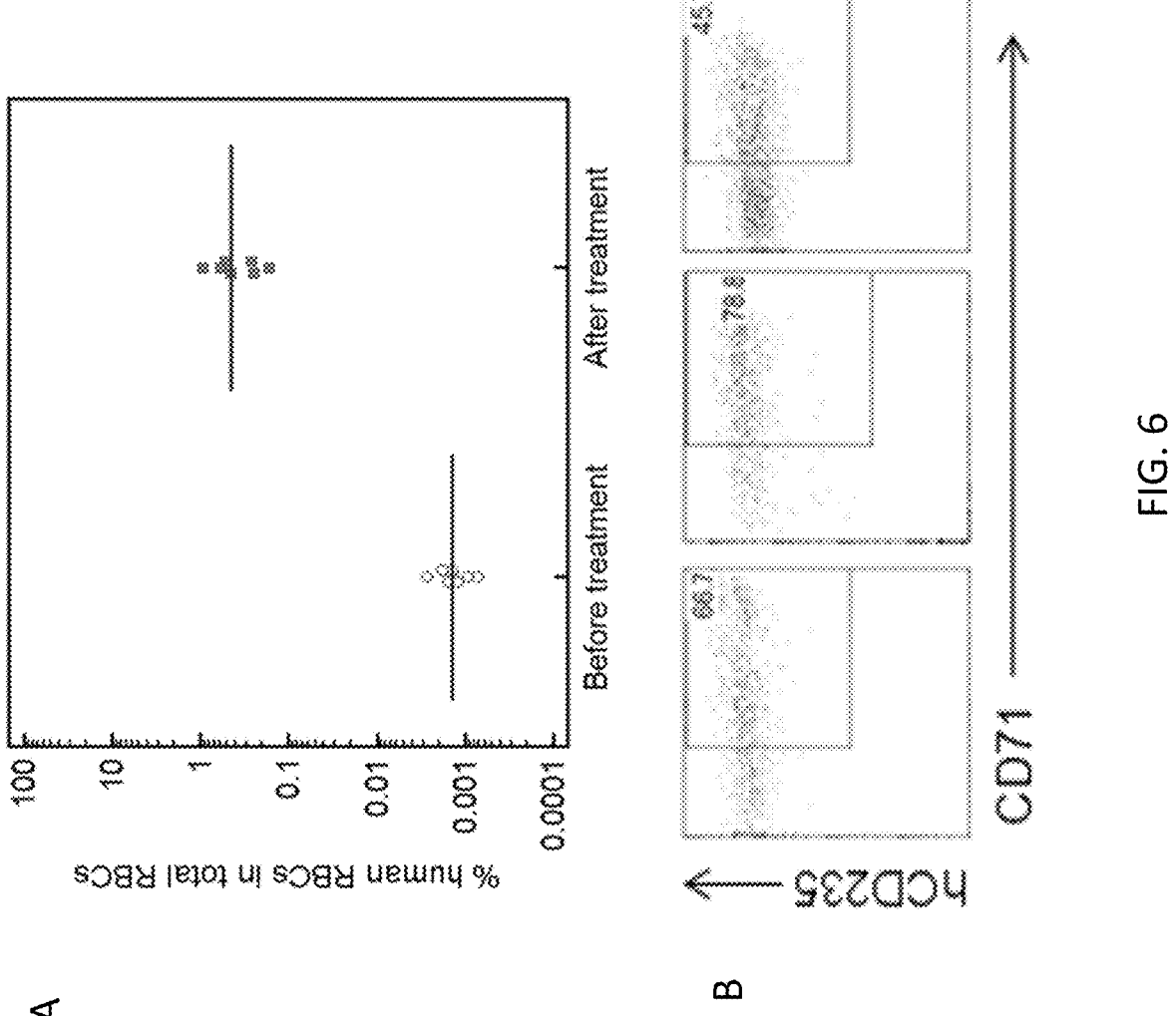
FIG. 6, Panels A and B, demonstrate that clodronate treatment increases circulating human erythroid cells and reticulocytes in HSC-engrafted mice. Seven weeks after HSC-engraftment, SupER-G mice were treated with daily retro-orbital injection of 50 μl clodronate liposome for three to five consecutive days. Frequency of human CD235$^+$ cells (erythrocytes and reticulocytes) (panel A) and CD235$^+$/CD71$^+$ cells (reticulocytes) (panel B) in the peripheral blood was measured by FACS. Panel B: three different mice after treatment with clodronate.
Figure 7:
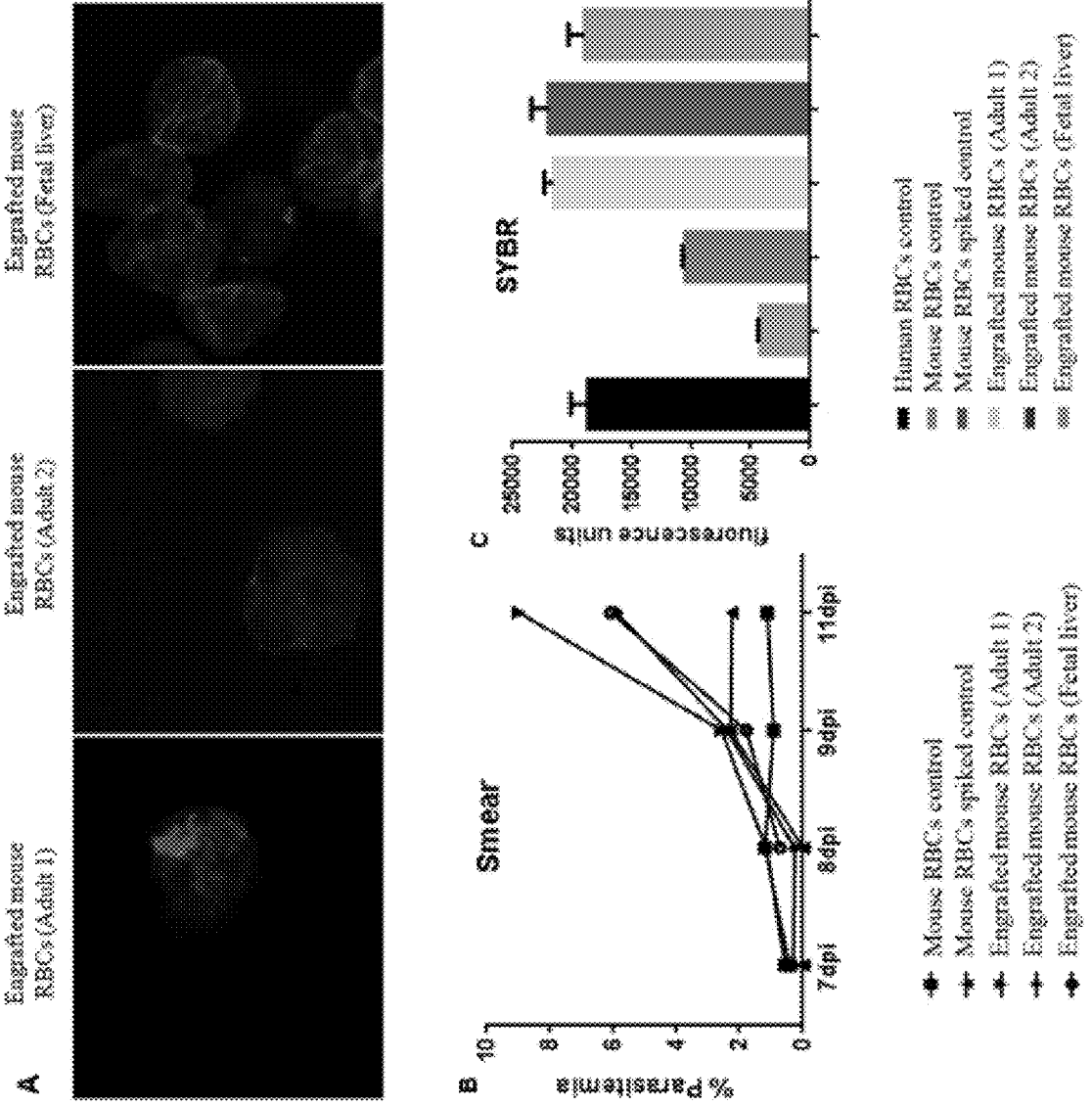
FIG. 7, Panels A-C, illustrate how human RBCs produced from engrafted mice are susceptible to *P. falciparum* infection. SupER-G mice were engrafted with fetal liver or adult HSCs. Seven weeks after engraftment, mice were treated with daily retro-orbital injection of 50 μl clodronate liposomes for three consecutive days before blood collection. Blood samples were then cocultured with purified *P. falciparum* 3D7 blood stage parasites infected RBC (99% purity). Fresh human RBCs were added into the culture 48 hours post infection and infection culture was maintained for additional 10 days. Giemsa staining and quantitative PCR were performed to quantify parasitemia. Human RBCs control: human RBCs; Mouse RBCs control: RBCs from unengrafted mice; Mouse RBCs spiked control: RBCs from unengrafted mice spiked with 0.1% hRBCs. In (Panel A), red: anti-human Band3; Blue: Hoechst. In Panel C, the legend identifiers listed top to bottom correspond to the bar graph x axis from left to right.

Moreover, as demonstrated in, e.g. FIG. 6, clodronate treatment of human HSC-engrafted animals expressing hEPO increases by a thousand-fold the number of CD235+ erythroid cells (including CD71+ reticulocytes, FIG. 6, Panel B) in the peripheral blood of these animals, i.e. to about 1% of the total red blood cells in the periphery, as compared to untreated controls. Importantly, as demonstrated in, e.g. FIG. 7, human red blood cells produced at these engraftment levels in the HSC-engrafted animals expressing human EPO are susceptible to infection with *P. falciparum*. As such, genetically modified non-human animals expressing hEPO as described herein find particular use in the generation of animal models of parasitic infections that target human cells of the erythroid lineage, e.g. pathogens that result in malaria or malaria-like diseases.

Accordingly, in some aspects of the invention, the subject genetically modified animal is a non-human animal engrafted with human hematopoietic cells and comprising an infection by a human pathogen. Of particular interest in these embodiments are human pathogens that target human cells of the erythroid lineage. Non-limiting examples of such pathogens include protozoans of the genera *Plasmodium, Babesia, Theileria*, and the like. As described in greater detail below, the subject genetically modified non-human animal engrafted with human hematopoietic cells may be infected with human pathogen using any appropriate method known in the art or described herein for infecting animals with the pathogens of interest. Animals so infected will typically show signs of parasitaemia including altered morphology by Giemsa-stained blood smear, and a severe decrease (e.g. 50%) in total erythrocyte concentration and anemia.

Methods of Making the Subject Genetically Modified Mice

In some aspects of the invention, methods are provided for making the subject non-human animals of the present disclosure. In practicing the subject methods, a non-human animal is generated which comprises a nucleic acid sequence that encodes a hEPO protein operably linked to an EPO promoter, for example, the non-human animal EPO promoter, e.g. at the EPO locus of the non-human animal genome.

The generation of a non-human animal comprising a nucleic acid sequence that encodes a hEPO protein operably linked to an EPO promoter may be accomplished using any convenient method for the making genetically modified animals, e.g. as known in the art or as described herein.

For example, a nucleic acid encoding the hEPO protein may be incorporated into a recombinant vector in a form suitable for insertion into the genome of the host cell and expression of the human protein in a non-human host cell. In various embodiments, the recombinant vector includes the one or more regulatory sequences operatively linked to the nucleic acid encoding the human protein in a manner which allows for transcription of the nucleic acid into mRNA and translation of the mRNA into the human protein, as described above. It will be understood that the design of the vector may depend on such factors as the choice of the host cell to be transfected and/or the amount of human protein to be expressed.

Any of various methods may then be used to introduce the human nucleic acid sequence into an animal cell to produce a genetically modified animal that expresses the human gene. Such techniques are well-known in the art and include, but are not limited to, pronuclear microinjection, transformation of embryonic stem cells, homologous recombination and knock-in techniques. Methods for generating genetically modified animals that can be used include, but are not limited to, those described in Sundberg and Ichiki (2006, Genetically Engineered Mice Handbook, CRC Press), Hofker and van Deursen (2002, Genetically modified Mouse Methods and Protocols, Humana Press), Joyner (2000, Gene Targeting: A Practical Approach, Oxford University Press), Turksen (2002, Embryonic stem cells: Methods and Protocols in Methods Mol Biol., Humana Press), Meyer et al. (2010, Proc. Nat. Acad. Sci. USA 107:15022-15026), and Gibson (2004, A Primer Of Genome Science $2^{nd}$ ed. Sunderland, Massachusetts: Sinauer), U.S. Pat. No. 6,586,251, Rathinam et al. (2011, Blood 118:3119-28), Willinger et al., (2011, Proc Natl Acad Sci USA, 108:2390-2395), Rongvaux et al., (2011, Proc Natl Acad Sci USA, 108:2378-83) and Valenzuela et al. (2003, Nat Biot 21:652-659).

For example, the subject genetically modified animals can be created by introducing the nucleic acid encoding the human protein into an oocyte, e.g., by microinjection, and allowing the oocyte to develop in a female foster animal. In preferred embodiments, the expression is injected into fertilized oocytes. Fertilized oocytes can be collected from superovulated females the day after mating and injected with the expression construct. The injected oocytes are either cultured overnight or transferred directly into oviducts of 0.5-day p.c. pseudopregnant females. Methods for superovulation, harvesting of oocytes, expression construct injection and embryo transfer are known in the art and described in Manipulating the Mouse Embryo (2002, A Laboratory Manual, 3rd edition, Cold Spring Harbor Laboratory Press). Offspring can be evaluated for the presence of the introduced nucleic acid by DNA analysis (e.g., PCR, Southern blot, DNA sequencing, etc.) or by protein analysis (e.g., ELISA, Western blot, etc.).

As another example, the construct comprising the nucleic acid sequence encoding the human protein may be transfected into stem cells (e.g., ES cells or iPS cells) using well-known methods, such as electroporation, calcium-phosphate precipitation, lipofection, etc. The cells can be evaluated for the presence of the introduced nucleic acid by DNA analysis (e.g., PCR, Southern blot, DNA sequencing, etc.) or by protein analysis (e.g., ELISA, Western blot, etc.). Cells determined to have incorporated the expression construct can then be introduced into preimplantation embryos. For a detailed description of methods known in the art useful for the compositions and methods of the invention, see Nagy et al., (2002, Manipulating the Mouse Embryo: A Laboratory Manual, 3rd edition, Cold Spring Harbor Laboratory Press), Nagy et al. (1990, Development 110:815-821), U.S. Pat. Nos. 7,576,259, 7,659,442, 7,294,754, and Kraus et al. (2010, Genesis 48:394-399).

Additionally, as described in some of the Examples below, a nucleic acid construct may be constructed using VELOCIGENE® genetic engineering technology (see, e.g., Valenzuela et al. (2003) High throughput engineering of the mouse genome coupled with high-resolution expression analysis, Nature Biotech. 21(6): 652-59 and U.S. Pat. No. 6,586,251), introduced into stem cells (e.g., ES cells), and correctly targeted clones determined using loss-of-allele and gain-of-allele assays (Valenzuela et al., supra); correctly targeted ES cells may be used as donor ES cells for introduction into an 8-cell stage mouse embryo using the VELOCIMOUSE® method (see, e.g., U.S. Pat. No. 7,294, 754 and Poueymirou et al. 2007, F0 generation mice that are essentially fully derived from the donor gene-targeted ES cells allowing immediate phenotypic analyses Nature Biotech. 25(1):91-99).

Genetically modified founder animals can be bred to additional animals carrying the genetic modification. Genetically modified animals carrying a nucleic acid encoding the human protein(s) of the present disclosure can further be bred to other genetically modified animals carrying other genetic modifications, e.g. hSIRPa knock-in mice, hIL-3 knock-in mice, hGM-CSF knock-in mice, hM-CSF knock-in mice, hTPO knock-in mice, hIL-6 knock-in mice, and the like, or be bred to knockout animals, e.g., a non-human animal that is deficient for one or more proteins, e.g. does not express one or more of its genes, e.g. a Rag2-deficient animal, an Il2rg-deficient animal.

In another embodiment, stem cells, e.g., ES cells, may be generated such that they comprise several genetic modifications, e.g., humanizations or gene deletions described herein, and such stem cells may be introduced into an embryo to generate genetically modified animals with several genetic modifications.

As discussed above, in some embodiments, the subject genetically modified non-human animal is an immunodeficient animal. Genetically modified non-human animals that are immunodeficient and comprise one or more human proteins, e.g. hEPO, hSIRPa, hIL-3, hGM-CSF, hM-CSF, and/or hTPO, may be generated using any convenient method for the generation of genetically modified animals, e.g. as known in the art or as described herein. For example, the generation of the genetically modified immunodeficient animal can be achieved by introduction of the nucleic acid encoding the human protein into an oocyte or stem cells comprising a mutant SCID gene allele that, when homozygous, will result in immunodeficiency as described in greater detail above and in the working examples herein. Mice are then generated with the modified oocyte or ES cells using, e.g. methods described herein and known in the art, and mated to produce the immunodeficient mice comprising the desired genetic modification. As another example, genetically modified non-human animals can be generated in an immunocompetent background, and crossed to an animal comprising a mutant gene allele that, when hemizygous or homozygous, will result in immunodeficiency, and the progeny mated to create an immunodeficient animal expressing the at least one human protein of interest.

In some embodiments, the genetically modified mouse is treated so as to eliminate endogenous hematopoietic cells that may exist in the mouse. In one embodiment, the treatment comprises irradiating the genetically modified mouse. In a specific embodiment, newborn genetically modified mouse pups are irradiated sublethally. In a specific embodiment, newborn pups are irradiated 2×200 cGy with a four hour interval.

Various embodiments of the invention provide genetically modified animals that include a human nucleic acid in substantially all of their cells, as well as genetically modified animals that include a human nucleic acid in some, but not all their cells. In some instances, e.g. targeted recombination, one copy of the human nucleic acid will be integrated into the genome of the genetically modified animals. In other instances, e.g. random integration, multiple copies, adjacent or distant to one another, of the human nucleic acid may be integrated into the genome of the genetically modified animals.

Thus, in some embodiments, the subject genetically modified non-human animal may be an immunodeficient animal comprising a genome that includes a nucleic acid encoding a human polypeptide operably linked to the corresponding non-human animal promoter, wherein the animal expresses the encoded human polypeptide. In other words, the subject genetically modified immunodeficient non-human animal comprises a genome that comprises a nucleic acid encoding at least one human polypeptide, wherein the nucleic acid is operably linked to the corresponding non-human promoter and a polyadenylation signal, and wherein the animal expresses the encoded human polypeptide.

As discussed above, in some embodiments, the subject genetically modified non-human animal is engrafted with human hematopoietic cells. Any source of human hematopoietic cells, human hematopoietic stem cells (HSCs) and/or hematopoietic stem progenitor cells (HSPC) as known in the art or described herein may be transplanted into the genetically modified non-human animals of the present disclosure, e.g. umbilical cord blood, fetal liver, bone marrow, iPSCs, etc. In one embodiment, the hematopoietic cells are selected from human umbilical cord blood cells and human fetal liver cells. The amount of cells to be transplanted will be well understood by the ordinarily skilled artisan or may be empirically determined. In one embodiment, engraftment is with about $1$-$2 \times 10^5$ human CD34+ cells. Cells may be transplanted into the host subject non-human animal using any convenient technique known in the art, for example, tail vein injection, retro-orbital injection, injection into neonatal liver, and the like. Cells may be transplanted into the host in any convenient buffered solution, e.g. PBS, Dulbecco's modified medium, Iscove's modified medium, and the like. In some instances, the animal may be irradiated before being engrafted, e.g. as described above, to improve immunodeficiency.

Human hematopoietic cells so engrafted give rise to one or more human cells selected from a CD34+ cell, a hematopoietic stem cell, a hematopoietic cell, a myeloid precursor cell, a myeloid cell, a dendritic cell, a monocyte, a granulocyte, a neutrophil, a mast cell, a thymocyte, a T cell, a B cell, a platelet, an erythrocyte, and a combination thereof. In one embodiment, the human cell is present at 4 months, 5 months, 6 months, 7 months, 8 months, 9 months, 10 months, 11 months, or 12 months after engraftment. Any of a number of assays may be performed to confirm that engraftment is successful, including, for example, flow cytometry assays for the various human hematopoietic cells of interest, blood smears, and immunohistochemistry.

As discussed above, in some embodiments, the subject genetically modified non-human animal engrafted with human hematopoietic cells is infected with a human pathogen. Of particular interest in these embodiments are human pathogens that target human cells of the erythroid lineage. Non-limiting examples of such pathogens include protozoans of the genera *Plasmodium* sp., *Babesia* sp., *Theileria* sp., and the like. In some embodiments, the strain of pathogen used is a naturally occurring strain. In certain embodiments, the strain used has been selected in vivo for its competence to grow reproducibly in human erythrocyte-engrafted immunodeficient mice, e.g. *P. falciparum* strains Pf3D7$^{0087/N9}$ or Pf3D7$^{0087/N5}$.

The subject engrafted immunodeficient animals may be infected using any method known in the art for infecting animals with pathogen that targets cells of the erythroid lineage. For example, the subject engrafted immunodeficient animals may be inoculated intraperitoneally with parasitized red blood cells (PRBCs). See, e.g., Badell et al. (2000) Human malaria in immunocompromised mice: an in vivo model to study defense mechanisms against *Plasmodium falciparum*. JEM 192(11):1653-1660; and Moreno et al. (2006) The course of infections and pathology in immuno-modulated NOD/LtSz-SCID mice inoculated with *Plasmodium falciparum* laboratory lines and clinical isolates. Int. J. Parasitol. 36:361-369. As another example, the subject engrafted immunodeficient animals may be inoculated intra-vascularly with parasitized red blood cells. See, e.g., Angulo-Barturen et al. (2008) A murine model of falci-parum-malaria by in vivo selection of competent strains in non-myelodepleted mice engrafted with human erythro-cytes. PLoS One 3:e2252; and Jimenez-Diaz et al. (2009) Improved murine model of malaria using *Plasmodium fal-ciparum* competent strains and non-myelodepleted NOD-scid IL2Rg$^{null}$ mice engrafted with human erythrocytes. Antimicrob Agents Chemother 53:4533-4536. In some embodiments, the infection is produced by injecting parasite into the non-human animal, i.e. not in the context of eryth-roid cells. In some embodiments, the subject engrafted immunodeficient animals are chemically depleted in vivo of phagocytic cells prior to and/or during infection. In such embodiments, any chemotherapeutic agent that selectively depletes host phagocytic cells may be administered to the subject animals, including, for example, clodronate, e.g. as described in the working examples herein; dicholorometh-ylene diphosphonate, e.g. as described in Badell et al. supra, and Moreno et al. supra; monoclonal antibody specific for polymorphonuclear neutrophils, e.g. NIMP-R14, as described in Badell et al. supra and Moreno et al., supra; and the like.

Percent parasitaemia in the infected genetically modified non-human animals of the present disclosure can be esti-mated by any convenient method in the art, e.g. microscopi-cally from a Giemsa-stained blood smear, e.g. 3 days after injection; or by flow cytometry, e.g. by measurement of the emission of the nucleic acid dye YOYO-1 or of the cell-permeant dye SYTO-16, e.g. in the presence or absence of TER-119 mAb. See, e.g., Jimenez-Diaz et al. Quantitative measurement of *Plasmodium*-infected erythrocytes in murine models of malaria by flow cytometry using bidimen-sional assessment of SYTO-16 fluorescence. Cytometry A 2009, 75:225-235.

Use of the Subject Genetically Modified Mice

The ability to study human tissue in an in vivo setting in mice has opened a range of possible avenues of research. Major limitations have hindered the application of the approach and of these one of the most important deficiencies has been the inability of mouse factors to support human cells. Indeed, in the immune system, many essential factors required for human immune cell development and function are species-specific and cannot be effectively provided by the mouse. It was therefore decided to follow a strategy of replacing the mouse genes with their human counterparts, enabling the better development and function of human cells and potentially disabling the same of the corresponding mouse cells. By applying this concept to human cytokine EPO, it is shown herein that replacement of nucleic acid sequence encoding the mouse EPO protein with nucleic acid sequence encoding human EPO protein improves the devel-opment and function of cells of the erythroid lineage in the engrafted human immune system in mice.

For example, the working examples at, e.g. FIG. 5, demonstrate that the expression of hEPO from a nucleic acid sequence under the control of an EPO promoter at the genome of a non-human animal increases the number of human cells of the erythroid lineage (CD235a+) that develop in the bone marrow of human HSC-engrafted animals by about 2-fold (i.e., from about 11% to about 22%). The expression of human Sirpa enhances this effect, resulting in a 3-fold total increase (i.e., from about 11% to about 33%) in the representation of human CD235a+ cells in the bone marrow as compared to animals that do not express either human EPO or human Sirpa (FIG. 4*a*). Moreover, as dem-onstrated in, e.g. FIG. 6, clodronate treatment of human HSC-engrafted animals expressing human EPO increases by a thousand-fold the number of CD235+ erythroid cells (including CD71+ reticulocytes, FIG. 6, Panel B) in the peripheral blood of these animals, i.e. to about 1% of the total red blood cells, over untreated controls. Importantly, as demonstrated in, e.g. FIG. 7, human red blood cells pro-duced at these engraftment levels in the HSC-engrafted animals expressing human EPO are susceptible to infection with *Plasmodium* sp. such as *P. falciparum*. Accordingly, genetically modified non-human animals expressing human EPO as described herein find particular use in the generation of animals that are susceptible to infection with *Plasmodium* sp., or that will better support human erythrocytes that are acutely grafted into the animal prior to infection in current rodent models.

As such, the genetically modified non-human animals of the present disclosure find many uses in the art. For example, engrafted genetically modified animals of the present dis-closure are useful for studying human erythropoiesis and the function of human erythrocytes. As another example, engrafted genetically modified mice of the present disclo-sure provide a useful system for screening candidate agents for desired activities in vivo, for example, to identify agents that are able to modulate (i.e., promote or suppress) human erythropoiesis and/or the function of human erythrocytes, e.g. in a healthy or a diseased state, e.g. as cancerous cells, during pathogen infection, etc., for example to identify novel therapeutics; or as another example, to identify agents that are toxic to human cells of the erythroid lineage, and to identify agents that prevent against, mitigate, or reverse the toxic effects of toxic agents on human cells of the erythroid lineage; etc. As yet another example, engrafted genetically modified animals of the present disclosure provide a useful system for predicting the responsiveness of an individual to a disease therapy, e.g. by providing an in vivo platform for screening the responsiveness of an individual's immune system to an agent, e.g. a therapeutic agent, to predict the responsiveness of an individual to that agent.

As one non-limiting example, engrafted genetically modi-fied mice of the present disclosure find use in the generation of mouse models of pathogen infection by parasites that target human erythroid cells, e.g. *Plasmodium, Babesia, Theileria*, and the like. Such mouse models of infection will be useful in both research, e.g. to better understand the progression of infection in humans, and in drug discovery, e.g. to identify candidate agents that protect against or treat infection by such parasites.

Protozoans of the genus *Plasmodium* are the cause of malaria in humans. Malaria begins with a bite from an infected *Anopheles* mosquito, which introduces the protozoa via its saliva into the circulatory system, and ultimately to the liver where they mature and reproduce. The protozoa then enter the bloodstream and infect cells of the erythroid lineage at various stages of maturation.

Five species of *Plasmodium* can infect and be transmitted by humans. The vast majority of deaths are caused by *P. falciparum*, while *P. vivax, P. ovale*, and *P. malariae* cause a generally milder form of malaria that is rarely fatal. This believed to be due at least in part to the type(s) of cells targeted by each species: *P. falciparum* grows in red blood cells (RBCs) of all maturities whereas, for example, *P. vivax* is restricted to growth in reticulocytes, which represent only approximately 1%-2% of total RBCs in the periphery. In addition, *P. falciparum* causes severe malaria via a distinctive property not shared by any other human malaria, namely, that of sequestration. Within the 48-hour asexual blood stage cycle, the mature forms change the surface properties of infected red blood cells, causing them to stick to blood vessels (a process called cytoadherence). This leads to obstruction of the microcirculation and results in dysfunction of multiple organs.

Symptoms of malaria include fever, chills, headache, sweats, fatigue, anemia, nausea, dry (nonproductive) cough, muscle and/or back pain, and an enlarged spleen. Other symptoms and complications associated with malaria include brain infection (cerebritis), hemolytic anemia, kidney failure, liver failure, meningitis, pulmonary edema, and hemorrhaging from the spleen. Generally, an individual at risk for developing malaria will begin to show symptoms 7 days or more after infection, e.g., 9 to 14 days after the initial infection by *P. falciparum,* 12 to 18 days after the initial infection by *P. vivax* or *P. ovale,* 18 to 40 days after the initial infection by *P. malariae*, or 11 to 12 days after the initial infection by *P. knowlesi*. Anti-malaria agents used in the art to treat or prevent malaria include chloroquine, quinidine, doxycycline, tetracycline, clindamycin, atovaquone plus proguanil (Malarone), Mefloquine, artesunate, and pyrimethamine plus sulfadoxine (Fansidar).

Methods for determining if a subject has been infected with *Plasmodium* are well known in the art, and include, for example, microscopic examination of blood using blood films, with antigen-based Rapid Diagnostic Tests (RDT), e.g., immunochromatography-based RDTs, by detection of parasite DNA by polymerase chain reaction (PCR), etc. Any convenient method may be used to determine if the human red blood cells of the subject have been infected with the pathogen.

Another example of pathogens of interest are protozoans of the genus *Babesia*. *Babesia* infection results in a malaria-like disease called babesiosis. Babesiosis is a vector-borne illness usually transmitted by *Ixodes scapularis* ticks. The disease is typically caused by *B. microti* in humans, *B. canis rossi* and *B. canis canis* in dogs, *B. bovis* in cows, and *B. bigemina* in cattle. *Babesia microti*, which infects humans, uses the same tick vector as Lyme disease and ehrlichiosis, and may occur in conjunction with these other diseases. The protozoa can also be transmitted by blood transfusion.

In humans, babesiosis may be asymptomatic, or characterized by symptoms ranging from mild fever and diarrhea to high fever, shaking chills, and severe anemia. In severe cases, organ failure, including respiratory distress syndrome, may occur. Severe cases occur mostly in people who have had a splenectomy, or persons with an immunodeficiency, such as HIV/AIDS patients. Treatment typically comprises a two-drug regimen of quinine and clindamycin, or of atovaquone and azithromycin. In instances where babesiosis appears life-threatening, a blood exchange transfusion is performed, in which infected red blood cells are removed and replaced with uninfected ones.

Definitive diagnosis of infection by *Babesia* is by the identification of the parasite on a Giemsa-stained thin blood smear. The parasite appears in erythrocytes as paired merozoites forming the "Maltese cross formation" in humans or "two pears hanging together" in animals. Other diagnostic methods include PCR of peripheral blood, and serologic testing for antibodies (IgG, IgM) against *Babesia.*

Yet another malaria-like disease, theileriosis, is caused by protozoans of the genus *Theileria*. In humans, theileriosis is caused by *T. microti*; in horses, by *T. equi* ("Equine Piroplasmosis"); in sheep and goats, by *T. lestoquardi*; and in cattle, African buffalo, water buffalo, and water bucks, by *T. annulata* ("Tropical Theileriosis", also known as "Mediterranean theileriosis") or *T. parva* ("East Coast fever", also known as "Corridor disease"). Theirleriosis is transmitted to the host by various tick species including *Ixodes scapularis, Rhipicephalus, Dermacentor, Haemaphysalis*, and *Hyalomma*. The organism reproduces in the tick as it progresses through its life stage, and matures and enters the saliva after the tick attaches to a host. Usually, the tick must be attached for a few days before it becomes infective. However, if environmental temperatures are high, infective sporozoites can develop in ticks on the ground, and may enter the host within hours of attachment.

Theirleriosis in humans typically presents as fever and hemolysis. Definitive diagnosis of infection by *Theileria* is by the identification of the parasite on a Giemsa-stained thin blood smear.

Engrafted genetically modified animals of the present disclosure find use in screening candidate agents to identify those that will prevent (e.g. vaccines) or treat infections by *Plasmodium, Babesia, Theileria*, and other parasites that target human erythrocytes. The terms "treatment", "treating" and the like are used herein to generally include obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein include any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. Candidate agents of interest as anti-parasitic therapeutics include those that may be administered before, during or after the infection with the parasite, and which, when administered in an effective amount, inhibit the effects of a parasite on an individual (i.e. the host), for example, by killing the parasite or the cell infected by the parasite, by preventing the propagation of the parasite, by preventing the production or action of an agent produced by the parasite that is toxic to the individual (i.e. a toxin), etc. The terms "individual," "subject," "host," and "patient," are used interchangeably herein and include any mammalian subject for whom diagnosis, treatment, or therapy is desired, particularly humans.

In screening assays for biologically active agents, a human hematopoietic cell-engrafted genetically modified non-human animal of the present disclosure, e.g. an engrafted Rag2$^{-/-}$Il2rg$^{null}$Epo$^{h/m}$ mouse, an engrafted Rag2$^{-/-}$Il2rg$^{null}$Tpo$^{h/h}$Il3/Gmcsf$^{h/h}$Epo$^{h/m}$SIRPα$^{h/h}$ ("TIES") mouse, an engrafted Rag2$^{-/-}$IL2rg$^{y/-}$Tpo$^{h/h}$Mcsf$^{h/}$$_{h}$Il3$^{h/h}$Gmcsf$^{h/h}$Epo$^{h/h}$hSIRPα+("MISTER-G") mouse, an engrafted Rag2$^{--}$Il2rg$^{null}$Tpo$^{h/h}$Mcsf$^{h/h}$Il3/Gmcsf$^{h/h}$Epo$^{h/}$$_{h}$SIRPα-tg+ ("SupER-G") mouse, etc. is contacted with a candidate agent of interest and the effect of the candidate agent is assessed by monitoring one or more output parameters. These output parameters may be reflective of the viability of the cells, e.g. the total number of hematopoietic cells or the number of cells of a particular hematopoietic cell type, or of the apoptotic state of the cells, e.g. the amount of DNA fragmentation, the amount of cell blebbing, the amount of phosphatidylserine on the cell surface, and the like by methods that are well known in the art. Alternatively or additionally, the output parameters may be reflective of the differentiation capacity of the cells, e.g. the proportions of differentiated cells and differentiated cell types. Alternatively or additionally, the output parameters may be reflective of the function of the cells, e.g. the cytokines and chemokines produced by the cells, the antibodies (e.g. amount or type) produced by the cells, the ability of the cells to home to and extravasate to a site of challenge, the ability of the cells to modulate, i.e. promote or suppress, the activity of other cells in vitro or in vivo, the ability to take up hemoglobin, etc. Yet other parameters may be reflective of the effect of the agent on infection, e.g. pathogen infection in the animal, e.g. the titer of pathogen in the mouse, etc., as relevant to the studies being performed.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Candidate agents of interest for screening include known and unknown compounds that encompass numerous chemical classes, primarily organic molecules, which may include organometallic molecules, inorganic molecules, genetic sequences, vaccines, antibiotics or other agents suspected of having antibiotic properties, peptides, polypeptides, antibodies, agents that have been approved pharmaceutical for use in a human, etc. An important aspect of the invention is to evaluate candidate drugs, including toxicity testing; and the like.

Candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof. Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition.

Also included are toxins, and biological and chemical warfare agents, for example see Somani, S. M. (Ed.), "Chemical Warfare Agents," Academic Press, New York, 1992).

Candidate agents of interest for screening also include nucleic acids, for example, nucleic acids that encode siRNA, shRNA, antisense molecules, or miRNA, or nucleic acids that encode polypeptides. Many vectors useful for transferring nucleic acids into target cells are available. The vectors may be maintained episomally, e.g. as plasmids, minicircle DNAs, virus-derived vectors such cytomegalovirus, adenovirus, etc., or they may be integrated into the target cell genome, through homologous recombination or random integration, e.g. retrovirus derived vectors such as MMLV, HIV-1, ALV, etc. Vectors may be provided directly to the subject cells. In other words, the pluripotent cells are contacted with vectors comprising the nucleic acid of interest such that the vectors are taken up by the cells.

Methods for contacting cells, e.g. cells in culture or cells in a mouse, with nucleic acid vectors, such as electroporation, calcium chloride transfection, and lipofection, are well known in the art. Alternatively, the nucleic acid of interest may be provided to the cells via a virus. In other words, the cells are contacted with viral particles comprising the nucleic acid of interest. Retroviruses, for example, lentiviruses, are particularly suitable to the method of the invention. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein to be incorporated into the capsid, this envelope protein determining the specificity of the viral particle for the cells. Envelope proteins are of at least three types, ecotropic, amphotropic and xenotropic. Retroviruses packaged with ecotropic envelope protein, e.g. MMLV, are capable of infecting most murine and rat cell types, and are generated by using ecotropic packaging cell lines such as BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse, and are generated by using amphotropic packaging cell lines such as PA12 (Miller et al. (1985) Mol. Cell. Biol. 5:431-437); PA317 (Miller et al. (1986) Mol. Cell. Biol. 6:2895-2902); GRIP (Danos et al. (1988) PNAS 85:6460-6464). Retroviruses packaged with xenotropic envelope protein, e.g. AKR env, are capable of infecting most mammalian cell types, except murine cells. The appropriate packaging cell line may be used to ensure that the cells of interest—in some instance, the engrafted cells, in some instance, the cells of the host, i.e. the genetically modified animal—are targeted by the packaged viral particles.

Vectors used for providing nucleic acid of interest to the subject cells will typically comprise suitable promoters for driving the expression, that is, transcriptional activation, of the nucleic acid of interest. This may include ubiquitously acting promoters, for example, the CMV-β-actin promoter, or inducible promoters, such as promoters that are active in particular cell populations or that respond to the presence of drugs such as tetracycline. By transcriptional activation, it is intended that transcription will be increased above basal levels in the target cell by at least about 10 fold, by at least about 100 fold, more usually by at least about 1000 fold. In addition, vectors used for providing reprogramming factors to the subject cells may include genes that must later be removed, e.g. using a recombinase system such as Cre/Lox, or the cells that express them destroyed, e.g. by including genes that allow selective toxicity such as herpesvirus TK, bcl-xs, etc.

Candidate agents of interest for screening also include polypeptides. Such polypeptides may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. Additionally or alternatively, such polypeptides may be formulated for improved stability. For example, the peptides may be PEGylated, where the polyethyleneoxy group provides for enhanced lifetime in the blood stream. The polypeptide may be fused to another polypeptide to provide for added functionality, e.g. to increase the in vivo stability. Generally such fusion partners are a stable plasma protein, which may, for example, extend the in vivo plasma half-life of the polypeptide when present as a fusion, in particular wherein such a stable plasma protein is an immunoglobulin constant domain. In most cases where the stable plasma protein is normally found in a multimeric form, e.g., immunoglobulins or lipoproteins, in which the same or different polypeptide chains are normally disulfide and/or noncovalently bound to form an assembled multichain polypeptide, the fusions herein containing the polypeptide also will be produced and employed as a multimer having substantially the same structure as the stable plasma protein precursor. These multimers will be homogeneous with respect to the polypeptide agent they comprise, or they may contain more than one polypeptide agent.

The candidate polypeptide agent may be produced from eukaryotic cells, or may be produced by prokaryotic cells. It may be further processed by unfolding, e.g. heat denaturation, DTT reduction, etc. and may be further refolded, using methods known in the art. Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine. The polypeptides may have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

The candidate polypeptide agent may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like. Alternatively, the candidate polypeptide agent may be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In some cases, the candidate polypeptide agents to be screened are antibodies. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. The specific or selective fit of a given structure and its specific epitope is sometimes referred to as a "lock and key" fit. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammal, chicken, other avians, etc., are considered to be "antibodies." Antibodies utilized in the present invention may be either polyclonal antibodies or monoclonal antibodies. Antibodies are typically provided in the media in which the cells are cultured. Antibody production and screen is discussed in greater detail below.

Candidate agents may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Candidate agents are screened for biological activity by administering the agent to at least one and usually a plurality of samples, sometimes in conjunction with samples lacking the agent. The change in parameters in response to the agent is measured, and the result evaluated by comparison to reference samples, e.g. in the presence and absence of the agent, obtained with other agents, etc. In instances in which a screen is being performed to identify candidate agents that will prevent, mitigate or reverse the effects of a pathogen, the screen is typically performed in the presence of the pathogenic agent, where the pathogenic agent is added at the time most appropriate to the results to be determined. For example, in cases in which the protective/preventative ability of the candidate agent is tested, the candidate agent may be added before the pathogen, simultaneously with the pathogen, or subsequent to infection by the pathogen. As another example, in cases in which the ability of the candidate agent to reverse the effects of a pathogen is tested, the candidate agent may be added subsequent to infection with the pathogen. As mentioned above, in some instances, the "sample" is a genetically modified non-human animal that has been engrafted with cells, e.g. the candidate agent is provided to an immunodeficient animal, e.g. mouse, comprising a nucleic acid encoding human EPO operably linked to an EPO promoter that has been engrafted with human hematopoietic cells. In some instances, the sample is the human hematopoietic cells to be engrafted, i.e. the candidate agent is provided to cells, e.g. reticulocytes, erythrocytes, etc., prior to engraftment into the immunodeficient genetically modified animal.

If the candidate agent is to be administered directly to the engrafted genetically modified animal, the agent may be administered by any of a number of well-known methods in the art for the administration of peptides, small molecules and nucleic acids to mice. For example, the agent may be administered orally, mucosally, topically, intradermally, or by injection, e.g. intraperitoneal, subcutaneous, intramuscular, intravenous, or intracranial injection, and the like. The agent may be administered in a buffer, or it may be incorporated into any of a variety of formulations, e.g. by combination with appropriate pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal. Such pharmaceutical vehicles can be lipids, e.g. liposomes, e.g. liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. Pharmaceutical compositions may be formulated into preparations in solid, semi-solid, liquid or gaseous forms, such as tablets, capsules, powders, granules, ointments, solutions, suppositories, injections, inhalants, gels, microspheres, and aerosols. The agent may be systemic after administration or may be localized by the use of regional administration, intramural administration, or use of an implant that acts to retain the active dose at the site of implantation. The active agent may be formulated for immediate activity or it may be formulated for sustained release. For some conditions, particularly central nervous system conditions, it may be necessary to formulate agents to cross the blood-brain barrier (BBB). One strategy for drug delivery through the blood-brain barrier (BBB) entails disruption of the BBB, either by osmotic means such as mannitol or leukotrienes, or biochemically by the use of vasoactive substances such as bradykinin. A BBB disrupting agent can be co-administered with the agent when the compositions are administered by intravascular injection. Other strategies to go through the BBB may entail the use of endogenous transport systems, including Caveolin-1 mediated transcytosis, carrier-mediated transporters such as glucose and amino acid carriers, receptor-mediated transcytosis for insulin or transferrin, and active efflux transporters such as p-glycoprotein. Active transport moieties may also be conjugated to the therapeutic compounds for use in the invention to facilitate transport across the endothelial wall of the blood vessel. Alternatively, drug delivery of agents behind the BBB may be by local delivery, for example by intrathecal delivery, e.g. through an Ommaya reservoir (see e.g. U.S. Pat. Nos. 5,222,982 and 5,385,582, incorporated herein by reference); by bolus injection, e.g. by a syringe, e.g. intravitreally or intracranially; by continuous infusion, e.g. by cannulation, e.g. with convection (see e.g. US Application No. 20070254842, incorporated here by reference); or by implanting a device upon which the agent has been reversably affixed (see e.g. US Application Nos. 20080081064 and 20090196903, incorporated herein by reference).

If the agent(s) are provided to cells prior to engraftment, the agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

An analysis of the response of cells in the engrafted genetically modified animal to the candidate agent may be performed at any time following treatment with the agent. For example, the cells may be analyzed 1, 2, or 3 days, sometimes 4, 5, or 6 days, sometimes 8, 9, or 10 days, sometimes 14 days, sometimes 21 days, sometimes 28 days, sometimes 1 month or more after contact with the candidate agent, e.g. 2 months, 4 months, 6 months or more. In some embodiments, the analysis comprises analysis at multiple time points. The selection of the time point(s) for analysis will be based upon the type of analysis to be performed, as will be readily understood by the ordinarily skilled artisan.

The analysis may comprise measuring any of the parameters described herein or known in the art for measuring cell viability, cell proliferation, cell identity, cell morphology, and cell function, particularly as they may pertain to cells of the immune cells. For example, flow cytometry may be used to determine the total number of hematopoietic cells or the number of cells of a particular hematopoietic cell type. Histochemistry or immunohistochemistry may be performed to determine the apoptotic state of the cells, e.g. terminal deoxynucleotidyl transferase dUTP nick end labeling (TUNEL) to measure DNA fragmentation, or immunohistochemistry to detect Annexin V binding to phosphatidylserine on the cell surface. Flow cytometry may also be employed to assess the proportions of differentiated cells and differentiated cell types, e.g. to determine the ability of hematopoietic cells to survive and/or differentiate in the presence of agent. ELISAs, Westerns, and Northern blots may be performed to determine the levels of cytokines, chemokines, immunoglobulins, etc. expressed in the engrafted genetically modified mice, e.g. to assess the function of the engrafted cells, to assess the survival of erythrocytes, etc. In vivo assays to test the function of immune cells, as well as assays relevant to particular diseases or disorders of interest such as anemia, e.g. sickle cell anemia, etc. may also be performed. See, e.g. Current Protocols in Immunology (Richard Coico, ed. John Wiley & Sons, Inc. 2012) and Immunology Methods Manual (I. Lefkovits ed., Academic Press 1997), the disclosures of which are incorporated herein by reference.

So, for example, a method is provided for determining the effect of an agent on erythroid cells infectable or infected by pathogen, comprising administering the agent to a human EPO mouse, e.g. a Rag2$^{-/-}$IL2rg$^{-/-}$EPO$^{m/h}$ mouse, that has been engrafted with human reticulocytes and/or erythrocytes; measuring a parameter of the viability of the engrafted cells over time in the presence of the agent; and comparing that measurement to the measurement from an engrafted human EPO mouse not exposed to the agent. The agent is determined to be anti-pathogenic if it reduces the infection of and/or the death of human erythrocytes in the peripheral blood of the mouse by at least 20%, 30%, 40% or more, in some instances 50%, 60%, 70% or more, e.g. 80%, 90% or 100%, i.e., to undetectable amounts, following a single administration or two or more administrations of the agent over a selected period of time. In a specific embodiment, the administration of the drug or combination of drugs is at least three days, at least one week, at least 10 days after engraftment with human hematopoietic cells, for example, two week, three weeks, or four weeks after engraftment with human hematopoietic cells, e.g. 6 weeks, 8 weeks, 10 weeks or more after engraftment with human hematopoietic cells.

Other examples of uses for the subject mice are provided elsewhere herein. Additional applications of the genetically modified and engrafted mice described in this disclosure will be apparent to those skilled in the art upon reading this disclosure.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Example 1

Generation of Human EPO Knock-In Mice

Coding sequence at the mouse erythropoietin gene locus (Mouse NCBI Gene ID:13856; MGI:95407; RefSeq transcript cDNA at NM_007942.2 (SEQ ID NO:1) and encoded protein at NP_031968 (SEQ ID NO:2)) was replaced with coding sequence from the human erythropoietin gene locus (Human NCBI Gene ID:2056; HGNC: 3415; RefSeq cDNA transcript at NM_000799.2 (SEQ ID NO:3) and encoded protein at NP_000790 (SEQ ID NO:4)).

TABLE 1

```
SEQ        1   gatgaagact tgcagcgtgg acactggccc agccccgggt cgctaaggag ctccggcagc
ID        61   taggcgcgga gatgggggtg cccgaacgtc ccaccctgct gcttttactc tccttgctac
NO: 1    121   tgattcctct gggcctccca gtcctctgtg ctccccacg cctcatctgc gacagtcgag
         181   ttctggagag gtacatctta gaggccaagg aggcagaaaa tgtcacgatg ggttgtgcag
         241   aaggtcccag actgagtgaa aatattacag tcccagatac caaagtcaac ttctatgctt
         301   ggaaaagaat ggaggtggaa gaacaggcca tagaagtttg gcaaggcctg tccctgctct
         361   cagaagccat cctgcaggcc caggccctgc tagccaattc ctcccagcca ccagagaccc
         421   ttcagcttca tatagacaaa gccatcagtg gtctacgtag cctcacttca ctgcttcggg
         481   tactgggagc tcagaaggaa ttgatgtcgc ctccagatac caccccacct gctccactcc
         541   gaacactcac agtggatact ttctgcaagc tcttccgggt ctacgccaac ttcctccggg
         601   ggaaactgaa gctgtacacg ggagaggtct gcaggagagg ggacaggtga catgctgctg
         661   ccaccgtggt ggaccgacga acttgctccc cgtcactgtg tcatgccaac cctcc
              (SEQ ID NO: 1)

SEQ        MGVPERPTLLLLLLSLLLIPLGLPVLCAPPRLICDSRVLERYILEAKEAENVTMGCAEGPRLSENITVP
ID         DTKVNFYAWKRMEVEEQAIEVWQGLSLLSEAILQAQALLANSSQPPETLQLHIDKAISGLRSLTSL
NO: 2      LRVLGAQKELMSPPDTTPPAPLRTLTVDTFCKLFRVYANFLRGKLKLYTGEVCRRGDR (SEQ ID
              NO: 2)

SEQ        1   cccggagccg gaccggggcc accgcgcccg ctctgctccg acaccgcgcc ccctggacag
```

TABLE 1-continued

```
ID          61  ccgccctctc ctccaggccc gtggggctgg ccctgcaccg ccgagcttcc cgggatgagg
NO: 3      121  gcccccggtg tggtcacccg gcgcgcccca ggtcgctgag ggaccccggc caggcgcgga
           181  gatgggggtg cacgaatgtc ctgcctggct gtggcttctc ctgtccctgc tgtcgctccc
           241  tctgggcctc ccagtcctgg gcgccccacc acgcctcatc tgtgacagcc gagtcctgga
           301  gaggtacctc ttggaggcca aggaggccga gaatatcacg acgggctgtg ctgaacactg
           361  cagcttgaat gagaatatca ctgtcccaga caccaaagtt aatttctatg cctggaagag
           421  gatggaggtc gggcagcagg ccgtagaagt ctggcagggc ctggccctgc tgtcggaagc
           481  tgtcctgcgg ggccaggccc tgttggtcaa ctcttcccag ccgtgggagc ccctgcagct
           541  gcatgtggat aaagccgtca gtggccttcg cagcctcacc actctgcttc gggctctggg
           601  agcccagaag gaagccatct cccctccaga tgcggcctca gctgctccac tccgaacaat
           661  cactgctgac actttccgca aactcttccg agtctactcc aatttcctcc ggggaaagct
           721  gaagctgtac acaggggagg cctgcaggac aggggacaga tgaccaggtg tgtccacctg
           781  ggcatatcca ccacctccct caccaacatt gcttgtgcca caccctcccc cgccactcct
           841  gaaccccgtc gaggggctct cagctcagcg ccagcctgtc ccatggacac tccagtgcca
           901  gcaatgacat ctcaggggcc agaggaactg tccagagagc aactctgaga tctaaggatg
           961  tcacagggcc aacttgaggg cccagagcag gaagcattca gagagcagct ttaaactcag
          1021  ggacagagcc atgctgggaa gacgcctgag ctcactcggc accctgcaaa atttgatgcc
          1081  aggacacgct ttggaggcga tttacctgtt ttcgcaccta ccatcaggga caggatgacc
          1141  tggagaactt aggtggcaag ctgtgacttc tccaggtctc acgggcatgg gcactccctt
          1201  ggtggcaaga gcccccttga caccggggtg gtgggaacca tgaagacagg atgggggctg
          1261  gcctctggct ctcatggggt ccaagttttg tgtattcttc aacctcattg acaagaactg
          1321  aaaccaccaa aaaaaaaaaa (SEQ ID NO: 3)
```

```
SEQ    MGVHECPAWLWLLLSLLSLPLGLPVLGAPPRLICDSRVLERYLLEAKEAENITTGCAEHC
ID     SLNENITVPDTKVNFYAWKRMEVGQQA VEVWQGLALLSEAVLRGQALLVNSSQPWEP
NO: 4  LQLHVDKAVSGLRSLTTLLRALGAQKEAISPPDAASAAPLRTITADTFRKLFRVYSNFLR
       GKLKLYTGEACRTGDR (SEQ ID NO: 4)
```

Specifically, the mouse genomic region at GRCm38: ch5: 137482017:137485745 (minus strand) was deleted and human genomic sequence from GRCh37: ch7: 100318604: 100321567 (plus strand) was inserted in its place. This resulted in the replacement of coding exons 1 to 5—the entire coding region—of the mouse Epo gene with exons 1 to 5 plus the 3' human untranslated region of the human EPO gene. In total, 3729 nt of mouse sequence was replaced with 2964 nt human sequence.

Figure 3:
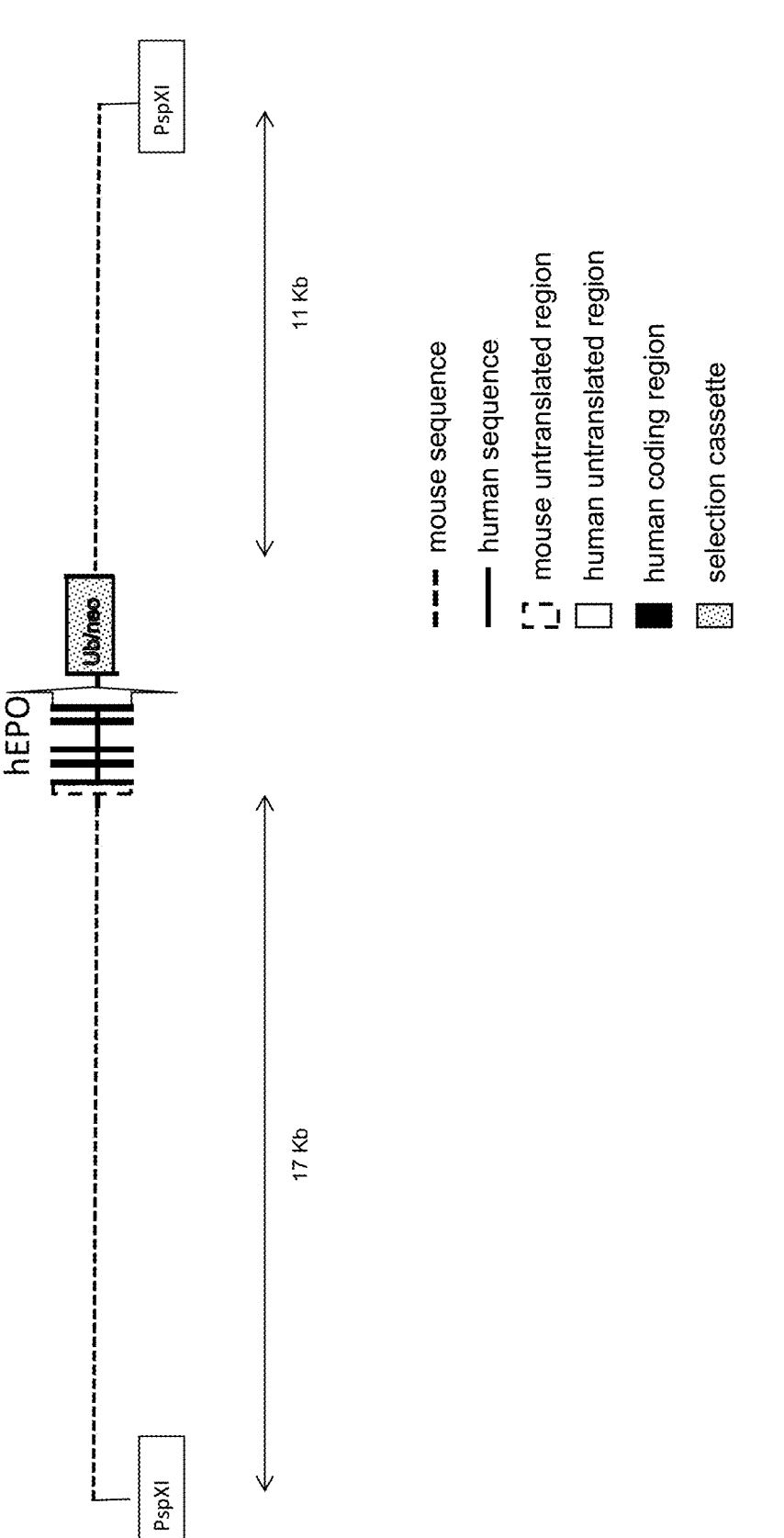
FIG. 3 provides a schematic of the human EPO knock-in allele.

Briefly, a targeting construct for replacing the mouse EPO gene with the human EPO gene in a single targeting step was constructed using VELOCIGENE® genetic engineering technology (see, Valenzuela et al. (2003), supra, and U.S. Pat. No. 6,586,251). Mouse and human EPO DNA were obtained from bacterial artificial chromosomes bMQ-386K4 and RP11-797M3, respectively. A PspXI-linearized targeting construct generated by gap repair cloning containing mouse EPO upstream and downstream homology arms flanking a 2964 nt human EPO sequence extending from the ATG in exon 1 through the stop codon in exon 5 (i.e. including 3' downstream sequence) plus a foxed neo selection cassette was electroporated into Rag2−/−IL2rg^{Y/−} ES cells (FIG. 2 and FIG. 3). The junction between the mouse EPO 5' untranslated region (UTR) and exon 1 of human EPO is provided as SEQ ID NO: 5, wherein the final mouse nucleotide prior to the first nucleotide of the human gene is the "G" (shown in brackets) in the portion of SEQ ID NO:5 which is not bolded in Table 2 below, and the first nucleotide of the human sequence is the "A" (shown in brackets) in the bolded portion of SEQ ID NO:5 in Table 2 below.

The junction between the human 3' UTR and the 5' end of the selection cassette is provided as SEQ ID NO:6, wherein the final nucleotide of the human sequence is the "C" (shown in single brackets) in the bolded portion of SEQ ID NO:6 in Table 3 below and the first nucleotide of the selection cassette sequence is the "C" (shown in double brackets) in the non-bolded portion of SEQ ID NO:6 in Table 3 below; the downstream junction region also contained a loxP site at the 3' end for removal of a foxed ubiquitin promoter-driven neo cassette.

TABLE 2

```
SEQ ID   TCTTCCAGGCTAGTGGGGTGATCTGGCCCTACAGAACTTCCAAGGATGAAGACTTGCAGC
NO: 5    GTGGACACTGGCCCAGCCCCGGGTCGCTAAGGAGCTCCGGCAGCTAGGCGCGGA[G][A]T
         GGGGGTGCACGGTGAGTACTCGCGGGCTGGGCGCTCCCGCCCGCCCGGGTCCCTGT
         TTGAGCGGGGATTTAGCGCCCCGGCTATTGGCCAGGAGGTGGCTGGGTTCAAG
         (SEQ ID NO: 5)
         (coding sequence of human exon 1 is italicized, bold is human,
         not bold is mouse)
```

TABLE 3

```
SEQ ID    . . . ACTCCGAACAATCACTGCTGACACTTTCCGCAAACTCTTCCGAGTCTACTCCAA
NO: 6     TTTCCTCCGGGGAAAGCTGAAGCTGTACACAGGGGAGGCCTGCAGGACAGGGGACAGATG
          ACCAGGTGTGTCCACCTGGGCATATCCACCACCTCCCTCACCAACATTGCTTGTGCC
          ACACCCTCCCCGCCACTCCTGAACCCCGTCGAGGGGCTCTCAGCTCAGCGCCAGC
          CTGTCCCATGGACACTCCAGTGCCAGCAATGACATCTCAGGGGCCAGAGGAACTGT
          CCAGAGAGCAACTCTGAGATCTAAGGATGTCACAGGGCCAACTTGAGGGCCCAGAG
          CAGGAAGCATTCAGAGAGCAGCTTTAAACTCAGGGACAGAGCCATGCTGGGAAGAC
          GCCTGAGCTCACTCGGCACCCTGCAAAATTTGATGCCAGGACACGCTTTGGAGGCG
          ATTTACCTGTTTTCGCACCTACCATCAGGGACAGGATGACCTGGAGAACTTAGGTG
          GCAAGCTGTGACTTCTCCAGGTCTCACGGGCATGGGCACTCCCTTGGTGGCAAGAG
          CCCCCTTGACACCGGGGTGGTGGGAACCATGAAGACAGGATGGGGGCTGGCCTCT
          GGCTCTCATGGGGTCCAAGTTTTGTGTATTCTTCAACCTCATTGACAAGAACTGAAA
          CCACCAATATGACTCTTGGCTTTTCTGTTTTCTGGGAACCTCCAAATCCCCTGGCTC
          TGTCCCACTCCTGGCAGCAGTGCAGCAGGTCCAGGTCCGGGAAACGAGGGGTGGA
          GGGGGCTGGGCCCTACGTGCTGTCTCACACAGCCTGTCTGACCTCTCGACCCTACC
          GGGCCTGAGGCCACAAGCTCTGCCTACGCTGGTCAATAAGGTGTCTCCATTCAAGG
          CCTCACCGCAGTAAGGCAGCTGCCAA[C][[C]]TCGAGATAACTTCGTATAATGTATGCT
          ATACGAAGTTATATGCATGGCCTCCGCGCCGGGTTTTGGCGCCTCCCGCGGGCGCCCCCC
          TCCTCACGGCGAGCGCTGCCACGTCAGACGAAGGGCGCAG . . .
          (bold is human, italicized is coding sequence of human exon 5;
          not bold is 5' end of selection cassette)
```

The junction between the 3' end of the selection cassette and the mouse genome is provided as SEQ ID NO:7, where the "C" shown in single brackets is the final nucleotide of the neo cassette and the first nucleotide of the mouse genome following the cassette is the "G" shown in double brackets, as shown in Table 4 below.

TABLE 4

```
SEQ ID    GCCTCTGTTCCACATACACTTCATTCTCAGTATTGTTTTGCCAAGTTCTAATTCCATCAGACCTCG
NO: 7     ACCTGCAGCCCCTAGATAACTTCGTATAATGTATGCTATACGAAGTTATGCTAG[C][[G]]CCAAC
          CCGCTAGGACAAGTGCTGAGTGAGCTGGGGCCACCGTTTGAGGAAACAGGAGCCAGTAC
          AGAGGGGTTCCCCTTTAGGGGTTGGTGGCAATGGGCGACCCTGGTTAATGGATCATT . . .
          (3' end of selection cassette shown in italics, mouse sequence
          is shown not italicized.)
```

Correctly targeted hEPO ES cell clones were identified by a loss-of-native-allele (LONA) assay (Valenzuela et al. (2003), supra) in which the number of copies of the native, unmodified EPO gene were determined by two TaqMan™ quantitative polymerase chain reactions (qPCRs) specific for sequences in the mouse EPO gene that were targeted for deletion. The qPCR assays comprised the following primer-probe sets (written 5' to 3'): upstream forward primer, CATCTGCGACAGTCGAGTTC (SEQ ID NO:8); upstream reverse primer, CCAGGGAGCTTACCGTGAC (SEQ ID NO:9); upstream probe, FAM-AGGTACATCT-TAGAGGCCAAGGAGGCA-BHQ (SEQ ID NO:10); downstream forward primer, ACAGCCGAGTCCTG-GAGAG (SEQ ID NO:11); downstream reverse primer, AAGCCCTGAGCGTGAGTTC (SEQ ID NO:12); downstream probe, FAM-AGGCCAAGGAGGCCGAGAATAT-CACG-BHQ (SEQ ID NO:13); in which FAM refers to the 5-carboxyfluorescein fluorescent probe and BHQ refers to the fluorescence quencher of the black hole quencher type (Biosearch Technologies). DNA purified from ES cell clones that have taken up the targeting vector and incorporated in their genomes was combined with TaqMan™ Gene Expression Master Mix (Life Technologies) according to the manufacturer's suggestions in a 384-well PCR plate (Micro-Amp™ Optical 384-Well Reaction Plate, Life Technologies) and cycled in an Applied Biosystems Prism 7900HT, which collects fluorescence data during the course of the PCRs and determines a threshold cycle (Ct), the fractional PCR cycle at which the accumulated fluorescence reaches a pre-set threshold. The upstream and downstream EPO-specific qPCRs and two qPCRs for non-targeted reference genes were run for each DNA sample. The differences in the Ct values (ΔCt) between each EPO-specific qPCR and each reference gene qPCR were calculated, and then the difference between each ΔCt and the median ΔCt for all samples assayed was calculated to obtain ΔΔCt values for each sample. The copy number of the EPO gene in each sample was calculated from the following formula: copy number$=2 \cdot 2^{-\Delta\Delta Ct}$. A correctly targeted clone, having lost one of its native copies, will have an EPO gene copy number equal to one. Confirmation that the human EPO gene sequence replaced the deleted mouse EPO gene sequence in the humanized allele was confirmed by a TaqMan™ qPCR assay that comprises the following primer-probe sets (written 5' to 3'): the human forward primer, GAGCCCTGCACTGGACAAC (SEQ ID NO:14); the human reverse primer, TCCCATGAACGCTGAGAGTC (SEQ ID NO:15); and the human probe, AGGGT-CAAGGAGCCATAGACAGAATGGC (SEQ ID NO:16).

Correctly targeted ES cells were electroporated with a transient Cre-expressing vector to remove the drug selection cassette. To generate a mouse comprising human EPO and deficient for Rag2 and Il2rg, correctly targeted ES cells were identified as described above and introduced into preimplantation embryo using techniques known in the art. Human EPO knock-in (KI) mice were then backcrossed to generate mice deficient for Rag2 and Il2rg and expressing human EPO.

Example 2

Generation of Human SIRPα-Mice

In connection with some of the examples described herein, a genetically modified mouse including a nucleic acid sequence encoding human SIRPα randomly integrated into the genome of the genetically modified mouse was prepared as described in U.S. Patent Application Publication No. 2013-0340105, the disclosure of which is incorporated by reference herein.

In connection with some of the examples described herein, a human SIRPα knock-in mouse was prepared as described below. Human SIRPα is known to exist in at least 10 allelic forms. In this particular example, human SIRPα variant 1 is employed for humanizing an endogenous SIRPα gene of a mouse.

A targeting vector for humanization of an extracellular region of a SIRP (e.g., SIRPα) gene was constructed using VELOCIGENE® technology (see, e.g., U.S. Pat. No. 6,586,251 and Valenzuela et al. (2003), supra).

Figure 4:
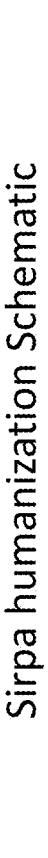
FIG. 4 provides schematics of the wild type mouse Sirpa locus before (above) and after (below) knock in of a nucleic acid sequence encoding humanized Sirpa.

Briefly, mouse bacterial artificial chromosome (BAC) clone bMQ-261H14 was modified to delete the sequence containing exons 2 to 4 of an endogenous SIRPα gene and insert exons 2 to 4 of a human SIRPα gene using human BAC clone CTD-3035H21. The genomic DNA corresponding to exons 2 to 4 of an endogenous SIRPα gene (~8555 bp) was replaced in BAC clone bMQ-261H14 with a ~8581 bp DNA fragment containing exons 2 to 4 of a human SIRPα gene from BAC clone CTD-3035H21. Sequence analysis of the human SIRPα allele contained in BAC clone CTD-3035H21 revealed the allele to correspond to human variant 1. A neomycin cassette flanked by loxP sites was added to the end of the ~8581 bp human DNA fragment containing exons 2 to 4 of the human SIRPα gene (FIG. 4).

Upstream and downstream homology arms were obtained from mouse BAC DNA at positions 5' and 3' of exons 2 and 4, respectively, and added to the 8581 bp human fragment-neomycin cassette to create the final targeting vector for humanization of an endogenous SIRPα gene, which contained from 5' to 3' a 5' homology arm containing 19 kb of mouse DNA 5' of exon 2 of the endogenous SIRPα gene, a ~8581 bp DNA fragment containing exons 2 to 4 of a human SIRPα gene, a neomycin cassette flanked by loxP sites, and a 3' homology arm containing 21 kb of mouse DNA 3' of exon 4 of an endogenous SIRPα gene. Targeted insertion of the targeting vector positioned the neomycin cassette in the fifth intron of a mouse SIRPα gene between exons 4 and 5. The targeting vector was linearized by digesting with SwaI and then used in homologous recombination in bacterial cells to achieve a targeted replacement of exons 2 to 4 in a mouse SIRPα gene with exons 2 to 4 of a human SIRPα gene (FIG. 4).

The targeted BAC DNA (described above) was used to electroporate mouse ES cells to created modified ES cells comprising a replacement of exons 2 to 4 in an endogenous mouse SIRPα gene with a genomic fragment comprising exons 2 to 4 of a human SIRPα gene. Positive ES cells containing a genomic fragment comprising exons 2 to 4 of a human SIRPα gene were identified by quantitative PCR using TAQMAN™ probes (Lie and Petropoulos, 1998. Curr. Opin. Biotechnology 9:43-48). The nucleotide sequence across the upstream insertion point included the following, which indicates endogenous mouse sequence upstream of the insertion point (contained within the parentheses below) linked contiguously to a human SIRPα genomic sequence present at the insertion point: (AGCTCTCCTACCACTAGACTGCTGA-GACCCGCTGCTCTGCTCAGGACTCGATTTCCA GTA-CACAATCTCCCTCTTTGAAAAGTACCACA-CATCCTGGGGT)GCTCTTGCATTTGT GTGACACTTTGCTAGCCAGGCTCAGTCCTGGG-TTCCAGGTGGGGACTCAAACACACT GGCACGAGTCTACATTGGATATTCTTGGT (SEQ ID NO: 17). The nucleotide sequence across the downstream insertion point at the 5' end of the neomycin cassette included the following, which indicates human SIRPα genomic sequence contiguous with cassette sequence downstream of the insertion point (contained within the parentheses below with loxP sequence italicized): GCTCCCCATTCCTCACTGGCCCAGCCCCTCTTCCC-TACTCTTTCTAGCCCCTGCCTCAT CTCCCTGGCTGCCATTGGGAGCCTGCCCCACTG-GAAGCCAG(TCGAG*ATAACTTCGTAT AATGTATGC-TATACGAAGTTAT*ATG-CATGGCCTCCGCGCCGGGTTTTGGCGCCTCCCGC GGGCGCCCCCCTCCTCACGGCGA) (SEQ ID NO: 18). The nucleotide sequence across the downstream insertion point at the 3' end of the neomycin cassette included the following, which indicates cassette sequence contiguous with mouse genomic sequence 3' of exon 4 of an endogenous SIRPα gene (contained within the parentheses below): CATTCTCAGTATTGTTTTGCCAAGTTCTAATTC-CATCAGACCTCGACCTGCAGCCCCT AGA-TAACTTCGTATAATGTATGCTATACGAAGT-TATGCTAGC(TGTCTCATAGAGGCT GGCGATCTGGCTCAGGGACAGCCAGTACTG-CAAAGAGTATCCTTGTTCATACCTTCT CCTAGTGGCCATCTCCCTGGGACAGTCA) (SEQ ID NO: 19). Positive ES cell clones were then used to implant female mice using the VELOCIMOUSE® method (see, e.g., U.S. Pat. No. 7,294,754 and Poueymirou et al. 2007, F0 generation mice that are essentially fully derived from the donor gene-targeted ES cells allowing immediate phenotypic analyses Nature Biotech. 25(1):91-99, supra) to generate a litter of pups containing an insertion of exons 2 to 4 of a human SIRPα gene into an endogenous SIRPα gene of a mouse.

Targeted ES cells described above were used as donor ES cells and introduced into an 8-cell stage mouse embryo by the VELOCIMOUSE® method (supra). Mice bearing the humanization of exons 2 to 4 of an endogenous SIRPα gene were identified by genotyping using a modification of allele assay (Valenzuela et al. (2003), supra) that detected the presence of the human SIRPα gene sequences.

Mice bearing the humanized SIRPα gene construct (i.e., containing human SIRPα exons 2 to 4 in a mouse SIRPa gene) can be bred to a Cre deletor mouse strain (see, e.g., International Patent Application Publication No. WO 2009/114400) in order to remove any loxed neomycin cassette introduced by the targeting vector that is not removed, e.g., at the ES cell stage or in the embryo. Optionally, the neomycin cassette is retained in the mice.

Example 3

Generation of Compound Knock-In Mice

Human EPO knock-in mice were crossed to mice expressing other human genes of interest either as random integrants into the mouse genome or as knock-ins, i.e. from the corresponding mouse locus. For example, Rag2$^{-/-}$, IL-2rg$^{Y/-}$, hEPO KI mice were crossed with mice expressing human TPO from the mouse TPO locus (Rongvaux et al., 2011, Proc Natl Acad Sci USA, 108(6): 2378-2383), human IL-3 and human GM-CSF from the mouse IL-3/GM-CSF locus (Willinger et al, 2011, Proc Natl Acad Sci USA, 108(6): 2390-2395), human M-CSF from the mouse M-CSF locus (Rathinam et al, 2011, Blood, 118(11): 3119-3128), and/or human SIRPa expressed as a random integrant (Strowig et al., 2011, Proc Natl Acad Sci USA, 108(32): 13218-13223) or from the mouse locus as described above to generate mice expressing a combination of these human proteins (Rag2$^{-/-}$Il2rg$^{null}$hSIRPd$^{h/h}$Tpo$^{h/h}$Mcsf$^{h/h}$Il3/Gmcsf$^{h/h}$EPO$^{h/h}$). Genetically modified mice expressing one or more of human TPO, human IL-3, human GM-CSF, human M-CSF, and human SIRPa are described in greater detail in U.S. Pat. Nos. 8,541,646 and 8,847,004; U.S. Patent Application Publication No. 2014/0134662; and PCT International Publication No. WO/2014/039782; the disclosure of each of which is incorporated by reference herein.

Example 4

Development of a Humanized Mouse Model for the Blood Stages of *P. Falciparum* and *P. Vivax*

It is demonstrated here that genetic humanization of the murine host by providing growth factors with limited cross-reactivity from mouse to man can successfully boost human cell engraftment in general and erythropoiesis in particular in human hematopoietic stem cell (HSC)-engrafted mice.

MITERG mice expressing human EPO from their genome (to enhance terminal erythropoiesis) as well as human TPO, MCSF, and IL-3 (to enhance HSC maintenance and early erythropoiesis) feature higher levels of human erythropoiesis in the bone marrow of human HSC-engrafted mice than mice not expressing hEPO (FIG. 5A, compare "hSIRPa-, hEPO+" (i.e. "MITERG mice"), to "hSIRPa-, hEPO-" (i.e. "MITRG mice")), in fact equivalent to mouse erythropoiesis in the same animal. However, these mice lack significant levels of circulating human erythroid cells (data not shown).

It was hypothesized that low levels of circulating human erythroid cells in the periphery results from destruction (erythrophagocytosis) of the peripheral human RBCs by mouse macrophages. The role of SIRPa in this process was evaluated by generating mice in which hSIRPa was expressed from a locus in the mouse genome other than the mSIRPa locus, i.e., as a randomly integrated transgene, i.e. as an hSIRPa-tg (Rag2$^{-/-}$Il2rg$^{null}$Tpo$^{h/h}$Mcsf$^{h/h}$Il3$^{h/}$$_h$Gmcsf$^{h/h}$Epo$^{h/h}$SIRPα-tg+, i.e. "MISTER-G mice") and mice in which hSIRPa was expressed as a knock-in (KI) from the mSIRPa locus, i.e. as an hSIRPa KI (Rag2$^{-/-}$Il2rg$^{null}$Tpo$^{h/h}$Mcsf$^{h/h}$Il3$^{h/h}$Gmcsf$^{h/h}$Epo$^{h/h}$SIRPα$^{h/h}$, i.e. "SupER-G mice").

Expression of human SIRPa, e.g. as a randomly-integrated transgene in MISTER-G mice, promoted a further increase in the number of human erythroid cells in the bone marrow of human HSC-engrafted mice expressing human EPO (FIG. 5, Panel A, compare "hSIRPa+, hEPO+" to "hSIRPa-, hEPO+"). Introduction of human SIRPa significantly improved the survival of most hematopoietic cells in the periphery, with the frequency of human CD45$^+$ cells including lymphoid and myeloid cells in peripheral blood increasing by at least 10 fold over that observed in mice that did not express hSIRPa. However, hSIRPa KI has little effect on the engraftment levels of human RBCs in peripheral blood (FIG. 5, Panel B).

Since human SIRPα knock-in is not sufficient to increase human erythroid cells in the peripheral blood, clodronate liposomes were used for the depletion of macrophages, specifically red pulp macrophages in the spleen and Kupffer cells in liver. A dramatic increase of circulating human cells of the erythroid lineage was observed in SuPER-G mice to 1% of the total circulating erythroid cells after the depletion of tissue resident macrophages by clodronate liposome (FIG. 6, Panel A). In addition, most human erythroid cells in the periphery after clodronate treatment were reticulocytes (CD71$^+$) (FIG. 6, Panel B) This is an exciting observation because it indicates that these mice would be good candidates to support *P. vivax* infection, which preferentially infects reticulocytes.

Infection of erythroid cells is an essential part of the life cycle of *Plasmodium* sp. However, the required frequency of human RBC necessary for successful in vivo infection with different *Plasmodium* species has not been established. The only in vivo models for *P. falciparum* presently available are based on the transfer of human RBCs into immunodeficient strains such as NOD/scid or NSG. In these mice, infection with merozoites can be achieved by i.v. injection of infected erythrocytes only after daily injection of large numbers of human erythrocytes. At the time of infection, human RBCs comprise roughly half of total erythrocyte number in these animals.

As demonstrated above, SupER-G mice engrafted with human hematopoietic stem cells (HSC) developed human erythroid cells in the bone marrow (FIG. 5B), and ii) clodronate treatment increased the frequency of human erythroid cells in the periphery of engrafted SupER-G mice (FIG. 6). To determine if engrafted, clodronate-treated SupER-G mice comprised a sufficient number of human erythroid cells in the periphery to sustain a successful *Plasmodium* infection in vivo, peripheral blood was collected from SupER-G mice engrafted with fetal liver or adult HSCs, and the blood cultured in vitro with *P. falciparum* strain 3D7-infected blood. To facilitate multiple rounds of parasite replication, fresh human red blood cells were added into the infection culture 48 hours later, the expectation being that amplification by reinfection of the subsequently added human RBCs will only occur if the human RBCs harvested from the HSC-engrafted SupER-G mice had produced the full infectious cycle of *P. falciparum*. Twelve days after infection, advanced stage of parasite infection and amplification of merozoites from schizont was observed in all blood samples from engrafted SuPER-G mice ("engrafted mouse RBCs, adult 1", "engrafted mouse RBCs, adult 2", and "engrafted mouse RBCs, fetal liver") but not from control mice that are either unengrafted or acutely engrafted with 0.1% hRBCs by injection ("spiked control") (FIG. 7A and data not shown). Exponential increase of parasitemia was observed by Giemsa staining and quantitative PCR (FIG. 7B). This indicates that engrafted, clodronate-treated SupER-G produce a sufficient number of human red blood cells to sustain an infection with *P. falciparum*. From this, it is expected that in vivo infection of clodronate-dosed engrafted mice with *P. falciparum* and *P. vivax* merozoites will be successful.

Example 5

The TIES Mice (Rag2$^{-/-}$Il2rg$^{null}$Tpo$^{h/h}$Il3/Gmcsf$^{h/}$$_h$Epo$^{h/m}$SIRPα$^{h/h}$)

Due to low fertility, developmental incompetency and high mortality, mice with Epo$^{h/h}$ are not ideal for infection study. Instead, mice heterozygous for the hEPO gene (i.e. Epo$^{h/m}$, e.g., the TIES mice) are fully capable of producing erythropoietin (EPO) and support all stages of erythropoiesis. Further improvement in viability from 8-10 weeks to 4 months was achieved by retaining the mouse M-CSF gene at the mouse locus rather than replacing it with human M-CSF, because high level of human myeloid cell engraftment supported by human Macrophage colony stimulating factor (M-CSF) knock-in cause destruction of mouse red blood cells which leads to anemia and death of engrafted mice.

Like SupER-G mice, TIES mice support human erythropoiesis and maintain a frequency of 1% human erythroid cells in the peripheral blood if dosed with clodronate. In addition, most human erythroid cells in the periphery after clodronate treatment were reticulocytes (CD71+). This suggests that these mice will be good candidates to support *P. vivax* infection.

Figure 8:
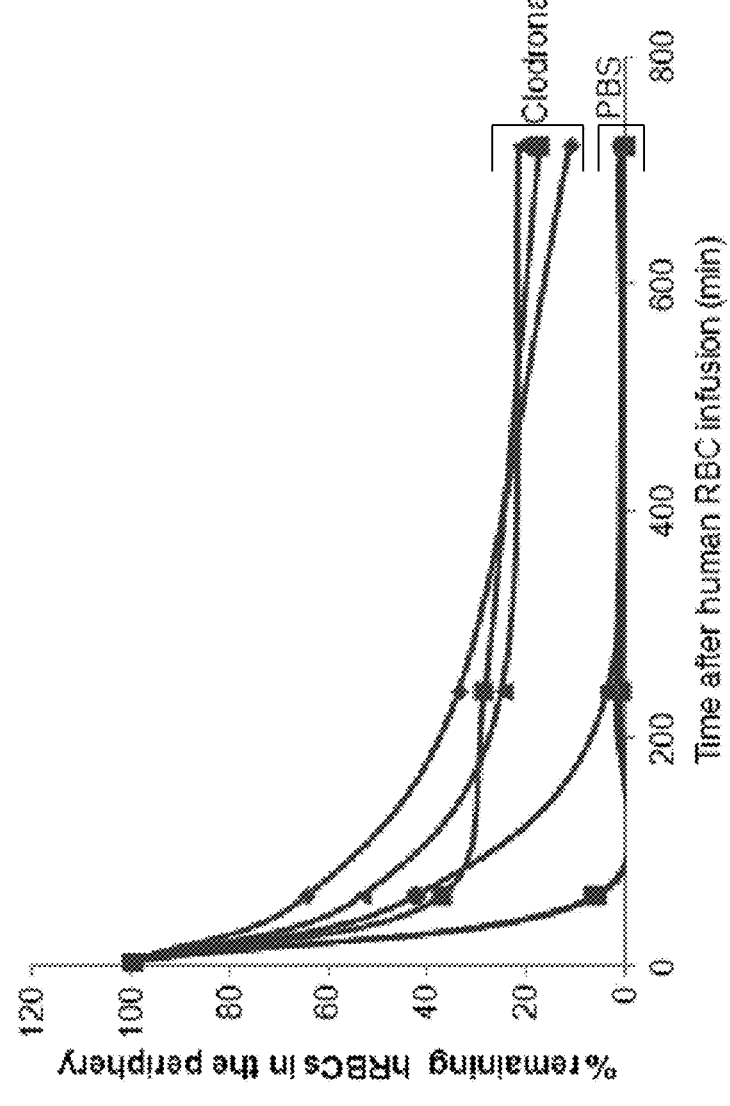
FIG. 8 shows the destruction of human RBCs in the mouse peripheral blood in the absence of clodronate. Unengrafted mice were treated with clodronate or PBS. For clodronate treatment, mice received daily retro-orbital injection of 50 μl clodronate for three consecutive days. For PBS treatment, 500 μl PBS only was delivered one hour before human RBC transfusion. Human RBCs were transfused into pre-treated mice and peripheral blood was collected at indicated time points. Clodronate and PBS curves are shown.

It was demonstrated that engrafted TIES mice can maintain a frequency of 1% human erythroid cells in the peripheral blood if dosed with clodronate. In addition, the ability of TIES mice to support a transfusion of human RBCs was determined. As shown in FIG. 8, clodronate treatment stabilized the transfused population at more than 20% of the total population of cells in the periphery. These levels, realized at about 4 hours after transfusion, were sustained at least 12 hours after transfusion. It is expected that these RBC frequencies will be sufficient to support an in vivo infection of *Plasmodium* of different species.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A genetically modified mouse, wherein the genetically modified mouse is an EPO$^{h/h}$ M-CSF$^{h/h}$ GM-CSF$^{h/h}$ IL-3$^{h/h}$ TPO$^{h/h}$ SIRPα$^{h/h}$ mouse comprising:

an erythropoietin (EPO) knock-in allele comprising a nucleic acid sequence that encodes a human erythropoietin (hEPO) protein operably linked to an endogenous mouse EPO gene promoter at the mouse EPO gene locus in the genome of the genetically modified mouse, wherein the EPO knock-in allele comprises a replacement of at least some of an endogenous mouse EPO coding sequence, wherein the mouse is homozygous for the EPO knock-in allele (EPOh/h), wherein the mouse expresses the hEPO protein, and wherein the hEPO protein possesses wild-type human EPO signaling function;

a macrophage colony stimulating factor (M-CSF) knock-in allele comprising a nucleic acid sequence that encodes a human macrophage colony stimulating factor (hGM-CSF) protein operably linked to an endogenous mouse M-CSF gene promoter at the mouse M-CSF gene locus in the genome of the genetically modified mouse, wherein the M-CSF knock-in allele comprises a replacement of at least some of an endogenous mouse M-CSF coding sequence, wherein the mouse is homozygous for the M-CSF knock-in allele (M-CSF$^{h/h}$), wherein the mouse expresses the hM-CSF protein, and wherein the hM-CSF protein possesses wild-type human M-CSF signaling function;

a granulocyte-macrophage colony stimulating factor 2 (GM-CSF) knock-in allele comprising a nucleic acid sequence that encodes a human granulocyte-macrophage colony stimulating factor 2 (hGM-CSF) protein operably linked to an endogenous mouse GM-CSF gene promoter at the mouse GM-CSF gene locus in the genome of the genetically modified mouse, wherein the GM-CSF knock-in allele comprises a replacement of at least some of an endogenous mouse GM-CSF coding sequence, wherein the mouse is homozygous for the GM-CSF knock-in allele (GM-CSF$^{h/h}$), wherein the mouse expresses the hGM-CSF protein, and wherein the hGM-CSF protein possesses wild-type human GM-CSF signaling function;

an interleukin 3 (IL-3) knock-in allele comprising a nucleic acid sequence that encodes a human interleukin 3 (hIL3) protein operably linked to an endogenous mouse IL-3 gene promoter at the mouse IL-3 gene locus in the genome of the genetically modified mouse, wherein the IL-3 knock-in allele comprises a replacement of at least some of an endogenous mouse IL-3 coding sequence, wherein the mouse is homozygous for the IL-3 knock-in allele (IL-3 h/h), wherein the mouse expresses the hIL-3 protein, and wherein the hIL-3 protein possesses wild-type human IL-3 signaling function;

a thrombopoietin (TPO) knock-in allele comprising a nucleic acid sequence that encodes a human thrombopoietin (hTPO) protein operably linked to an endogenous mouse TPO gene promoter at the mouse TPO gene locus in the genome of the genetically modified mouse, wherein the TPO knock-in allele comprises a replacement of at least some of an endogenous mouse TPO coding sequence, wherein the mouse is homozygous for the TPO knock-in allele (TPOh/h), wherein the mouse expresses the hTPO protein, and wherein the hTPO protein possesses wild-type human TPO signaling function; and a signal-regulatory protein alpha (SIRPα) knock-in allele comprising a nucleic acid sequence that encodes a humanized signal-regulatory protein alpha (hSirpa) protein operably linked to an endogenous mouse SIRPα gene promoter at the mouse SIRPα gene locus in the genome of the genetically modified mouse, wherein the SIRPα knock-in allele comprises a replacement of a portion of an endogenous mouse SIRPα coding sequence, wherein the mouse is homozygous for the SIRPα knock-in allele (SIRPα$^{h/h}$), wherein the mouse expresses the hSIRPα protein, wherein the hSIRPα protein comprises an extracellular domain of a wild-type human SIRPα protein and a signaling domain of an endogenous mouse SIRPα protein, and wherein the hSIRPα protein possesses wild-type human SIRPα receptor function.

2. The genetically modified mouse of claim 1, wherein the nucleic acid sequence that encodes the hEPO protein comprises human EPO genomic coding and non-coding sequence.

3. The genetically modified mouse of claim 1, wherein the nucleic acid sequence that encodes the hEPO protein comprises human EPO cDNA sequence.

4. The genetically modified mouse of claim 1, wherein the genetically modified mouse is immunodeficient for an endogenous immune system.

5. The genetically modified mouse of claim 4, wherein the immunodeficiency is caused by a deficiency for one or both of Rag2 and Il2rg.

6. The genetically modified mouse of claim 5, wherein the genetically modified mouse is Rag2null and IL2rg$^{null}$.

7. The genetically modified mouse of claim 4, wherein the genetically modified mouse comprises an engraftment of human hematopoietic cells.

8. The genetically modified mouse of claim 7, wherein the human hematopoietic cells comprise one or more cells selected from the group consisting of: a human CD34-positive cell, a human hematopoietic stem cell, a human myeloid precursor cell, a human erythroid precursor cell, a human myeloid cell, a human dendritic cell, a human monocyte, a human granulocyte, a human erythrocyte, a human neutrophil, a human mast cell, a human thymocyte, and a human B lymphocyte.

9. The genetically modified mouse of claim 8, wherein the genetically modified mouse comprises clodronate.

10. The genetically modified mouse of claim 9, wherein the genetically modified mouse further comprises an infection with a pathogen that targets human cells of the erythroid lineage.

11. The genetically modified mouse of claim 10, wherein the pathogen is selected from a *Plasmodium* sp., a *Babesia* sp., and a *Theileri* sp.

12. A genetically modified mouse, wherein the genetically modified mouse is an EPO$^{h/m}$ IL-3$^{h/h}$ GM-CSF$^{h/h}$ TPO$^{h/h}$ SIRPα$^{h/h}$ mouse comprising:

an erythropoietin (EPO) knock-in allele comprising a nucleic acid sequence that encodes a human erythropoietin (hEPO) protein operably linked to an endogenous mouse EPO gene promoter at the mouse EPO gene locus in the genome of the genetically modified mouse, wherein the EPO knock-in allele comprises a replacement of at least some of an endogenous mouse EPO coding sequence, wherein the mouse is heterozygous for the EPO knock-in allele (EPO$^{h/m}$), wherein the mouse expresses the hEPO protein, and wherein the hEPO protein possesses wild-type human EPO signaling function;

an interleukin 3 (IL-3) knock-in allele comprising a nucleic acid sequence that encodes a human interleukin 3 (hIL3) protein operably linked to an endogenous mouse IL-3 gene promoter at the mouse IL-3 gene locus in the genome of the genetically modified mouse, wherein the IL-3 knock-in allele comprises a replacement of at least some of an endogenous mouse IL-3 coding sequence, wherein the mouse is homozygous for the IL-3 knock-in allele (IL-3 h/h), wherein the mouse expresses the hIL-3 protein, and wherein the hIL-3 protein possesses wild-type human IL-3 signaling function;

a granulocyte-macrophage colony stimulating factor 2 (GM-CSF) knock-in allele comprising a nucleic acid sequence that encodes a human granulocyte-macrophage colony stimulating factor 2 (hGM-CSF) protein operably linked to an endogenous mouse GM-CSF gene promoter at the mouse GM-CSF gene locus in the genome of the genetically modified mouse, wherein the GM-CSF knock-in allele comprises a replacement of at least some of an endogenous mouse GM-CSF coding sequence, wherein the mouse is homozygous for the GM-CSF knock-in allele (GM-CSF$^{h/h}$), wherein the mouse expresses the hGM-CSF protein, and wherein the hGM-CSF protein possesses wild-type human GM-CSF signaling function;

a thrombopoietin (TPO) knock-in allele comprising a nucleic acid sequence that encodes a human thrombopoietin (hTPO) protein operably linked to an endogenous mouse TPO gene promoter at the mouse TPO gene locus in the genome of the genetically modified mouse, wherein the TPO knock-in allele comprises a replacement of at least some of an endogenous mouse TPO coding sequence, wherein the mouse is homozygous for the TPO knock-in allele (TPO$^{h/h}$), wherein the mouse expresses the hTPO protein, and wherein the hTPO protein possesses wild-type human TPO signaling function; and a signal-regulatory protein alpha (SIRPα) knock-in allele comprising a nucleic acid sequence that encodes a humanized signal-regulatory protein alpha (hSirpa) protein operably linked to an endogenous mouse SIRPα gene promoter at the mouse SIRPα gene locus in the genome of the genetically modified mouse, wherein the SIRPα knock-in allele comprises a replacement of a portion of an endogenous mouse SIRPα coding sequence, wherein the mouse is homozygous for the SIRPα knock-in allele (SIRPα$^{h/h}$), wherein the mouse expresses the hSIRPα protein, wherein the hSIRPα protein comprises an extracellular domain of a wild-type human SIRPα protein and a signaling domain of an endogenous mouse SIRPα protein, and wherein the hSIRPα protein possesses wild-type human SIRPα receptor function, wherein the genetically modified mouse is homozygous for endogenous mouse macrophage colony stimulating factor (M-CSF$^{m/m}$) and does not express human M-CSF (hM-CSF).

13. The genetically modified mouse of claim 12, wherein the nucleic acid sequence that encodes the hEPO protein comprises human EPO genomic coding and non-coding sequence.

14. The genetically modified mouse of claim 12, wherein the nucleic acid sequence that encodes the hEPO protein comprises human EPO cDNA sequence.

15. The genetically modified mouse of claim 12, wherein the genetically modified mouse is immunodeficient for an endogenous immune system.

16. The genetically modified mouse of claim 15, wherein the genetically modified mouse is Rag2$^{null}$ and IL2rg$^{null}$.

17. The genetically modified mouse of claim 12, wherein the genetically modified mouse comprises an engraftment of human hematopoietic cells.

18. The genetically modified mouse of claim 17, wherein the human hematopoietic cells comprise one or more cells selected from the group consisting of: a human CD34-positive cell, a human hematopoietic stem cell, a human myeloid precursor cell, a human erythroid precursor cell, a human myeloid cell, a human dendritic cell, a human monocyte, a human granulocyte, a human erythrocyte, a human neutrophil, a human mast cell, a human thymocyte, and a human B lymphocyte.

19. The genetically modified mouse of claim 18, wherein the genetically modified mouse comprises clodronate.

20. The genetically modified mouse of claim 19, wherein the genetically modified mouse further comprises an infection with a pathogen that targets human cells of the erythroid lineage.

* * * * *

SEQUENCE LISTING

```
Sequence total quantity: 19
SEQ ID NO: 1              moltype = DNA   length = 715
FEATURE                   Location/Qualifiers
source                    1..715
                          mol_type = genomic DNA
                          organism = Mus musculus
SEQUENCE: 1
gatgaagact tgcagcgtgg acactggccc agccccgggt cgctaaggag ctccggcagc  60
taggcgcgga gatgggggtg cccgaacgtc ccaccctgct gcttttactc tccttgctac  120
tgattcctct gggcctccca gtcctctgtg ctcccccacg cctcatctgc gacagtcgag  180
ttctggagag gtacatctta gaggccaagg aggcagaaaa tgtcacgatg ggttgtgcag  240
aaggtcccag actgagtgaa aatattacag tcccagatac caaagtcaac ttctatgctt  300
ggaaaagaat ggaggtggaa gaacaggcca tagaagtttg gcaaggcctg tccctgctct  360
cagaagccat cctgcaggcc caggccctgc tagccaattc ctcccagcca ccagagaccc  420
ttcagcttca tatagacaaa gccatcagtg gtctacgtag cctcacttca ctgcttcggg  480
tactgggagc tcagaaggaa ttgatgtcgc ctccagatac caccccacct gctccactcc  540
gaacactcac agtggatact ttctgcaagc tcttccgggt ctacgccaac ttcctccggg  600
ggaaactgaa gctgtacacg ggagaggtct gcaggagagg ggacaggtga catgctgctg  660
ccaccgtggt ggaccgacga acttgctccc cgtcactgtg tcatgccaac cctcc        715

SEQ ID NO: 2              moltype = AA   length = 192
FEATURE                   Location/Qualifiers
source                    1..192
                          mol_type = protein
                          organism = Mus musculus
SEQUENCE: 2
MGVPERPTLL LLLSLLLIPL GLPVLCAPPR LICDSRVLER YILEAKEAEN VTMGCAEGPR  60
LSENITVPDT KVNFYAWKRM EVEEQAIEVW QGLSLLSEAI LQAQALLANS SQPPETLQLH  120
IDKAISGLRS LTSLLRVLGA QKELMSPPDT TPPAPLRTLT VDTFCKLFRV YANFLRGKLK  180
LYTGEVCRRG DR                                                       192

SEQ ID NO: 3              moltype = DNA   length = 1340
FEATURE                   Location/Qualifiers
source                    1..1340
                          mol_type = genomic DNA
                          organism = Homo sapiens
SEQUENCE: 3
cccggagccg gaccggggcc accgcgcccg ctctgctccg acaccgcgcc ccctggacag  60
ccgccctctc ctccaggccc gtggggctgg ccctgcaccg ccgagcttcc cgggatgagg  120
gcccccggtg tggtcacccg gcgcgcccca ggtcgctgag ggaccccggc caggcgcgga  180
gatgggggtg cacgaatgtc ctgcctggct gtggcttctc ctgtccctgc tgtcgctccc  240
tctgggcctc ccagtcctgg gcgccccacc acgcctcatc tgtgacagcc gagtcctgga  300
gaggtacctc ttggaggcca aggaggccga gaatatcacg acgggctgtg ctgaacactg  360
cagcttgaat gagaatatca ctgtcccaga caccaaagtt aatttctatg cctggaagag  420
gatggaggtc gggcagcagg ccgtagaagt ctggcagggc ctggccctgc tgtcggaagc  480
tgtcctgcgg ggccaggccc tgttggtcaa ctcttcccag ccgtgggagc ccctgcagct  540
gcatgtggat aaagccgtca gtggccttcg cagcctcacc actctgcttc gggctctggg  600
agcccagaag gaagccatct ccctccaga  tgcggcctca gctgctccac tccgaacaat  660
cactgctgac actttccgca aactcttccg agtctactcc aatttcctcc ggggaaagct  720
gaagctgtac acaggggagg cctgcaggac aggggacaga tgaccaggtg tgtccacctg  780
ggcatatcca ccacctccct caccaacatt gcttgtgcca caccctcccc cgccactcct  840
gaaccccgtc gaggggctct cagctcagcg ccagcctgtc ccatggacac tccagtgcca  900
```

-continued

```
gcaatgacat ctcaggggcc agaggaactg tccagagagc aactctgaga tctaaggatg   960
tcacagggcc aacttgaggg cccagagcag gaagcattca gagagcagct ttaaactcag  1020
ggacagagcc atgctgggaa gacgcctgag ctcactcggc accctgcaaa atttgatgcc  1080
aggacacgct ttggaggcga tttacctgtt ttcgcaccta ccatcaggga caggatgacc  1140
tggagaactt aggtggcaag ctgtgacttc tccaggtctc acgggcatgg gcactccctt  1200
ggtggcaaga gcccccttga caccgggggtg gtgggaacca tgaagacagg atggggggctg  1260
gcctctggct ctcatggggt ccaagttttg tgtattcttc aacctcattg acaagaactg  1320
aaaccaccaa aaaaaaaaaa                                              1340
```

```
SEQ ID NO: 4                moltype = AA   length = 193
FEATURE                     Location/Qualifiers
source                      1..193
                            mol_type = protein
                            organism = Homo sapiens
SEQUENCE: 4
MGVHECPAWL WLLLSLLSLP LGLPVLGAPP RLICDSRVLE RYLLEAKEAE NITTGCAEHC   60
SLNENITVPD TKVNFYAWKR MEVGQQAVEV WQGLALLSEA VLRGQALLVN SSQPWEPLQL  120
HVDKAVSGLR SLTTLLRALG AQKEAISPPD AASAAPLRTI TADTFRKLFR VYSNFLRGKL  180
KLYTGEACRT GDR                                                     193
```

```
SEQ ID NO: 5                moltype = DNA   length = 226
FEATURE                     Location/Qualifiers
misc_feature                1..115
                            note = Mouse sequence
misc_feature                116..128
                            note = Human Exon 1
misc_feature                116..226
                            note = Human sequence
source                      1..226
                            mol_type = other DNA
                            organism = synthetic construct
SEQUENCE: 5
tcttccaggc tagtggggtg atctggccct acagaacttc caaggatgaa gacttgcagc   60
gtggacactg gcccagcccc gggtcgctaa ggagctccgg cagctaggcg cggagatggg  120
ggtgcacggt gagtactcgc gggctgggcg ctcccgcccg cccgggtccc tgtttgagcg  180
gggatttagc gccccgggcta ttggccagga ggtggctggg ttcaag                226
```

```
SEQ ID NO: 6                moltype = DNA   length = 1054
FEATURE                     Location/Qualifiers
misc_feature                1..115
                            note = Human Exon 5
misc_feature                1..926
                            note = Human sequence
misc_feature                927..1054
                            note = 5' end of selection cassette
source                      1..1054
                            mol_type = other DNA
                            organism = synthetic construct
SEQUENCE: 6
actccgaaca atcactgctg acactttccg caaactcttc cgagtctact ccaatttcct   60
ccggggaaag ctgaagctgt acacagggga ggcctgcagg acaggggaca gatgaccagg  120
tgtgtccacc tggcgcatatc caccacctcc ctcaccaaca ttgcttgtgc cacaccctcc  180
cccgccactc ctgaaccccg tcgaggggct ctcagctcag cgccagcctg tcccatggac  240
actccagtgc cagcaatgac atctcagggg ccagaggaac tgtccagaga gcaactctga  300
gatctaagga tgtcacaggg ccaacttgag ggcccagagc aggaagcatt cagagagcag  360
ctttaaactc agggacagag ccatgctggg aagacgcctg agctcactcg gcaccctgca  420
aaatttgatg ccaggacacg ctttggaggc gatttacctg ttttcgcacc taccatcagg  480
gacaggatga cctggagaac ttaggtggca agctgtgact tctccaggtc tcacgggcat  540
gggcactccc ttggtggcaa gagcccccctt gacaccgggg tggtgggaac catgaagaca  600
ggatggggggc tggcctctgg ctctcatggg gtccaagttt tgtgtattct tcaacctcat  660
tgacaagaac tgaaaccacc aatatgactc ttggcttttc tgtttctgg gaacctccaa  720
atccctgc tctgtcccac tcctggcagc agtgcagcag gtccaggtcc gggaaacgag  780
gggtggaggg ggctgggccc tacgtgctgt ctcacacagc ctgtctgacc tctcgaccct  840
accgggcctg aggccacaag ctctgcctac gctggtcaat aaggtgtctc cattcaaggc  900
ctcaccgcag taaggcagct gccaacctcg agataacttc gtataatgta tgctatacga  960
agttatatgc atggcctccg cgccgggttt tggcgcctcc cgcgggcgcc ccctcctca  1020
cggcgagcgc tgccacgtca gacgaaggggc gcag                            1054
```

```
SEQ ID NO: 7                moltype = DNA   length = 243
FEATURE                     Location/Qualifiers
misc_feature                1..121
                            note = 3' end of selection cassette
misc_feature                122..243
                            note = Mouse sequence
source                      1..243
                            mol_type = other DNA
                            organism = synthetic construct
SEQUENCE: 7
gcctctgttc cacatacact tcattctcag tattgttttg ccaagttcta attccatcag   60
```

-continued

```
acctcgacct gcagcccta gataacttcg tataatgtat gctatacgaa gttatgctag    120
cgccaacccg ctaggacaag tgctgagtga gctggggcca ccgtttgagg aaacaggagc    180
cagtacagag gggttcccct ttaggggttg gtggcaatgg gcgaccctgg ttaatggatc    240
att                                                                    243

SEQ ID NO: 8            moltype = DNA   length = 20
FEATURE                 Location/Qualifiers
source                  1..20
                        mol_type = other DNA
                        organism = synthetic construct
SEQUENCE: 8
catctgcgac agtcgagttc                                                    20

SEQ ID NO: 9            moltype = DNA   length = 19
FEATURE                 Location/Qualifiers
source                  1..19
                        mol_type = other DNA
                        organism = synthetic construct
SEQUENCE: 9
ccagggagct taccgtgac                                                     19

SEQ ID NO: 10           moltype = DNA   length = 27
FEATURE                 Location/Qualifiers
source                  1..27
                        mol_type = other DNA
                        organism = synthetic construct
SEQUENCE: 10
aggtacatct tagaggccaa ggaggca                                            27

SEQ ID NO: 11           moltype = DNA   length = 19
FEATURE                 Location/Qualifiers
source                  1..19
                        mol_type = other DNA
                        organism = synthetic construct
SEQUENCE: 11
acagccgagt cctggagag                                                     19

SEQ ID NO: 12           moltype = DNA   length = 19
FEATURE                 Location/Qualifiers
source                  1..19
                        mol_type = other DNA
                        organism = synthetic construct
SEQUENCE: 12
aagccctgag cgtgagttc                                                     19

SEQ ID NO: 13           moltype = DNA   length = 26
FEATURE                 Location/Qualifiers
source                  1..26
                        mol_type = other DNA
                        organism = synthetic construct
SEQUENCE: 13
aggccaagga ggccgagaat atcacg                                             26

SEQ ID NO: 14           moltype = DNA   length = 19
FEATURE                 Location/Qualifiers
source                  1..19
                        mol_type = other DNA
                        organism = synthetic construct
SEQUENCE: 14
gagccctgca ctggacaac                                                     19

SEQ ID NO: 15           moltype = DNA   length = 20
FEATURE                 Location/Qualifiers
source                  1..20
                        mol_type = other DNA
                        organism = synthetic construct
SEQUENCE: 15
tcccatgaac gctgagagtc                                                    20

SEQ ID NO: 16           moltype = DNA   length = 28
FEATURE                 Location/Qualifiers
source                  1..28
                        mol_type = other DNA
                        organism = synthetic construct
SEQUENCE: 16
agggtcaagg agccatagac agaatggc                                           28

SEQ ID NO: 17           moltype = DNA   length = 200
FEATURE                 Location/Qualifiers
```

-continued

```
misc_feature           1..100
                       note = Mouse sequence
misc_feature           101..200
                       note = Human sequence
source                 1..200
                       mol_type = other DNA
                       organism = synthetic construct
SEQUENCE: 17
agctctccta ccactagact gctgagaccc gctgctctgc tcaggactcg atttccagta   60
cacaatctcc ctctttgaaa agtaccacac atcctggggt gctcttgcat ttgtgtgaca   120
ctttgctagc caggctcagt cctgggttcc aggtggggac tcaaacacac tggcacgagt   180
ctacattgga tattcttggt                                                200

SEQ ID NO: 18           moltype = DNA  length = 199
FEATURE                 Location/Qualifiers
misc_feature           1..100
                       note = 5' end of neomycin cassette
misc_feature           101..199
                       note = Human sequence
misc_feature           106..139
                       note = LoxP
source                 1..199
                       mol_type = other DNA
                       organism = synthetic construct
SEQUENCE: 18
gctccccatt cctcactggc ccagcccctc ttccctactc tttctagccc ctgcctcatc   60
tccctggctg ccattgggag cctgccccac tggaagccag tcgagataac ttcgtataat   120
gtatgctata cgaagttata tgcatggcct ccgcgccggg ttttggcgcc tcccgcgggc   180
gcccccctcc tcacggcga                                                 199

SEQ ID NO: 19           moltype = DNA  length = 200
FEATURE                 Location/Qualifiers
misc_feature           1..100
                       note = 3' neomycin cassette
misc_feature           101..200
                       note = Mouse Exon 4
source                 1..200
                       mol_type = other DNA
                       organism = synthetic construct
SEQUENCE: 19
cattctcagt attgttttgc caagttctaa ttccatcaga cctcgacctg cagcccctag   60
ataacttcgt ataatgtatg ctatacgaag ttatgctagc tgtctcatag aggctggcga   120
tctggctcag ggacagccag tactgcaaag agtatccttg ttcatacctt ctcctagtgg   180
ccatctccct gggacagtca                                                200
```